United States Patent
Rajasenan

(10) Patent No.: US 8,515,777 B1
(45) Date of Patent: Aug. 20, 2013

(54) SYSTEM AND METHOD FOR EFFICIENT PROVISION OF HEALTHCARE

(75) Inventor: Terry Rajasenan, Pittsburgh, PA (US)

(73) Assignee: ProcessProxy Corporation, Baltimore, MD (US)

( * ) Notice: Subject to any disclaimer, the term of this patent is extended or adjusted under 35 U.S.C. 154(b) by 0 days.

(21) Appl. No.: 13/272,213

(22) Filed: Oct. 12, 2011

Related U.S. Application Data

(60) Provisional application No. 61/392,900, filed on Oct. 13, 2010.

(51) Int. Cl.
*G06Q 50/00* (2012.01)

(52) U.S. Cl.
USPC ............ 705/2; 705/3; 705/7.11; 705/7.12; 705/7.13; 705/7.14

(58) Field of Classification Search
USPC ..................... 705/2–3, 7.11–7.21
See application file for complete search history.

(56) References Cited

U.S. PATENT DOCUMENTS

| | | | |
|---|---|---|---|
| 6,149,585 A * | 11/2000 | Gray | 600/300 |
| 2005/0038669 A1 * | 2/2005 | Sachdeva et al. | 705/2 |
| 2006/0053035 A1 * | 3/2006 | Eisenberg | 705/2 |
| 2009/0089147 A1 * | 4/2009 | Schoenberg | 705/10 |
| 2010/0198609 A1 * | 8/2010 | Mellin et al. | 705/2 |
| 2011/0201898 A1 | 8/2011 | Benco et al. | |

OTHER PUBLICATIONS

Bhattacharya, P., et al, "Automated Data Mining: An Innovative and Efficient Web-Based Approach to Maintaining Resident Case Logs", Journal of Graduate Medical Education, pp. 566-570 (Dec. 2010).
Veluswamy, Ragupathy, "Golden Nuggets: Clinical Quality Data Mining in Acute Care", The Physician Executive, pp. 48-53 (May-Jun. 2008).
Meet RUBI the Robot Tutor, URL: http://www.universityofcalifornia.edu/news/article/18319 (Jul. 30, 2008).
Movellan, J., et al., "HRI '07 Proceedings of the ACM/IEEE international conference on Human-robot interaction: The RUBI Project: A Progress Report", Pub: Association for Computing Machinery, pp. 333-339 (2007).
"Quality and Safety in Health Care: Doctors interrupted at work give shorter and poorer care to patients", BMJ Group (May 13, 2010).
Telis, Gisela, "Multitasking Splits Brain", URL: http://news.sciencemag.org/sciencenow/2010/04/multitasking-splitsthe-brain.html (Apr. 15, 2010).

* cited by examiner

*Primary Examiner* — Sind Phongsvirajati
(74) *Attorney, Agent, or Firm* — David C. Isaacson; Fitzgerald & Isaacson, LLP

(57) ABSTRACT

A healthcare provisioning system improves efficiency in providing healthcare services. Healthcare supply and demand models are analyzed by a healthcare provisioning system to efficiently allocate healthcare supply resources to satisfy healthcare demand. Healthcare supply resources are allocated so as to avoid tipping points that can result in increased costs and negative patient outcomes.

17 Claims, 20 Drawing Sheets

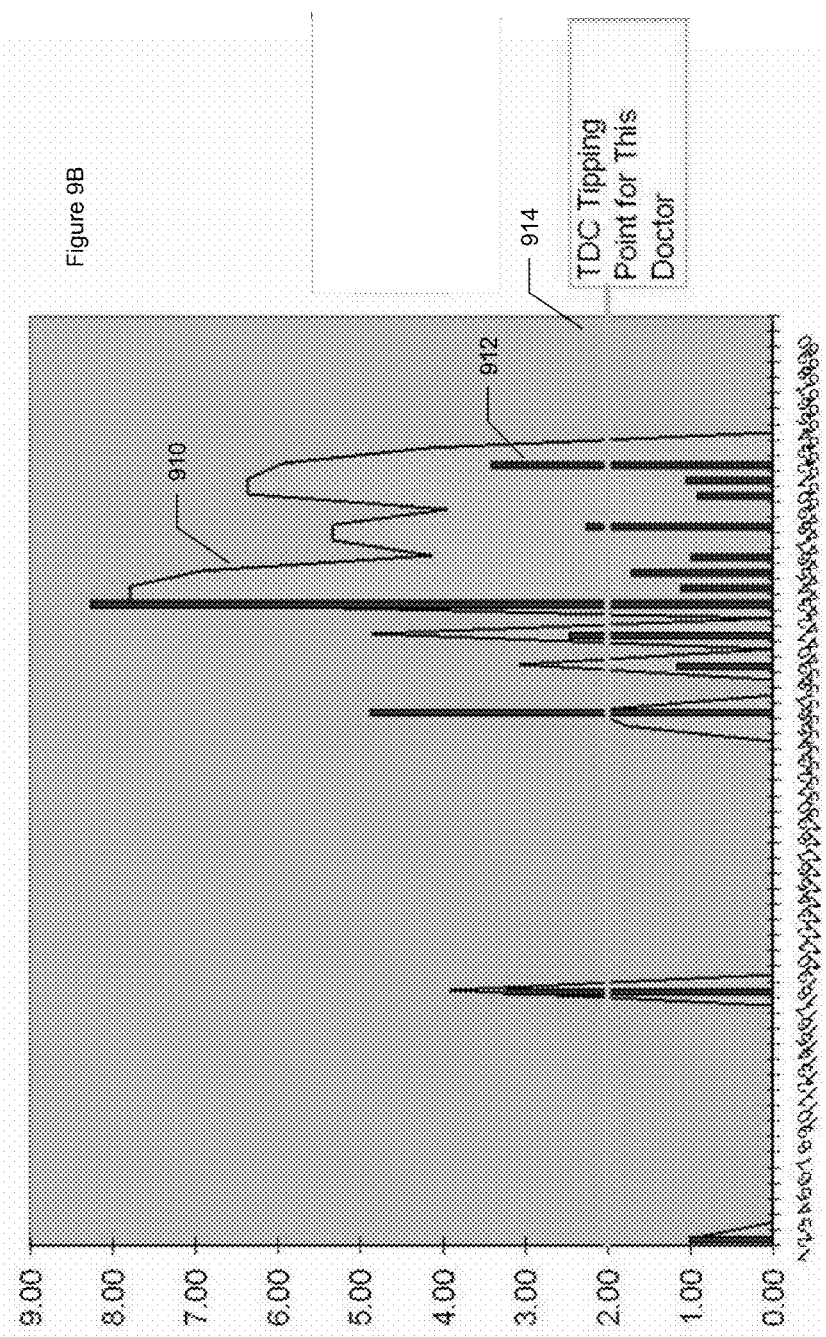

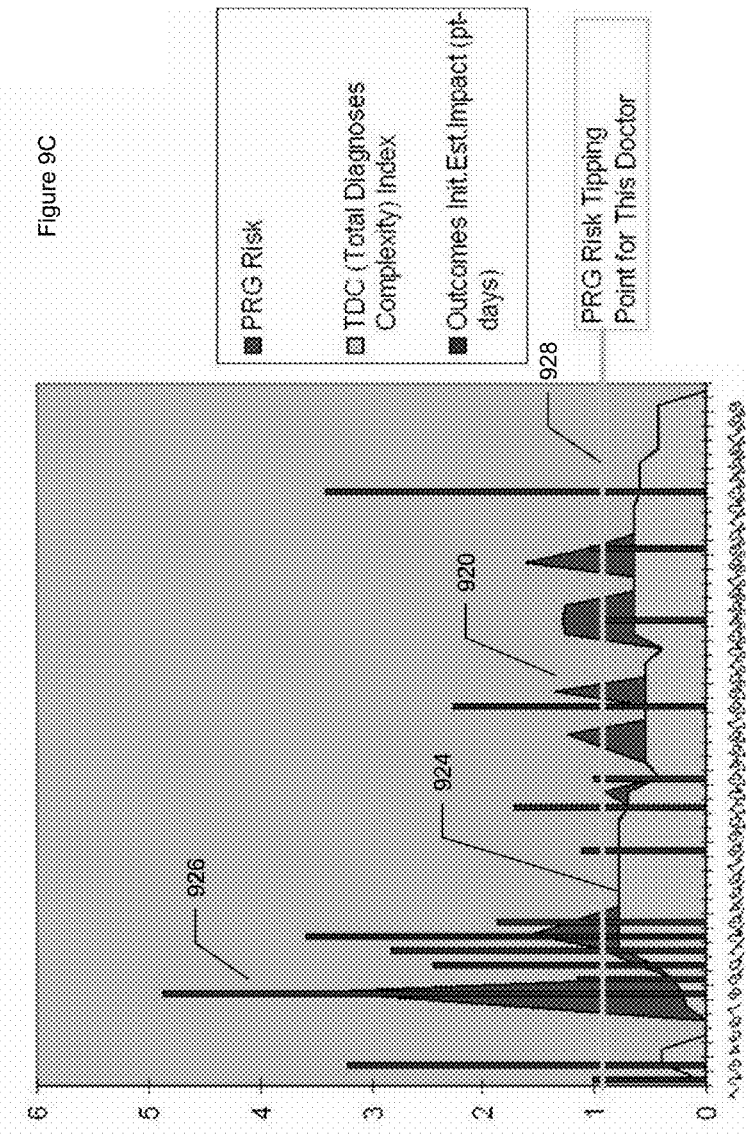

SYSTEM AND METHOD FOR EFFICIENT PROVISION OF HEALTHCARE

CROSS-REFERENCE TO RELATED APPLICATIONS

This application claims the benefit of U.S. Provisional Appln. No. 61/392,900 filed Oct. 13, 2010, which is hereby incorporated by reference in its entirety.

COPYRIGHT NOTICE

A portion of the disclosure of this patent document contains material which is subject to (copyright or mask work) protection. The (copyright or mask work) owner has no objection to the facsimile reproduction by anyone of the patent document or the patent disclosure, as it appears in the Patent and Trademark Office patent file or records, but otherwise reserves all (copyright or mask work) rights whatsoever.

BACKGROUND

1. Technical Field

Embodiments of the present invention relate generally to heath care management. More particularly, embodiments of the present invention relate to efficient provision of healthcare by analyzing healthcare provider supply and patient demand.

2. Background

Healthcare has become a central issue today. For example, recently Congress passed sweeping healthcare reform aimed at providing access to healthcare for millions of people uncovered under the previous healthcare paradigms.

Despite increased access to healthcare, patients often face long waits and must endure healthcare providers not performing optimally. These waits and substantial performance issues can often be traced to poorly managed healthcare systems. The poor management is due, in large part, to lack of tools to efficiently allocate healthcare resources, such as doctors, nurses, equipment, and rooms to patients requiring these services. As a result, conventional healthcare provision is often highly inefficient. This inefficiency can have devastating results. Not only does the inefficiency result in substantially higher healthcare costs, but patient condition can worsen due to the inefficiencies, even to the point of death.

One such inefficiency results from a healthcare provider's limited capacity. Limited capacity can arise in a number of forms. For example, limited capacity can manifest itself as a result of limited knowledge. However, limited capacity is more often the result of the healthcare provider becoming overwhelmed by case load. Whether a healthcare provider is responsible for too many patients, a reasonable number of patients that require differing amounts of care at the same time, or a reasonable number of patients, where some cases increase in complexity, a healthcare provider can provide only so much care at a particular quality level before the quality level begins to decrease.

Other factors also affect healthcare costs and provider efficiency. For example, length of stay ("LOS") tends to have a significant impact of healthcare cost and efficiency. LOS metrics can be used to correlate or predict a patient's expected LOS for a given diagnosis. In addition, a healthcare provider can gather its own LOS metrics. For example, a healthcare provider can computer an arithmetic mean length of stay ("AMLOS") for each patient and/or those patients having a particular diagnosis. The patients' actual LOS is then compared against this benchmark. Problems can be indicated when LOS is greater than the LOS predicted by AMLOS.

In addition to LOS, the number of diagnoses for a particular patient has an effect on healthcare costs. For example, a patient diagnosed with congestive heart failure ("CHF") has an expected cost. However that cost will likely rise in an exponential manner if there are additional diagnoses, for example, pneumonia. As is well known, many patients are often associated with a number of diagnoses. In fact, both Medicare studies and others (including Dr. Don Berwick of the Institute of Healthcare Improvement) have noted that approximately 70% of costs can be attributed to just 10% of patients.

SUMMARY

A healthcare provisioning system according to an embodiment improves efficiency in providing healthcare services. Supply and demand models are analyzed by a healthcare provisioning system to efficiently allocate healthcare supply resources to satisfy healthcare demand. Healthcare supply resources are allocated so as to avoid tipping points that can result in increased costs and negative patient outcomes.

In an embodiment, a healthcare provisioning system includes a computer, a healthcare demand model, and a healthcare supply model. In the embodiment, a healthcare provisioning system executing on the computer analyzes the healthcare demand and supply models to determine allocation of healthcare supply resources to meet healthcare demand to avoid reaching healthcare supply tipping points.

In another embodiment, a method for providing healthcare includes generating a healthcare demand model on a computer, generating a healthcare supply model on the computer; and analyzing the healthcare demand and supply models on the computer to determine allocation of healthcare supply resources to meet healthcare demand to avoid reaching healthcare supply tipping points.

BRIEF DESCRIPTION OF THE DRAWINGS

FIG. 9B illustrates complexity load factor viewed from a diagnoses per day perspective.

FIG. 9C illustrates an example of considering how healthcare supply affects tipping point.

DETAILED DESCRIPTION

Embodiments of the present invention are directed to reducing the cost of healthcare and the worsening of patient condition that can result from inefficiencies in providing healthcare under conventional paradigms. In an embodiment, cost reduction is achieved using one or more of the following basic principles: (1) comparative advantage, (2) the Pareto principle, and (3) the Metcalfe network effect. Briefly, "comparative advantage" refers to the concept that one actor can provide a product or service at a lower opportunity cost than another actor. As a result, even where one actor is better at providing a product or service than another, it may be to that actor's advantage, as well as to an organization as a whole, for that actor to work with the other actor rather than working alone. The Pareto principle refers to the concept that in many situations, 80 percent of the effects result from 20 percent of the causes. The Metcalfe network effect refers to the idea that the value of a network increases in proportion to the square of the number of nodes in the network.

In embodiments, these principles are applied in a number of ways, including (1) labor arbitrage to staff flexible resources from one patient to another making use of the Metcalfe Network principle that 5% change in staffing can reduce overstaffing, overtime, and agency staffing costs by 50%; (2) process arbitrage to assign tasks to flexible resources, to follow in-house best practices ("IHBP") that can considerably improve performance; (3) load balancing of healthcare provider tasks, or task redistribution, to maximize efficiency by maximizing comparative advantage; and (4) load reduction through process adaptation, where machine learning enables reductions in task time and/or task pattern complexities. An IHBP provides the most cost effective quality based results that is achieved in a patient encounter analyzing the Joint commission core measures, safety issues, clinical outcomes, patient satisfaction and resource utilization.

In healthcare, supply and demand are not represented by a tangible product (like selling a computer) nor just a handshake. Instead, like any complex service healthcare supply and demand can be represented as a process—a series of tasks to fulfill the need in a way that meets quality standards quickly and cost-effectively. Embodiments provide better patient safety, productivity, and task execution through cognitive capacity management using load balancing, from data mining, predictive modeling, and telehealth. Proxy in processproxy is partially the inference of process steps based on data, then also our automation serving as proxy (or surrogate) for some of the tasks in a process to create slack capacity which helps in load balancing. (task-centric) TAR-->Load Balancing to avoid Tipping Points-->Executed Tasks.

Figure 1:
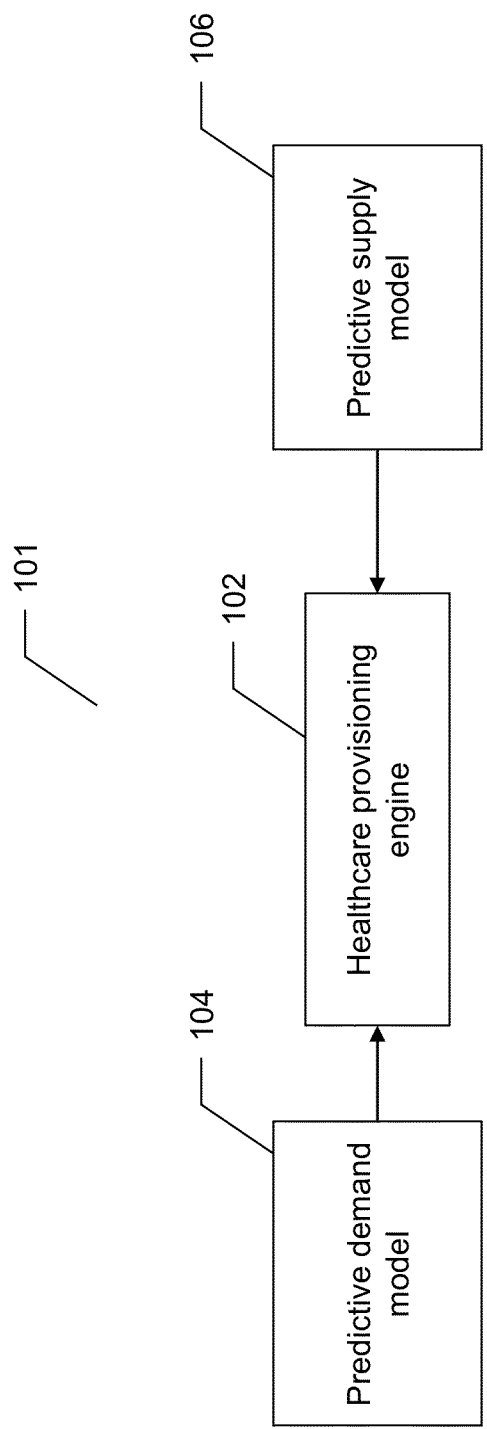
FIG. 1 is a block diagram of a healthcare provisioning system according to an embodiment.

FIG. 1 is a schematic diagram of a healthcare provisioning system 101 to improve efficiency of providing healthcare according to an embodiment of the present invention. In an embodiment, healthcare provisioning system 101 includes a healthcare provisioning engine 102, a healthcare demand model 104 and a healthcare supply model 106. In an embodiment, healthcare demand model 104 and healthcare supply model 106 are predictive models based on predictions of what the likely demand and supply are at a given point in time. For example, in an embodiment, healthcare demand, includes, without limitation cognitive consumption (drain of mental resources of available healthcare supply), and healthcare supply includes, without limitation cognitive capacity (available mental processes of healthcare supply that can be devoted to meet the healthcare demand). Healthcare provisioning engine 102 avoids "patient crashes" (negative patient outcome such as worsening of condition or death) caused by patient safety errors and complications that can lead to preventable patient deterioration or death, and preventable costs, by optimally apportioning healthcare supply to meet healthcare demand in the most cost-effective manner given the current supply and demand situation. For example, in an embodiment, executing the right tasks at the right time can help reduce the risks of preventable deteriorating conditions or death, and costs. However, the tasks themselves may also be "at risk" due to crucial issues, such as limited healthcare supply to perform the at risk task(s). Therefore, to ensure these tasks can get done when there is risk of overload requires determining which tasks are fungible and can thus be offloaded for greater comparative advantage and efficiency. By ensuring at risk tasks are performed, embodiments ensure better adherence to IHBP.

In an embodiment, healthcare provisioning engine 102 attempts to allocate available healthcare supply to satisfy healthcare demand in an efficient manner. For example, in an embodiment, healthcare services are supplied so as to prevent healthcare supply resources from reaching tipping points. In an embodiment, healthcare supply refers to available healthcare resources. For example, without limitation, in an embodiment, healthcare supply includes doctors, mid-level providers, nurses, and other healthcare team staff available to care for patients as well as also equipment and room availability. In an embodiment, healthcare demand refers to users of healthcare resources. For example, without limitation, in an embodiment, healthcare demand refers to patients requiring healthcare—and those caregivers that require tasks offloaded, such as the ordering or administering of medications.

Figure 2:
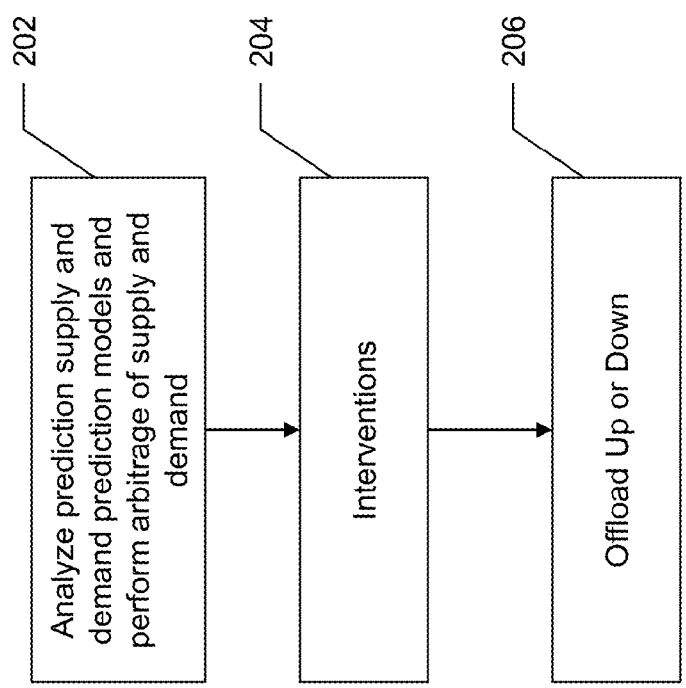
FIG. 2 illustrates a flow chart for a healthcare provisioning engine according to an embodiment.

In an embodiment, healthcare provisioning engine 102 is configured to execute on a computer. Any computer that can be configured to execute a healthcare provisioning engine 102 as described herein can be used. For example, in an embodiment, healthcare provisioning engine 102 can be configured to execute on a personal computer, such as an IBM-PC computer or clone, an Apple MacIntosh computer, or other (larger than PCs) computer systems or devices with able to run the Smartgrid computer software. FIG. 2, is a high-level schematic diagram of a computer that can be configured to execute a healthcare provisioning engine 102 as described herein.

In an embodiment, healthcare provisioning engine 102 uses predicted supply and demand metrics to determine how to best allocate available healthcare supply to satisfy healthcare demand. For example, in an embodiment healthcare supply provisioning engine 102 uses a predictive healthcare demand model 104 and a predictive healthcare supply model 106 to determine at risk tasks. At risk tasks are those tasks that may not be performed by a given healthcare supply in response to a given healthcare demand. For example, in an embodiment, healthcare provisioning engine 102 coordinates most efficiently healthcare provider supply to avoid not performing at risk tasks.

In some cases, not all at risk tasks will be performed. To avoid nonperformance of critical at risk tasks, in an embodiment, healthcare provisioning engine 102 prioritizes at risk tasks according to the consequence of not completing the at risk task. Those at risk tasks that have greater consequences (such as patient death) are given priority in assigning healthcare supply to avoid not completing the at risk task.

Further, in an embodiment, healthcare provisioning engine 102 can identify critical paths in a process and the break points (or potential failure points in a process) that can be resolved to improve efficiency. For example, in an embodiment, healthcare provisioning engine 102 can use the TIMSA-DAP methodology described in U.S. patent application Ser. No. 11/562,857, which is incorporated by reference herein in its entirety. These break points can be used to assist in identifying "tipping points." In an embodiment, the term tipping point refers to the point at which a particular healthcare supply has reached its capacity to supply healthcare service at an acceptable quality. For example, a tipping point may be reached when a doctor has reached the maximum number of patients of a certain level and/or pattern of complexity for whom he or she can provide quality healthcare. A tipping point can also be reached by a facility, such as when the number of available rooms has reached a point where new patients can no longer be admitted. When a tipping point is reached, provision of healthcare services can be compromised and patient safety can be at risk. For example, tasks required to care for a particular patient may not be performed, or may not be performed adequately. The consequences of not performing such at risk tasks can be catastrophic in healthcare situations.

In an embodiment, healthcare provisioning engine 102 operates on inputs from a healthcare demand model 104 and a healthcare supply model 106. Healthcare demand model 104 provides a prediction of the demand for healthcare services that needs to be satisfied. As described in more detail below healthcare demand model 104 is created by creating an initial healthcare demand model based on historical and similar demand indicators (such as lab values, documentation cues, etc.) and then updating that model using real-time clinical surveillance related to healthcare demand. For example, in an embodiment, such clinical surveillance related to healthcare demand includes monitoring a patient's condition. Other clinical data related to healthcare demand can be monitored and used to update the initial healthcare demand model.

As described in more detail below healthcare supply model 106 is created by creating an initial healthcare supply model based on historical and similar supply and then updating that model using real-time healthcare clinical surveillance related to healthcare supply. For example, in an embodiment, clinical surveillance related to healthcare supply includes monitoring a healthcare provider's patient and task workload for all their patients or their assisting of other caregivers to determine if the healthcare provider's tipping point has been reached. Other clinical data related to healthcare supply can be monitored and used to update the initial healthcare supply model.

Healthcare provisioning engine 102, healthcare demand model 104, and/or healthcare supply model 106 use inputs from a number of sources in a healthcare system to improve provisioning of healthcare. For example, healthcare provisioning engine 102 can accept input from patient intake databases, lab result databases, scheduling databases, healthcare databases, healthcare information exchanges, health system messaging systems, and other sources to obtain information required to create healthcare demand and supply models as described herein.

FIG. 2 illustrates a flow chart for a healthcare provisioning engine 102 according to an embodiment of the present invention. In step 202, healthcare provisioning engine 202 analyzes supply and demand prediction models and performs an arbitrage of supply and demand resources based on the analysis to most efficiently allocate available healthcare supply to meet healthcare demand to maximize overall value to the electronic business community where the task exchange is being performed. Supply and demand analysis can be on a patient-by-patient or healthcare provider-by-healthcare provider basis. Further, the demand and supply models can be based on facility data, regional data, world-wide data, or data of any other scope.

In step 204, healthcare provisioning engine 204 identifies interventions that may need to be performed to improve healthcare provisioning efficiency. In an embodiment, for example, a set of interventions can be done, both as actions by persons, as well as actions done by other effectors used to provide healthcare (e.g., cellphones/smartphones that can notify, robots that can act, etc.) to in effect offload poorly-fitting tasks among each of a care team, to those more ideally suited. These tasks can include a variety of care-oriented processes, such as making calls to consultants, taking histories of patients and identifying risk factors, ordering medicines like ACE inhibitors, typing in or dictating notes, printing out reports, etc. Moreover, to further reduce load levels of the caregivers and more quickly identify and aid potentially overloaded caregivers and their at risk tasks, one could harness an Augmented Reality use case that would be able to point a smartphone, tablet computer, etc., with a camera, at a caregiver, see the caregiver, the load level, and the Patients At Risk, Tasks At Risk, then determine what tasks might be best to offload from the caregiver.

In an embodiment, determining interventions also includes using process adaptation to translate work to fit understanding of a potential supply of labor, or to take over (using various effectors to essentially accomplish the task automatically) the work altogether. It can also include telemedicine items like robots or other means for video capture (for review later on Smartphones or computers), or video conferencing, and where "off-site flex resources" are used to help offload tasks (in addition to on-site flex resources as well). In short, finding additional supply by increasing the number of caregivers able to execute offloaded tasks that can reduce overall load on caregivers near tipping points, or reduce the cognitive complexity of the tasks of the overloaded caregivers themselves.

In an embodiment, the interventions include offloading tasks "up" (i.e. offload tasks that are too difficult, or at least get reinforcement from others to avoid a process breakdown, and also includes trading sideways where specialists find tasks they can swap out to each other to do better) or "down" (i.e., offload less important and simpler multitasks to other people, e.g., flexible resources—or it may include dropping the task altogether, so that more concentration can be given to the Complex Task Patterns ("CTPs")).

In an embodiment, healthcare provisioning engine 102 predicts when an "intervention" will be required to prevent the occurrence of tipping points. An intervention is required when a healthcare provider is about to reach or has reached a tipping point. Tipping points can be predicted by evaluating a complexity load factor for a healthcare provider, based on comparing clinical surveillance data for current patient load being managed against historical data that help determine past failure patterns, or looking at current data that indicates high stress (e.g., from biometric sensor data of the caregiver or individual's behavior data as indicated by video data) and comparing to when this individual reaches tipping points in the past. In an embodiment, the tipping point is a function of supply and demand overload indicators. Thus, comparing supply and demand overload indicators provides a better prediction of the need for intervention.

Interventions to prevent tipping points include, without limitation, mobilization of flexible resources to offload tasks from a healthcare provider so that the healthcare provider will not reach a tipping point that will negatively affect patient care and/or organizational efficiency. To maximize organizational efficiency and obtain disproportionate returns, the system should maximize the number of caregivers that can be prevented from reaching their tipping point. Task offloading can be accomplished by finding alternate flexible resources to perform tasks that would otherwise be performed by the healthcare provider. Flexible resources are those people (including other physicians, nurses, other health care providers and even the patient themselves or patients' families) most capable of moving into and adapting into a new lead or support situation to help an attending physician ensure patients face the least risk in terms of complications, patient safety sentinel events, and other poor, unexpected outcomes.

In an intervention, flexible resources are assigned to assist the healthcare provider that is predicted to reach, or is showing signs of having reached, a tipping point. The flexible resources are assigned to reduce the healthcare provider's complexity load factor. For example, flexible resources can be assigned to assist the healthcare provider by offloading certain tasks from the healthcare provider. For example, flexible resources can be assigned to handle more mundane tasks such as transcribing dictations, or can be assigned to see less critical patients. Assignment of flexible resources is based on scheduling data available to the system.

Flexible resources, include, but are not limited to, consulting physicians, residents, physician's aides, nursing staff, nurse practitioners, and other available clinical support staff. Consulting physicians, for example, can place orders on behalf of direct care providers and assist with documentation such as coding. Nurses, for example, can call doctors to get verbal orders based on, for example, in-house best practices ("IHBP"), can accompany direct care providers on rounds as they may be more familiar with a case, perform intake and assessment, and assist with computer related tasks. Other flexible resources include, for example, quality control persons to ensure compliance with IHBP, case managers to help avoid denials and plan each discharge ("D/C"), clinical documentation improvement staff, and nurse practitioners and physician's assistants to help manage cases and assist direct care providers to reduce the occurrence of tipping points.

In an embodiment, real-time clinical surveillance related to healthcare demand is done by taking data extracts concerning patient diagnoses and protocols related to those diagnoses. The data found as or around keywords is then processed and weighted, depending on the keyword or value found in the data, and its context (i.e., in lab, med, section of a dictation, etc.). For example, in an embodiment, the data is placed into CSV format or directly into Microsoft Excel. A scoring mechanism is used to model and predict the risks (based on the available data). A filter is applied to determine only those risks above a threshold value. This will then offer results in the form of one or more diagnoses that have some quantified degree of probability ascribed to them.

In an embodiment, healthcare provisioning engine 102 performs process data mining to determine the tasks expected to be demanded for treating various types of patients. For example, in an embodiment, process mining is performed by looking at event logs to see what was done based on available data, the time it was estimated to be done or exactly done, and finally inferring the tasks. The tasks that will with some degree of probability be needed, when it is not one diagnosis that uses a single order set, will be based on an IHBP. One such order set analysis is described in the Veluswamy, Ragupathy, "Golden Nuggets: Clinical Quality Data Mining in Acute Care," Journal of the Physician Executive (May-June 2008), which is hereby incorporated by reference herein in its entirety.

In step 206 healthcare provisioning system 102 analyzes workload of healthcare supply resources to determine whether tipping points are being reached. For example, healthcare provisioning system 102 can analyze the number of patients a particular healthcare provider is caring for. If that number is too high, in an embodiment healthcare provisioning system 102 reassigns the patient to another healthcare provider so as to eliminate the tipping point as described above. Alternatively, healthcare provisioning engine 102 assigns tasks that would otherwise be performed by the healthcare provider to another healthcare provider.

Figure 3:
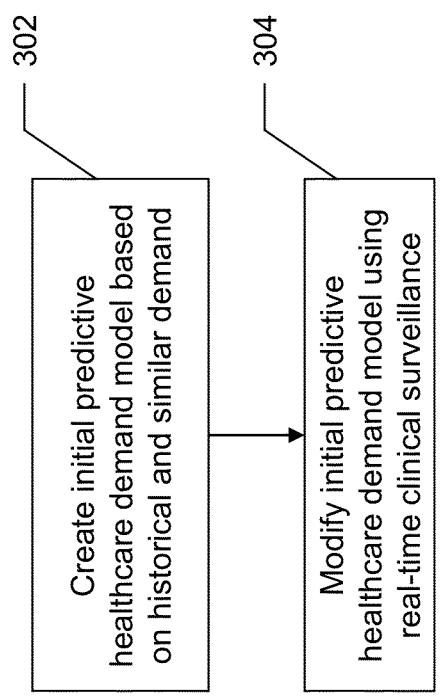
FIG. 3 is a flow chart for a method for generating a healthcare demand model according to an embodiment.

FIG. 3 is a flow chart for a method for generating a healthcare demand model according to an embodiment of the present invention. In step 302, an initial predictive healthcare demand model is created. In an embodiment, the initial predictive healthcare demand model is created using historical and similar healthcare demand data.

In an embodiment, when a patient enters a healthcare facility, diagnoses based on symptoms the patient presents on such arrival are determined. The diagnoses can be based on any number of symptoms the patient presents. For example, in an embodiment, the system determines the diagnoses by consulting a database that correlates symptoms or diagnostic indicators to diagnoses and strength of indication, which can indicate the probability of that diagnosis being present or the intensity of the diagnosis or its severity. The database of rules can be provided by governmental health organizations (e.g., the manuals case managers use for determining acceptable criteria), the healthcare system of which the healthcare facility is a member, or any other source that correlates symptoms with diagnoses, including modeling of claims data for the facility stating diagnoses compared to the raw data available for those patients found in the claims data.

The database can also include diagnoses correlated with sets of symptoms against a database containing sets of symptoms. In this manner, the set of symptoms presented by the patient can be considered rather than each symptom individually. In an embodiment, both types of databases can be consulted.

In addition to databases, diagnoses can be determined from other sources. For example, in an embodiment, using data delay analysis and intervention lead time analysis, diagnoses can be predicted with an associated weighted probability within a particular time period. The probability is based on indicators of a particular diagnosis. Such indicators include, without limitations, ED notes from physicians, physical examination and lab reports. Each of the sources of predicted diagnoses is assigned a probability. Summing the probability over available prediction sources provides an estimate of the probability a patient has a particular diagnosis.

This diagnosis can be updated at various times during a patient's stay. For example, a diagnosis may be predicted when the patient is admitted or walks in the door, when a particular indicator is ordered, when the result of an indicator order is confirmed or entered into the system, when a record is sent to healthcare provisioning engine 102, the time before a prediction of a particular diagnosis is made, and the time between the prediction being made and the healthcare facility acting upon the prediction.

In operation, once a complexity pattern of a patient is obtained, the load and type of case it is to segment the patient (i.e. their profile) for targeting them the right intervention to improve process. With the load, and process step where that patient is at, the appropriate intervention based on the type, load, and stage in process that would accelerate the care appropriately can be determined. As a result, the quality of care will be improved.

For example, assume that the following indicators are available, and have the probabilities of a diagnosis being correct as indicated:
1. ED Notes from Physician—says that he has PN (Accounts for 50% of prediction)
2. Chest XRAY (Accounts for 25%)
3. Sputum Culture (Accounts for 10%)
4. WBC Count (Accounts for 5%)
5. Antibiotics (Accounts for 5%)
6. Blood Culture (Accounts for 5%)

Accuracy depends on the number of indicators that are available at the end of a time period, for example 24 hours. For example, if only Indicators 4, 5 and 6 are available at the end of the time period, then the diagnosis can only be predicted with a 15% (5+5+5) accuracy. As a result, a prediction on that basis leaves a 85% margin for error. The lead time in this case is when these 3 items are available.

By way of further example, in an embodiment, Clinician Capacity Mining Analysis ("CCMA") can be utilized to identify tasks that are or are not getting done in patient care and which caregivers are wholly or partially (if in healthcare team) responsible in order to create a risk model (that can be audited for both tasks done or not done correctly, as well as responsibility attribution) for each caregiver.

This risk model helps determine what tasks are at risk when certain caregivers are teamed together, so that teaming strategies can consider this information based on risk tolerance. For example, by performing an audit of the medications given by a provider for a CHF patient case, it may be identified that the care provider failed to order the appropriate medication, AceArb: No AceArb under medication→detect FINS→who's involved→keep score in list→indicates this care provider has been involved in cases that were incomplete.

It also helps identify which caregivers may need training or instead support, based on information the risk model provides, so that daily training and support strategies can be undertaken. For example, if a caregiver has consistently failed performing a specific task well in the past, then the caregiver would likely will benefit from task education/training. However, if a caregiver has done well "many" times in the past, but seems to have problem points, especially lately, then overlay the caregivers load information onto those cases. If load was high at same times tasks were poor, then likely culprit was cognitive overload, and thus less need for training and more need for support during overload periods for this task, since this task is at risk during this clinician's overload (if load is low, then may be other distraction or hidden load). In, the event the error was due to cognitive overload, then unnecessary training may be avoided; thus saving money and the trainer's time and reduces the load on caregivers pulled in or interrupted for training.

In an embodiment, data received from each of the sources is converted to a format suitable for processing. For example, in an embodiment, the source data is converted into a common or standard format for processing. Such common or standard format can be the HL7 format, a text format, a CSV format, or any other suitable format. In an embodiment, some or all of the source data is maintained in its native format.

In an embodiment, healthcare provisioning system 102 uses the determined diagnoses to predict what tasks will be required to render healthcare to that patient. Which tasks are required can be determined from a number of sources, including a database correlating tasks to diagnoses provided by governmental agencies, a database of IHBP, healthcare facility-wide database, a healthcare information exchange, or any other source that correlates task required to treat particular diagnoses or sets of diagnoses (e.g., clinical protocols or order sets). The predicted tasks are used to create an initial predictive healthcare demand model. As described below, the set of predicted tasks is used to assign healthcare providers to care for the patient.

In an embodiment, tasks required to treat all patients in the health care facility are determined in a similar manner. This will provide a facility-wide view of the tasks that need to be completed for all patients. Using this information as described below, healthcare provisioning engine 102 can estimate demand in expected tasks and also in terms of preoccupation or worry (especially relating to possible mortality) about the patient that the caregiver has, current remaining cognitive capacity to remember and execute tasks, then how to allocate and schedule resources throughout the healthcare facility to maximize the number of prioritized value tasks that can be completed as well as cognitive capacity that can also be freed to improve the creative problem-solving of the caregiver.

In step 304, the initial predictive demand model is modified based on what actually occurs. In an embodiment, machine learning is used to update the initial predictive healthcare demand model. For example, in an embodiment, the initial predictive healthcare demand model is modified using real-time clinical surveillance data. For example, in an embodiment, such clinical surveillance related to healthcare demand includes monitoring a patient's condition. Other clinical data related to healthcare demand can be monitored and used to update the initial healthcare demand model. The updated healthcare demand model can be used to update and improve the prediction for healthcare demand that needs to be satisfied.

In an embodiment, the machine learning can employ a feedback loop to determine whether the initial assessment of diagnoses is correct based on the symptoms initially presented by the patient when admitted by the healthcare facility. Use of the feedback loop allows the system to determine whether the initial diagnoses predicted by the system upon patient admission was correct or requires updating. In an embodiment, the diagnoses for the patient are reexamined periodically. The period can be any time frame, for example, per day, per half day, or randomly. Based on the diagnoses exhibited by the patient, the initial predictive healthcare demand model can be updated to reflect what the patient actually exhibited.

Figure 11:
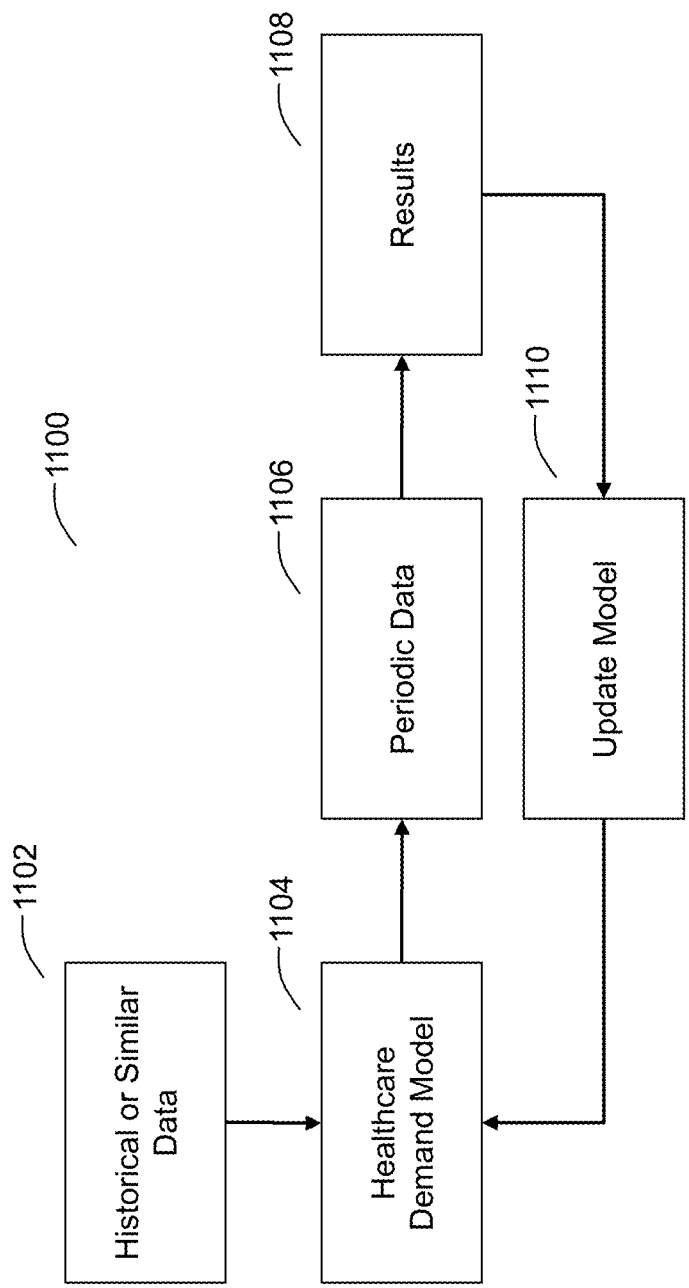
FIG. 11 illustrates an exemplary flowchart for a feedback loop used in an embodiment to update the set of diagnoses to be predicted when a patient presents a particular set of symptoms on admission.

FIG. 11 illustrates an exemplary flowchart 1100 for a feedback loop used in an embodiment to update the set of diagnoses to be predicted when a patient presents a particular set of symptoms on admission. Past historical or similar data is collected in step 1102. As described above, the past data can be determined by looking up diagnoses according to symptoms presented by a patient on admission to a healthcare facility. In step 1104, the past data is used to create a predictive healthcare demand model. In step 1106, patient data concerning diagnoses is collected over a time period. The time period can be periodic, for example, once a day, twice a day, every other day, etc. In another embodiment, the time period is random. Results are analyzed in step 1108 to determine the actual diagnoses presented by the patient. The results can be used to update the predictive model in step 1110. In this manner, when a new patient present similar diagnoses, the initial predictive demand model is likely to be closer to what the patient will actually experience. As a result the tasks that are assigned are more likely to be those that will be required to treat the patient.

In essence then, healthcare demand analyzes a patient that has needs (or diagnoses) that must be met (treated) within a certain time frame. In an embodiment, these needs are transformed into a set of tasks that must be completed within a given time frame for a successful outcome. If the demand is not met within the time frame, significant consequences, including death, can occur.

In an embodiment, tasks are assigned to healthcare providers so as to avoid to the extent possible healthcare provider from reaching or exceeding tipping points. Avoiding healthcare provider tipping points meets the demand in a cost effective manner. However, in avoiding a tipping point for one healthcare provider, it is important not to cause another healthcare provider to go over a tipping point.

When a tipping point occurs, the harm of a healthcare provider providing additional treatment outweighs the benefit of providing that treatment. For example, if the healthcare provider has reached his or her personal limit capacity for handling n patients, assignment of an $n+1^{st}$ patient would push the healthcare provider over the tipping point, and care for all of the patients would suffer. Typically, the healthcare provider does not forget how to treat the patient in general, but rather his or her workload reached the tipping point so that his or her performance suffered as a result as specific tasks that could be essential are at greater risk of being forgotten, or also that thinking capacity required to solve problems (that can't be found in the usual checklists and clinical order sets don't apply sufficiently to the patient the caregiver is treating) is so diminished that the caregiver is not able to solve the problem nearly as well as they could if they had not crossed their tipping point.

Cost-effectiveness increases dramatically when tipping points are prevented. Further, preventing tipping points drastically reduces catastrophic failures in provision of healthcare. In an embodiment, tipping points are prevented by making sure required tasks are performed by someone, even if not the healthcare provider assigned to the task. For example, certain tasks that are found in In-House Best Practices must be performed. Such tasks may be given a higher priority to ensure their completion. In an embodiment, if the healthcare provider has reached the tipping point for performing that task, healthcare provisioning engine 102 will assign the critical task to a flexible resource (a different doctor, nurse, support staff, etc.) for completion. Alternatively, healthcare provisioning engine 102 will offload another different and less important tasks from the healthcare provider to flexible resources for completion.

Figure 4:
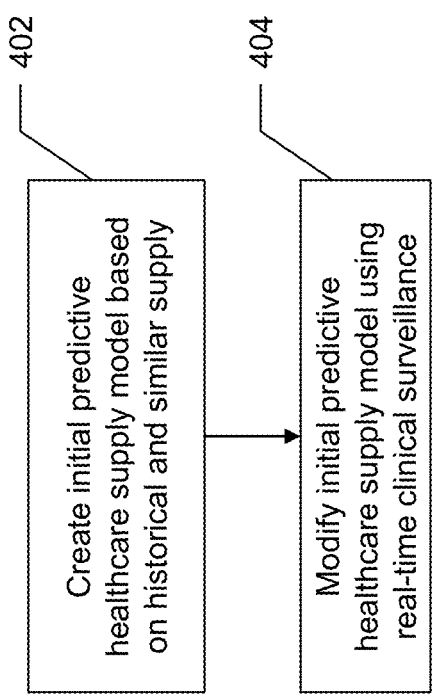
FIG. 4 is a flow chart for a method for generating a healthcare demand model according to an embodiment.

FIG. 4 is a flow chart for a method for generating a healthcare supply model according to an embodiment of the present invention. In step 402, an initial predictive healthcare supply model is created. In an embodiment, the initial predictive healthcare supply model is created using historical healthcare supply data as described above.

In an embodiment, the model of healthcare supply takes into particular account the critical challenges presented by tipping points (e.g., balancing between fully utilizing a person and their skills, versus over-utilizing). In an embodiment, the healthcare supply model is developed to determine when a healthcare provider will become too inefficient (and disproportionately so) due to reaching a tipping point, using historical data on that healthcare provider, or comparing to similar healthcare providers, and then finally also looking at real-time data (e.g., from cameras, biometric sensors, and other sensor devices, etc.) to detect with the highest possible accuracy when a healthcare provider is about to reach his or her tipping point. This provides a tipping point-related load factor for the healthcare provider to be monitored and managed.

In an embodiment, the arbitrage attempts to assign healthcare supply resources, such as healthcare providers, equipment, rooms, etc. to satisfy required demand. For example, in an embodiment, a doctor may be assigned to provide care for a particular patient based on tasks required to care for that patient. For example, a cardiac specialist may be assigned to provide care for a patient having a need for cardiac care. The use of specialized task forces is most often most effective due to the complex nature of healthcare tasks and the reality of caregivers getting quickly overwhelmed and bogged down not only the more complex the tasks become, but also the more unfamiliar they are with the tasks or processes.

As described above, it is often the case that a particular disease or patient will have a number of diagnoses associated therewith and, as a result, increased costs. This is because healthcare costs tend not to be linear with respect to the number of diagnoses, but rather non-linear, such as exponential, since multiple organ system failures require so much more time, effort, and expertise to avoid mortality. Thus, the sicker and more complex the patient the greater the cost in a non-linear measure. As a result, in an embodiment, ways are sought to reduce patient complexity and/or identify Present On Admission ("POA") diagnoses that can impact complication (i.e., complexity) rates. That is, in an embodiment, complexity load factor on a particular healthcare provider, and for all healthcare providers overall is sought to be reduced as much as possible, with a given flexible resource supply.

Initially, the tipping point load factor for a healthcare provider can be approximated by looking at patients complexity scores over one or more patients being cared for by the specific healthcare provider, determined by some level of attribution of the caregiver's involvement with the patient (which can be preset by the type of data available in the facility implementation), perhaps to some degree of weighting (so someone ordering a single test or medication may get less weight than someone that evaluated the patient in a progress note or history and physical, or versus someone that has said they are caring for the patient in some communication order), and complexity diagnoses patterns (to approximate the complexity task patterns) being handled concurrently by this healthcare provider. Then, the estimated tipping points per healthcare provider (in terms of what level of simultaneously managed patients of a certain diagnosis pattern, or mix of diagnosis patterns) are analyzed to see if the patients' complex task patterns ("CTP") are too much for the healthcare provider. It is important to realize that some healthcare provider can handle complexity patterns that would be higher risk CTPs to other healthcare providers, based on their training, practice, and familiarity with the CTP. This must be taken into account in the tipping point determination for any individual.

Figure 8:
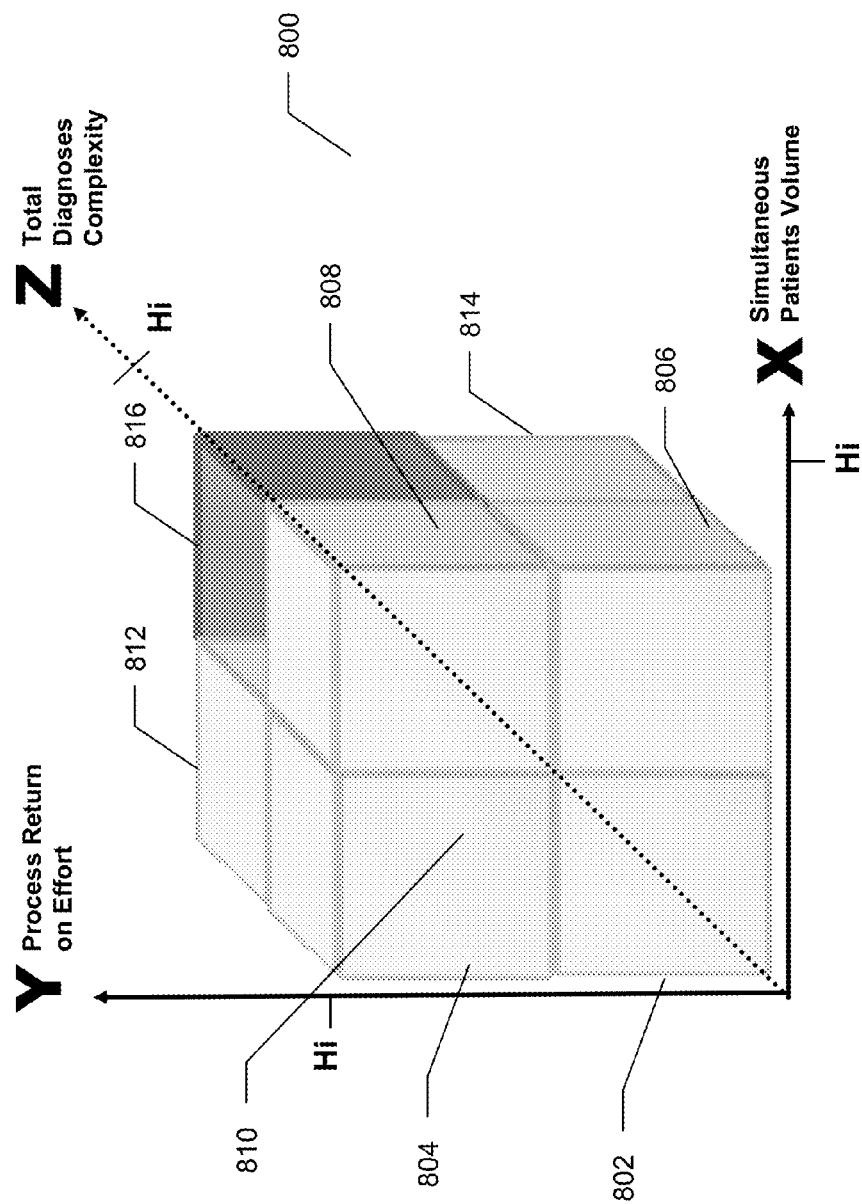
FIG. 8 provides a graphical illustration of an exemplary load factor for a healthcare provider.

FIG. 8 provides a graphical illustration of an exemplary "load factor" for a healthcare provider. In FIG. 8, load factor is represented as a three dimensional cube 800 extending along X-, Y-, and Z-axes. The X-axis represents simultaneous patient volume for the healthcare provider. The Y-axis represents process return on effort ("ROE"), that is, the benefit of the healthcare provider providing care versus the effort required by the healthcare provider to provide the care. The Z-axis represents total diagnosis complexity for the healthcare provider over the entire patient load. Cube 800 comprises octants 802, 804, 806, 808, 810, 812, 814, 816, and 818.

In octant 802, where patient load is small, diagnosis complexity is low, and process ROE is low, the load factor is such that the healthcare provider does not require additional assistance. In octant 804, where the process ROE is high, while patient volume and diagnosis complexity are low, the load factor is such that the healthcare provider may benefit from using order sets to provide the care. In octant 806, where the patient volume is high but diagnosis complexity and process ROE are low, the load factor on the healthcare provider is such that the healthcare provider would benefit from finding flexible resources to offload tasks the healthcare provider would otherwise have to do. In octant 808, where patient volume and process ROE are high, but diagnosis complexity is low and octant 810 where diagnosis complexity is high, but patient volume and process ROE are low, the load factor is such that the healthcare provider may benefit from finding flexible resources to offload tasks the healthcare provider would otherwise have to do. However, in octants 808 and 810, it may also be the case that the healthcare provider has not reached his or her personal limit capacity and therefore does not require additional assistance from flexible resources. In octant 812, where process ROE and diagnosis complexity are high, but patient volume is low, the load factor is such that creative problem solving may be sufficient. Creative problem solving refers to a healthcare provider having to analyze a problem and use his or her skills to solve the problem. That is, the healthcare provider encountered an issue that could not be solved by a simple checklist of procedures. In octant 814, where patient volume and diagnosis complexity are high, but process ROE is low, the load factor is such that flexible resources are beneficial to provide the healthcare provider sufficient time to think about best ways to provide care so to improve process ROE. In octant 816, where patient volume, diagnosis complexity, and process ROE are high, the load factor is such that clinical surveillance coupled with IHBP and spread analysis, such as based on justification, management, and classification, will help the healthcare provider provide the best quality care.

As described above, where healthcare provisioning system 102 indicates there is an at risk task for a particular healthcare provider, healthcare provisioning system 102 attempts to offload the at risk task to a flexible resource. Alternatively, healthcare provisioning system 102 attempts to offload a different task that the healthcare provider would otherwise have to perform so as to provide the healthcare provider with additional time to perform the at risk task of greater concern or impact.

Initially the flexible resources are focused on assisting frontline caregivers and directors of the care team, such as attending physicians and charge nurses. However, because flexible resources can also reach tipping points, the tipping point analysis can be applied to anyone in the organization that may reach a tipping point that could affect organizational efficiency. Thus, indirect care and off-site resources may also be considered in a given situation.

Which flexible resources are available to assist the healthcare provider can be determined in a number of ways. For example, in an embodiment, the available flexible resources are determined by reviewing scheduling information for flexible resources. Such scheduling can be provided by a scheduling server, or any other flexible resource scheduling source to which healthcare provisioning engine 102 has access. It may also be determined by sensors (e.g., RFID) that can determine if a particular person's badge or tag is in the facility. Furthermore, it may be determined by computers processing caregiver's system access as depicted in log files. In the even supply of resources are not available in the facility, and the tasks are sufficiently fungible such that off-site flex resources can handle, the use of the tele-health and telemedicine may be employed to execute the task.

In an embodiment, scheduling data is used to predict present and future shifts of who should likely be working at any given time in the present or the future (realizing we could also add in who is present currently based on time clock punches, system log-ins, RFID, etc).

Those flexible resources that are indicated as available to assist to perform the at risk task or the task to be offloaded in a given time frame are then analyzed to determine which flexible resource is best able to handle the task. This determination can be made on a historic consideration of the potential flexible resource's experience and performance in handling similar tasks in the past as well. In addition, the potential flexible resource's own tipping points must be considered to ensure that performance of the task will not cause the potential flexible resource to reach or exceed its own tipping point threshold.

Another method for assigning flexible resources is by analyzing various spreads. The spreads are a form of gap analysis that determine what problems (or gaps) exist, and what flexible resources are best able to fill those gaps. Examples of such spreads include TIMSA spreads, JMC spreads, POA complexity spreads, and technical analysis spreads. TIMSA spreads look for Time, Information, Motivation, Skill and Authority of the healthcare provider. JMC spreads look for the Justification, Management and Classification of a process to determine what action needs to be taken. POA Spreads look for discrepancies between admission diagnoses or symptoms "Present on Admission." Technical analysis spreads are described in Veluswamy, Ragupathy, "Golden Nuggets: Clinical Quality Data Mining in Acute Care," Journal of the Physician Executive (May-June 2008).

In an embodiment, building a model of actions, timing, and outcome performance can be done using nurses notes, staffing data, and key sentinel event data. If there are no clearly, cleanly assignable actions and outcomes to a person, or there are multiple levels of attribution to an action or outcome, in an embodiment, they can be assigned using expected values based on when and where they worked, and the tasks at that time and place, relative to workers at the same time and place that may have also been involved, and thus proportionately allocated in terms of the good and bad actions probability and outcomes. This in effect creates a risk profile for the caregiver to be taken account in the model's recommendations.

Further, in an embodiment, flexibility of staff can be determined by looking at past staffing assignments, the movement in time and place, and the performance during those moves. This can be used to derive the best flex resources to try to re-allocate tasks to given that they have been flexible and also well-performing (both in terms of the actions they perform as well as in terms of how well the overloaded caregivers perform when the flex resource person is assigned solo or in a team) to serve as support to overloaded caregivers.

By assigning flexible resources as described above, the best person for a particular task may not be assigned to that task. Although this may seem counterintuitive, it is not. If that person who is normally best at a particular task has reached a tipping point, as previously described, their performance suffers substantially. Whether the person is tired or has lost concentration, as a result of reaching the tipping point, that person may no longer be the best person for the task. Consequently, embodiments may assign flexible resources in a counterintuitive manner, but achieve far greater results in terms of efficiency and cost reduction. One example to consider is the highly recognized or popular doctors that have high volumes of patients, but poorer outcomes in terms of key quality metrics than their less busy peers.

In step 404, the initial predictive healthcare supply model is modified using real-time clinical surveillance data related to healthcare supply. For example, in an embodiment, clinical surveillance related to healthcare supply includes monitoring a healthcare provider's workload (healthcare tasks based on patients, or any other work directly or indirectly related to patient care, including administrative work) to determine if his or her tipping point has been reached. There may also be instances where personal issues confronting the caregiver can be consuming "cognitive cycles" of the caregiver's mind, and can be incorporated into the load calculations, based on real-time sensory information for the caregiver, or instead the mining of data from requests given for time off, or request off patterns, or even information obtained by supervisors relating to illnesses in family, personal matters, etc. Ultimately, the method is trying to anticipate the cognitive capacity based on past metrics of where the tipping point occurs in terms of outcome, relative to cognitive consumption of where the caregiver is at any given moment.

In an embodiment, initially, the complexity load factor for each patient can be approximated, if mortality rates for the facility are not available, and the facility policy wants to avoid looking at mortality rates of others, by looking up from expected length of stay (e.g., "AMLOS") data. The lookup can be to any database having the data, including for example, a Medicare table, a healthcare facility, a health information exchange, etc. and summing the LOS for all of the diagnoses. In addition, the diagnosis ("Dx") pattern (e.g., Congestive Heart Failure-Acute Renal Failure-Arrhythmia) is stored. In an embodiment, an analysis of retrospective claims data is performed to determine the top 20 diagnoses that lead to the most cost and quality problems in the healthcare facility, such as complications, LOS overages, Resource Utilization, etc.

Cost problems can be estimated and predicted by comparing Actual LOS data to Arithmetic Mean Length of Stay ("AMLOS") for each predicted diagnoses to see if there was an overage. Further, quality can be estimated by looking at the LOS of the principal diagnosis, then seeing which International Classification of Diagnoses ("ICDs") in the secondary diagnoses of the patient had an AMLOS over the AMLOS of the principal diagnosis, indicating the patient may have developed a more serious illness during the hospital stay versus the condition, after study, actually brought them to the hospital.

For example, in an embodiment, overall complexity is estimated by analyzing diagnoses with AMLOS values exceeding 5 days, and then summing their AMLOS values to get a complexity score. This provides an estimate of overall complexity of patient relative to serious diagnoses that have greater chance of mortality. That is, because the length of stay for the healthcare provider is longer than expected, this indicates that the healthcare provider is not performing optimally because he or she is not able to discharge patients when expected. This indicates that the cases are more complex for some reason, for example, additional diagnoses and inefficient handling thereof that are contributing to the longer than expected stay. Thus, while it is likely that the healthcare provider is capable of performing adequately if not over-stressed, the increasing AMLOS indicates that the healthcare provider has become overwhelmed, either because of additional diagnoses outside of his or her specialty or that a number of patients have had multiple comorbid conditions and/or complications at or near the same time.

Figure 10:
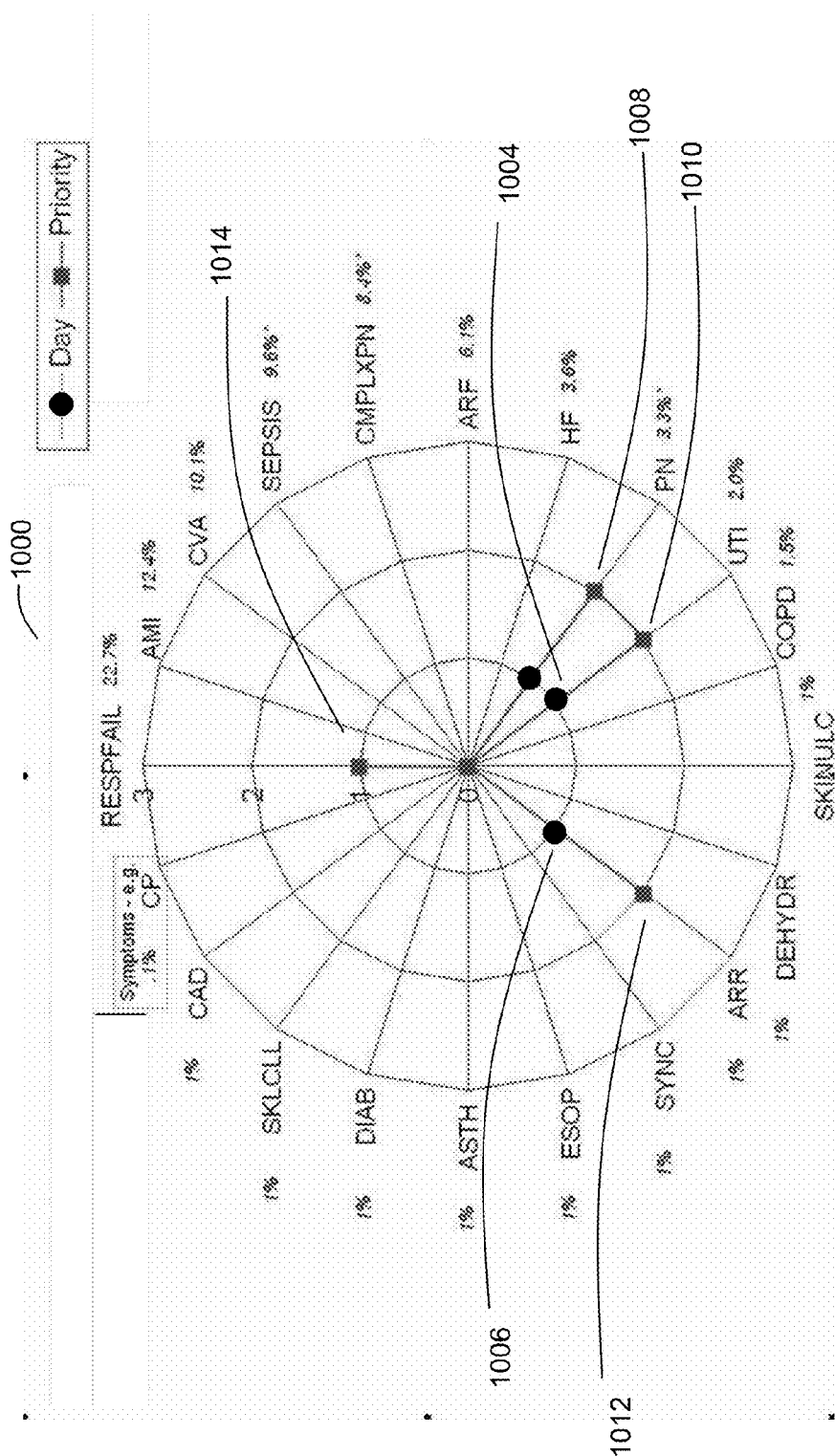
FIG. 10 illustrates an exemplary mortality risks radar 1000 according to an embodiment.

Another measure of complexity can be determined using a "mortality risks" radar. FIG. 10 illustrates an exemplary mortality risks radar 1000 according to an embodiment. Mortality radar 1000 is created and stored electronically in a memory for use in operation of an embodiment, as described herein.

Along the outer edge of mortality risks radar 1000 are diagnoses that might be seen for a patient typically seen by the healthcare provider. Shown in FIG. 10, for example, are heart failure ("HF"), acute renal failure ("ARF"), pneumonia ("PN"), and urinary tract infection ("UTI"). Any set of diagnoses can be used in a mortality-risks radar. For example, in an embodiment, the 20 most common diagnoses for a particular healthcare system are used.

Associated with each diagnosis is a mortality rate. The mortality rate is indicative of the likelihood a patient will die due to having the particular disease diagnosed. Mortality rates for various diagnoses can be obtained from databases of national mortality rates. Alternatively, the healthcare system may have compiled its own mortality data that can be used. The healthcare system can be a hospital, a city-, county-, state-, region-, country-, or world-wide healthcare group, or any other scope in size.

In an embodiment, the diagnoses are positioned around the outer edge of the mortality risks radar in clockwise descending order. In a sense, mortality risks radar is an indication of the preoccupation and "worry" that a healthcare provider will have with a particular patient. The more complex, the more likely the healthcare provider will be to be preoccupied with that patient, and, as a result of this cognitive load to ensure the patient survives, the likelihood of not performing other tasks increases as the tipping point is reached and tasks are either forgotten that were alerted or reminded along the way, or experience stored deep in memories are not remembered fast enough due to limited cognitive capacity constraining creative problem solving for this caregiver's patients.

In the embodiment illustrated in FIG. 10, mortality rates are provided in both timing and priority. Other measures of mortality can be used in a given embodiment. In an embodiment, a higher priority is indicated by closer proximity to the center or mortality radar 1000. That is, the closer to the center a particular dot is, the more likely that diagnosis will be observed in the patient, which is intuitive when thinking of a radar (closer to the center, the nearer the threat is).

Mortality risk radar 1000 illustrates a pattern for an exemplary patient that may have been admitted to a healthcare facility. Time in the exemplary pattern shown in FIG. 10 is illustrated by dots 1002, 1004, and 1006 corresponding to diagnoses pneumonia ("PN"), urinary tract infection ("UTI"), and arrhythmia ("ARR") respectively. Priority in the exemplary pattern shown in FIG. 10 is represented by dots 1008, 1010, 1012, and 1014 corresponding to diagnoses PN, UTI, ARR, and respiratory failure ("RESPFAIL"), respectively.

In operation, to determine a complexity load factor using mortality risks radar 1000, the healthcare provisioning engine 102 begins in the center and proceeds around the radar looking for dots. In an embodiment, the system maintains a running sum of mortality rate for each diagnosis having a dot encountered. In an embodiment, the system maintains a running sum of mortality rate for each priority dot encountered. In an embodiment, the priority running sums are themselves summed to arrive at a complexity load factor for a particular patient.

In an embodiment, the healthcare supply model includes the AMLOS for each patient cared for by a healthcare provider as well as the mortality risk radar score determined for each patient cared for by a healthcare provider. These measurements of complexity load give an idea of the demand being placed on the healthcare provider at a given point in time. As a result, the AMLOS over a patient load and/or the mortality radar scores along with evaluation of the healthcare provider's performance in the past under similar complexity loads can be a good indication of whether the healthcare provider has reached, or is about to reach, a tipping point. For example, indications of when a tipping point is being reached or exceeded by a healthcare provider include increasing Resource Utilization ("RU"), LOS for a healthcare provider, increased readmissions for patients seen by the healthcare provider, or any other performance measure that can indicate decreasing performance. Any other measures of healthcare demand in addition to LOS and mortality radar can be analyzed and used as input to healthcare provisioning engine 102 in an embodiment as well.

Figure 13:
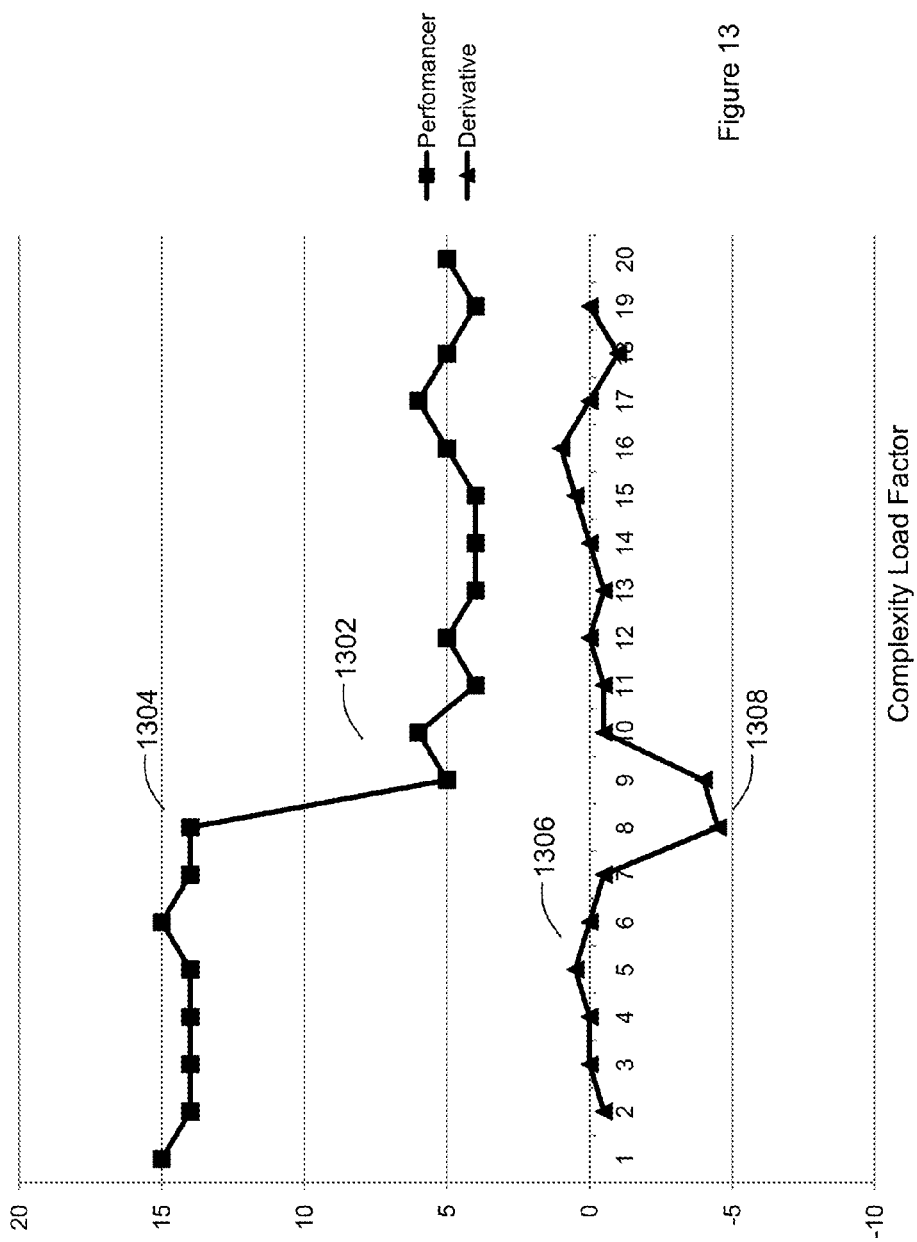
FIG. 13 illustrated graphically calculation of a tipping point according to an embodiment.

In an embodiment, tipping point can be determined by considering a correlation of complexity load factor with performance. A tipping point occurs where the performance curve shows an inflection point. This can be computed as a derivative (negative in this case) that exceeds (falls below) a particular threshold. FIG. 13 illustrated graphically calculation of a tipping point according to an embodiment. Curve 1302 is an exemplary performance versus complexity load factor curve for a particular healthcare provider. Looking at curve 1302, one can "eyeball" where the inflection point indicative of a tipping point is at point 1304, which corresponds to a complexity load factor of 8. Computationally, in an embodiment, the tipping point can be determined by computing the derivative of the healthcare provider's performance curve and finding the maximum negative rate of change in performance. Curve 1306 is a derivative of the exemplary performance curve 1308. As shown in curve 1306, the maximum negative rate of change in performance occurs at point 1308, which also corresponds to a complexity load factor of 8. Thus, in this case healthcare provisioning engine 102 would begin to assign flexible resources to assist the healthcare provider, when the complexity load factor for the healthcare provider reached 8. The complexity load factors used in the correlation can be for all patients treated by a healthcare provider or a subset based, for example on diagnosis pattern. Any other method for determining an inflection point can be used, including, without limitation, second derivatives and second derivatives in combination with first derivatives.

For newly admitted patients, the AMLOS and mortality risk radar measurements can be used to determine which tasks are likely to be required to be completed. That is, using scheduling information and complexity load estimates for available healthcare providers, the system can assign the newly admitted patient to a healthcare provider that is likely to be able to handle the additional complexity load exhibited by the newly admitted patient (e.g., perform the required tasks) without reaching a tipping point. If none are available, healthcare provisioning engine 102 can search for a healthcare provider to satisfy the demand by offloading of other tasks that would otherwise have to be performed by the healthcare provider. Alternatively, healthcare provisioning engine 102 can assign the task to be completed to a flexible resource.

For already admitted patients, the AMLOS and mortality risk radar measurements can be used to determine whether a healthcare provider has reached, or is likely to imminently reach, a tipping point. If a tipping point has been, or is about to be, reached, the system can consult scheduling information available to it to help offload tasks that the overloaded healthcare provider may not have to perform, or that can be better performed by someone else. That is using the scheduling information, the system can find a flexible resource to which to offload tasks that would otherwise have to be performed by the overloaded healthcare provider to a flexible resource better able to handle the task. Alternatively, healthcare provisioning engine 102 can assign the task to be completed to a flexible resource.

Figure 9A:
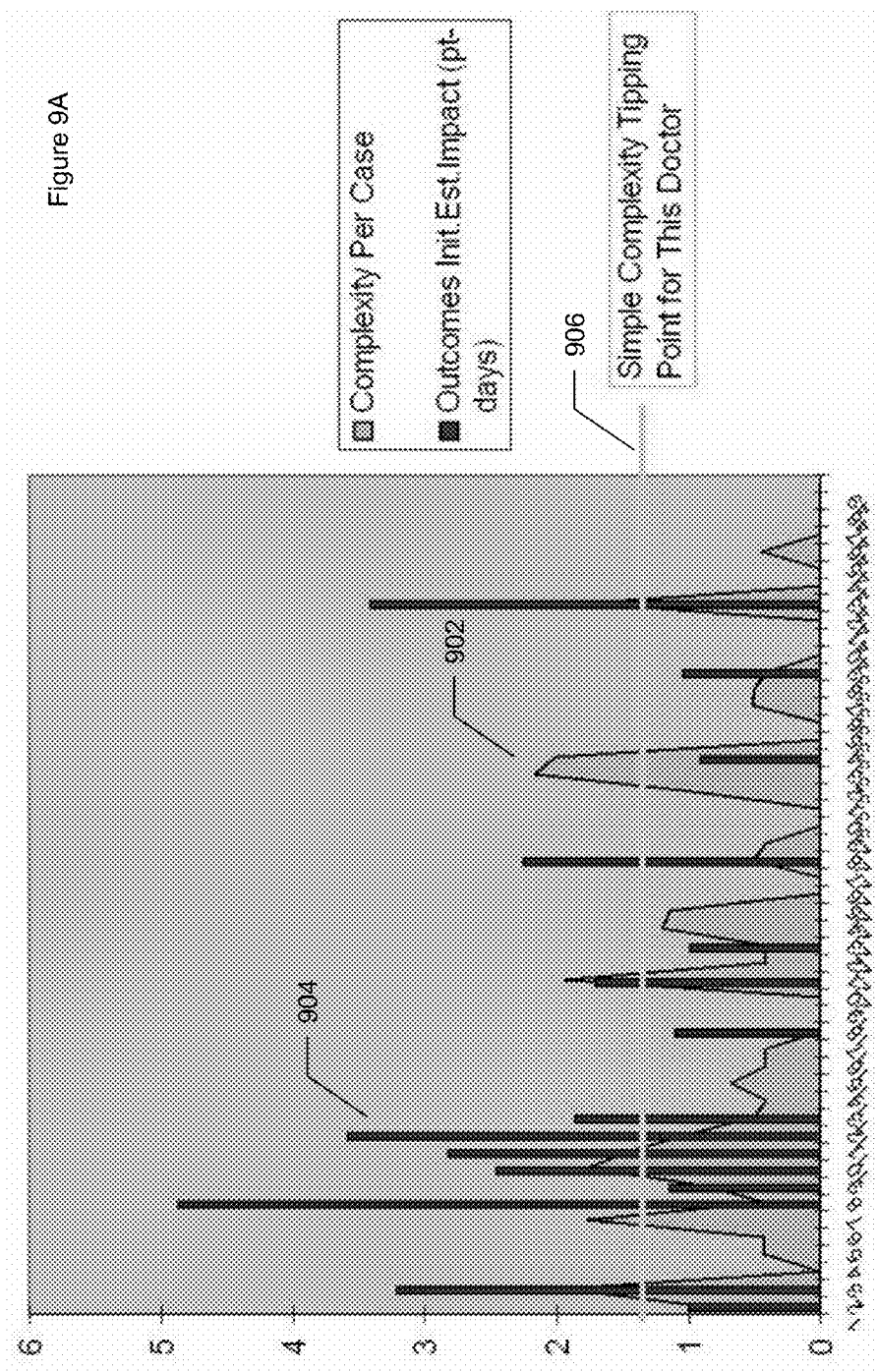
FIG. 9A illustrates complexity load factor viewed from a diagnoses per patient perspective.

Complexity load factor can be viewed from a number of perspectives that can be used to estimate a tipping point for a healthcare provider. For example, FIG. 9A illustrates complexity load factor viewed from a diagnoses per patient perspective. Curve 902 indicates complexity load factor in terms of diagnoses per patient for a number of patients. In the example of FIG. 9A, the healthcare provider is responsible for 49 patients. Each patient has a complexity seen as the diagonal "peaks" in the background, where the higher the peak, the greater the complexity. Vertical bars such as vertical bar 904 represent an estimate of impact of complexity in terms of overage days of such problems for a particular patient for a particular day. FIG. 9A also illustrates the simple complexity tipping point 906 for this exemplary doctor for this exemplary patient load. In the example of FIG. 9A, an intervention is indicated as required for a patient where a horizontal bar rises above simple complexity tipping point 906.

FIG. 9B illustrates complexity load factor viewed from a diagnoses per day perspective. The view for the period can be per day or per any other time period. In this manner, the complexity load factor is viewed as "clustered" patients of a given complexity in a given time period, and can provide alternate information as to when a tipping point is approaching or has been reached. Such a tipping point is termed a total diagnosis complexity ("TDC") tipping point. Curve 910 indicates total diagnosis complexity each day for a number of patients. Vertical bars such as vertical bar 912 represent an estimate of impact of complexity in terms of overage days of such problems for all patients for a particular day. FIG. 9B also illustrates the TDC tipping point 914 for this exemplary doctor for the exemplary patient load. In an embodiment, an intervention is indicated as required where a horizontal bar rises above TDC complexity tipping point 914. That is, the tipping point for the healthcare provider for a given day is predicted where the vertical bar exceeds the TDC tipping point.

The data in FIGS. 9A and 9B are example of healthcare demand data. That is, FIGS. 9A and 9B represent examples of how patient complexity affects the likelihood of reaching a tipping point.

FIG. 9C illustrates an example of considering how healthcare supply affects tipping point. Shown in FIG. 9C is an example of preoccupation risk growth ("PRG"). PRG estimates how much a healthcare provider is essentially distracted or preoccupied due to complexity load. Curve 920 illustrates daily PRG estimates over a given time period. PRG estimates can be daily or some other time period. Curve 924 represents daily estimate of TDC as described above with respect to curve 910 in FIG. 9B. Vertical bars such as vertical bar 926 represent an estimate of impact of complexity in terms of overage days of such problems for all patients for a particular day. FIG. 9C also illustrates the PRG risk tipping point 928 for this exemplary doctor for this exemplary patient load. In an embodiment, an intervention is indicated as required where a horizontal bar exceeds TDC tipping point 928.

In an embodiment, both healthcare demand complexity load factors and the effects such complexity load factors have on healthcare supply are analyzed. This results in a better prediction of when a tipping point is actually reached for a particular healthcare provider and therefore, a better indicator of when an intervention is required. For example, comparing FIGS. 9A and 9C, it can be seen that all but one of the vertical bars that indicate an intervention is required cross PRG risk tipping point 928 in FIG. 9C, whereas less than of the vertical bars that indicate an intervention is required cross simple tipping point 906 in FIG. 9A, which is based only on demand for healthcare services. Thus, considering the effect of healthcare demand complexity load factors can add significantly to the efficiency of embodiments.

Using overall complexity estimated in this manner can provide a cost measure for the patient that can be used to extrapolate other cost measures (including resource utilization). Further, overall complexity estimated in this manner is an indicator of quality problems that that can be used to extrapolate other quality problems (including complications, unexpected mortality, core measure performance, etc.). This provides what diagnoses are involved in a predictive model, and what consequences there could probably be, and the probable impact they could have, for patients confronting similar situations (e.g., the attention level that must be given to patient given their likely demands, as well as other items relating to supply such as this attending physician based on their specialty or practice pattern—or tipping points).

While complexity is an important factor in predicting healthcare cost and quality problems, it is not the only one. As a result, predicting healthcare supply based solely on complexity may lead to false positives (predicting a problem when there is no problem) and false negatives (not predicting a problem when there is a problem). False positives may result in unnecessarily burdening healthcare providers to perform services that are not required because there is no problem. False negatives can result in serious cost overruns or detriment to patient safety where services are not provided, though required.

As a result, it is important to determine not just the degree of overload for a healthcare provider, but also the type of load that is causing the overload. For diagnoses patterns where failure to predict successfully can be catastrophic, embodiments strive to avoid false negatives. For less severe diagnosis patterns, embodiments strive to avoid false positives. So, if a patient follows a diagnosis pattern which direct care resources are familiar and comfortable, then creative problem solving, to think of tasks that may apply in situations that are not found in the standard order sets or checklists but can lead to much better outcome given the relatively unique situation of a complex case, is done faster. If, on the other hand, direct care resources are not familiar with the complexity diagnosis pattern, then IHBP can serve as a useful guide. In that case, process adaptation can also help to reduce process and work flow disruption. Further, those flexible resources that are familiar with the particular complexity diagnosis pattern can complement the direct care resources, even if to simply digest all critical details and prior data to reduce skimming and multitasking needed. This approach helps reduce overload from alerts and reminders relating to a particular combination of diagnoses (diagnosis complexity pattern) in the complexity profile of a patient.

Further, in an embodiment, additional monitoring is performed using devices such as biometric sensors of stress or fatigue, especially mental fatigue, or if those are not available, at least cameras and microphones to capture visual and audio information that can help estimate capacity risk, and therefore whether a tipping point has been reached, of a particular healthcare provider. For example, this can include looking at facial expressions, yawning, nodding off, etc., to determine whether a healthcare provider has reached a tipping point that will affect his or her ability to provider healthcare services. An example of such facial expression analysis is being performed using RUBI (Robot Using Bayesian Inference) at UC San Diego's Machine Perception Lab to determine whether a particular healthcare provider is nearing or has exceeded a tipping point. Other clinical data related to healthcare supply can be monitored and used to update the initial healthcare supply model. The generated healthcare supply model can be used to predict healthcare supply available to satisfy healthcare demand.

Further in an embodiment, a robot can be used to obtain the desired information. Using RFID and/or other techniques, instructions and tracking information can be issued and/or received from the robot to direct the robot to the proper place for obtaining required information. For example, the robot could be directed to a particular area in a healthcare facility to obtain photographs of an attending healthcare provider to offer further data that can help determine whether the healthcare provider is approaching or has crossed a tipping point based on movement patterns, speed of activity, or various behavior changes.

In an embodiment, additional real time information can be obtained through additional sensor devices to detect information that can be used to predict whether a healthcare provider is nearing, or has reached, a tipping point. For example, in an embodiment, biometric sensors can be embedded in the healthcare providers clothing. The biometric sensors can make measurements of the healthcare provider's pulse rate, breathing rate, perspiration, etc. These measurements can be compared to previously stored measurements to obtain a real time estimate of the healthcare provider's stress level. This stress level, by itself, or in conjunction with complexity load analysis as described above can be used to determine whether the healthcare provider is nearing or has exceed a tipping point.

Figure 6:
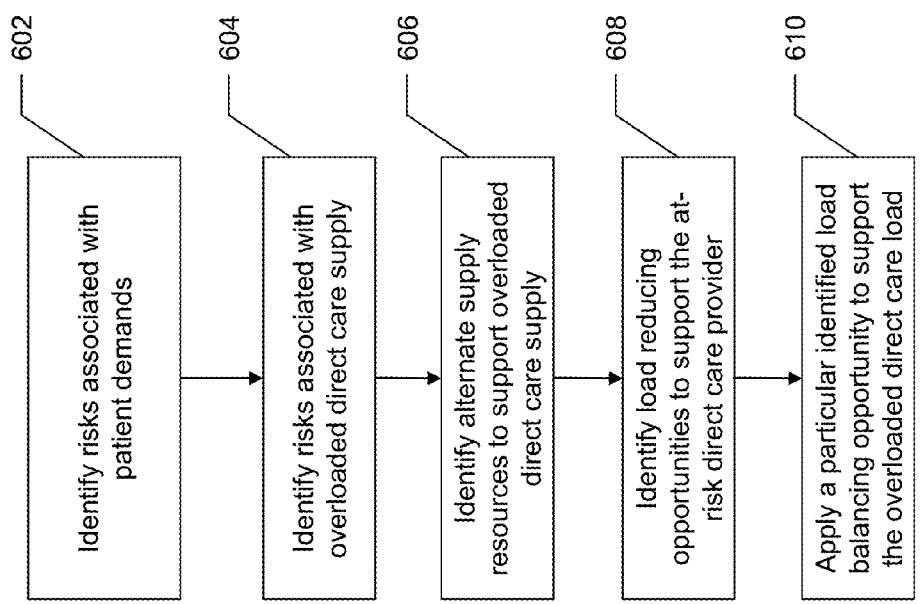
FIG. 6 is a flow chart for a method of supporting an overloaded direct care provider using alternate supply to meet healthcare demand according to an embodiment.

FIG. 6 is a flow chart for a method of supporting an overloaded direct care provider using alternate supply to meet healthcare demand according to an embodiment. In step 602, risks associated with patient demands are identified through complexity analysis. In step 604, risks associated with overloaded direct care supply are identified using tipping point technical analysis. In step 606, alternate supply resources are identified that can be used to support the overloaded direct care supply. In an embodiment, this can be accomplished using process mining of TIMSA to identify "touchpoints" that consume job performance capacity. In step 608, load reducing opportunities are identified to support the at-risk direct care provider. In an embodiment, this is accomplished using a meta-level manager similarity based learning ("SBL") for process adaptation. The meta-level manager analyzes the cross terrain of the objective function of the model that is in need of improvement. A learning mechanism can be used to improve predictions over time. For example, the metal-level manager could apply gradient descent or simulated annealing for a hilly cost terrain model function or a genetic algorithm for a pot marked but relatively flat cost terrain model function. In an embodiment, SBL is used as the learning mechanism because it learns with fewer learning examples than a neural network. Moreover, an SBL is more flexible as it is not bound by limiting rules as with an expert system. In step 610, a particular identified load balancing opportunity using flexible resources is applied to support the overloaded direct care load. In an embodiment, this load balancing and JMC/other spreads (as well as identifying and helping guide workflow) provides orders of magnitude returns. The returns are on the tasks required and to accomplish the order of magnitude return derived by doing these returns is accomplished by reallocating flexible resources towards different tasks or redistributing tasks to different flexible resources.

Flexible resources can be notified of the need to perform a particular task in a number of ways. For example, once healthcare provisioning engine 102 has determined which resources to assign to which tasks, healthcare provisioning engine 102 can prepare a daily activity plan for each affected healthcare provider that identifies the task(s) that healthcare provider must perform and when they need to be accomplished. Once prepared the daily activity plan can be distributed to the affected healthcare providers in any known manner, including for example, by handout, email, letter in employee mailbox, or any other known manner.

Further, in an embodiment, up to real time adjustments based on tipping point can be made. Flexible resources to be assigned on a real time or near real time basis can be notified of the tasks to complete by telephone call, text, email, etc. to device that can receive the notification. Exemplary such devices are smart devices such as smart phones and tablets, such as the Apple iPad tablet.

Figure 7:
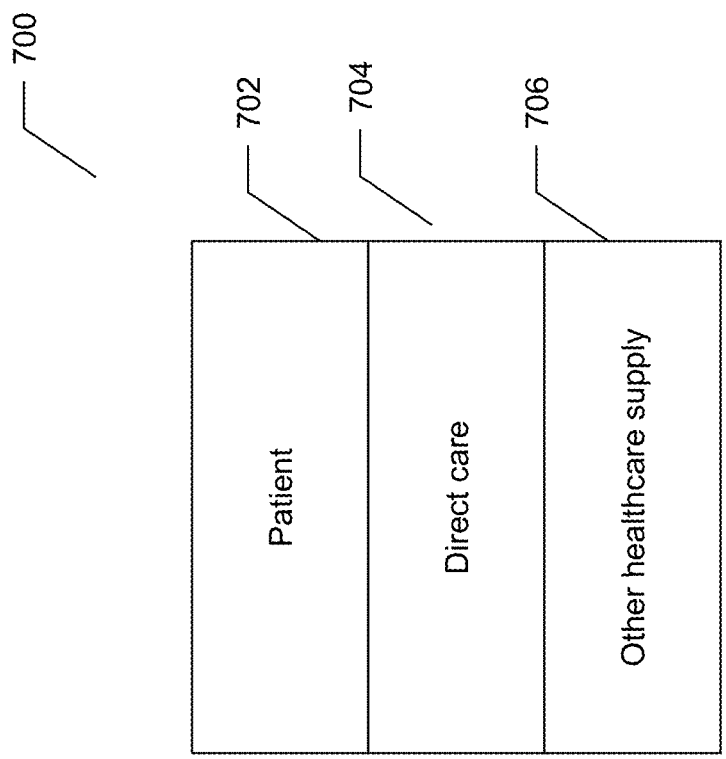
FIG. 7 illustrates a healthcare provisioning hierarchy to help explain how direct care load is assisted by an embodiment.

FIG. 7 illustrates a healthcare provisioning hierarchy 700 to help explain how direct care load is assisted by an embodiment. In an embodiment, direct care load is part of healthcare provisioning hierarchy 700 where a patient 702 is at the top, direct care providers 704 are underneath patient 702. Direct care providers 704 are directly responsible for providing healthcare to patient 702. All other healthcare supply 706, i.e., flexible resources, available for providing healthcare to patient 702 fall under direct care providers 704. In an embodiment, it is desirable to want to push lesser valued tasks (that deal with risks) down healthcare provisioning hierarchy 700. In an embodiment, this is accomplished by load balancing healthcare supply as described above.

Figure 5:
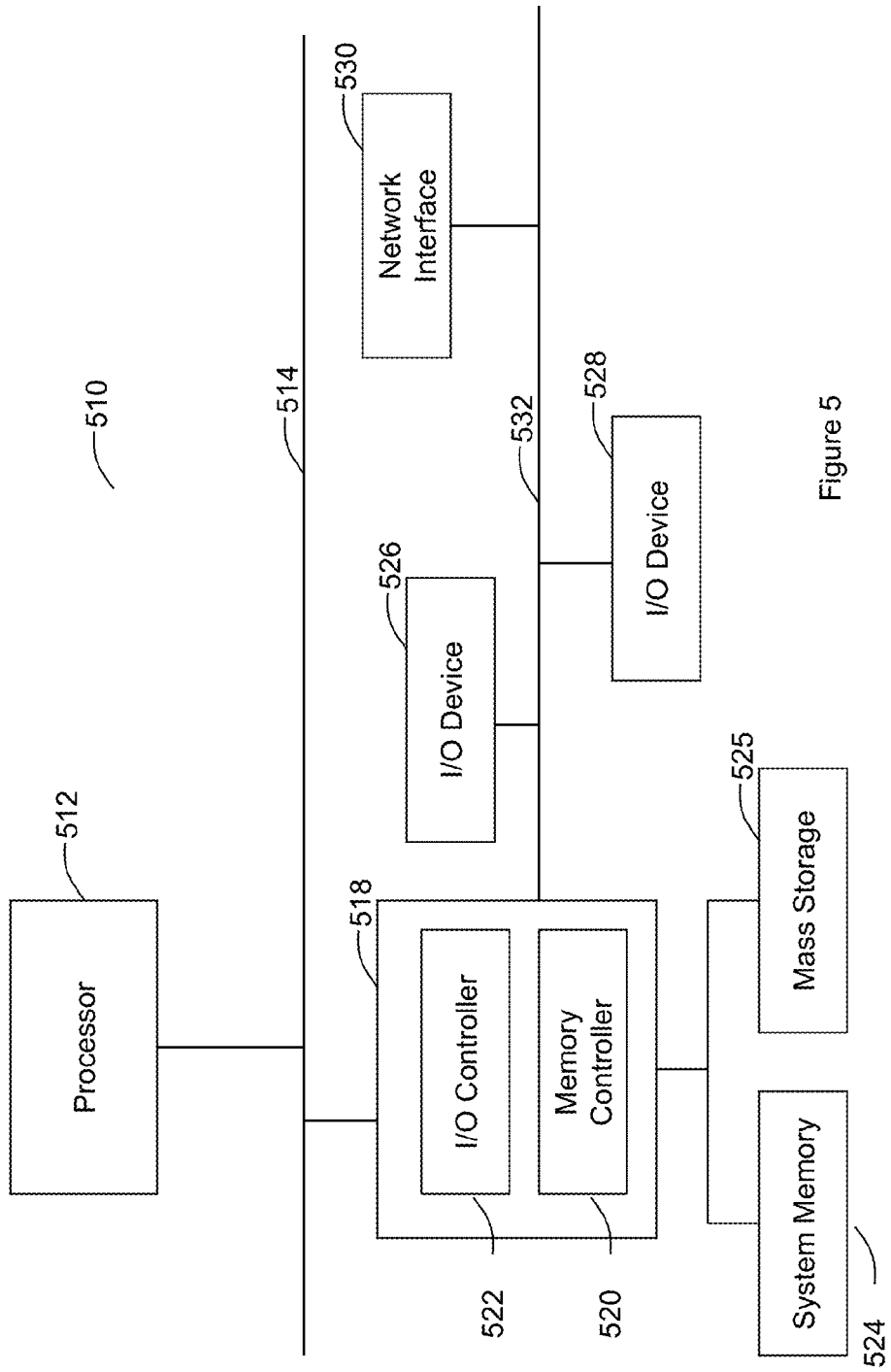
FIG. 5 is a block diagram of an example processor system that may be used to implement the apparatus and methods described herein according to an embodiment of the present invention.

FIG. 5 is a schematic block diagram of an example processor system 510 that may be used to implement the apparatus and methods described herein. As shown in FIG. 5, processor system 510 includes a processor 512 that is coupled to an interconnection bus 514. Processor 512 may be any suitable processor, processing unit or microprocessor. Although not shown in FIG. 5, system 510 may be a multi-processor system and, thus, may include one or more additional processors that are identical or similar to processor 512 and that are communicatively coupled to interconnection bus 514.

Processor 512 of FIG. 5 is coupled to a chipset 518, which includes a memory controller 520 and an input/output ("I/O") controller 522. As is well known, a chipset typically provides I/O and memory management functions as well as a plurality of general purpose and/or special purpose registers, timers, etc. that are accessible or used by one or more processors coupled to the chipset 518. The memory controller 520 performs functions that enable the processor 512 (or processors if there are multiple processors) to access a system memory 524 and a mass storage memory 525.

System memory 524 may include any desired type of volatile and/or non-volatile memory such as, for example, static random access memory ("SRAM"), dynamic random access memory ("DRAM"), flash memory, read-only memory ("ROM"), etc. The mass storage memory 525 may include any desired type of mass storage device including hard disk drives, optical drives, tape storage devices, etc.

The I/O controller 522 performs functions that enable the processor 512 to communicate with peripheral I/O devices 526 and 528 and a network interface 530 via an I/O bus 1332. I/O devices 526 and 528 may be any desired type of I/O device such as, for example, a keyboard, a video display or monitor, a mouse, etc. Network interface 530 may be, for example, an Ethernet device, an asynchronous transfer mode ("ATM") device, an 802.11 device, a DSL modem, a cable modem, a cellular modem, etc. that enables processor system 510 to communicate with another processor system.

While memory controller 520 and I/O controller 522 are depicted in FIG. 5 as separate blocks within chipset 518, the functions performed by these blocks may be integrated within a single semiconductor circuit or may be implemented using two or more separate integrated circuits.

Using the embodiments of the present invention, inefficiencies in conventional healthcare provision are reduced. The reduction in inefficiency prevents crisis in time, and can dramatically improve performance in healthcare provision. As a result, patient outcomes are improved, and healthcare costs are reduced.

Following is an exemplary embodiment applied to task management to improve healthcare provisioning for a very ill patient with a complex diagnosis. Based on diagnoses and level of urgency for the diagnoses, healthcare resource usage can be estimated and what tasks are required to be performed to care for the patient.

Based on the healthcare resource usage estimate and required tasks, certain tasks may be considered at risk. These "weak links" are potential sources of process breakdown points. These overloads and consequent TAR are also at least bottlenecks in workflow—slowing things down as they also lead to more errors. To determine this risk, in an embodiment, tasks in past, present, and future are considered, so thus overload analysis is important to determine risks from historical data and also current data from various systems and sources, to then use to create predictive models and concurrently solve. Using this information, the healthcare provisioning system determines possible tipping points for providers responsible for providing care to the patient. The complex diagnosis patterns ("CDPs") that affect a particular healthcare provider are used to help determine the complex task patterns ("CTPs") that affect the healthcare provider's performance as described above.

To improve accuracy of the tipping point estimation and thus improve the decision-making concerning how to handle tasks that may be at risk, real-time clinical surveillance related to healthcare supply is performed. In an embodiment, such real-time clinical surveillance related to healthcare supply is performed using devices like cameras and microphones to capture visual and audio information that can help estimate capacity risk. In an embodiment, this can include looking at facial expressions, such as being done using RUBI (Robot Using Bayesian Inference) at UC San Diego's Machine Perception Lab.

Based on the tipping point analysis, the healthcare provisioning system provides a recommendation for caring for the patient to avoid reaching tipping points. For example, the healthcare provisioning system will consider what alternate resources are available that have not reached their tipping point that may be available to care for the patient. In addition, the healthcare provisioning system will consider how well those resources have performed in the past. The result will be the resources estimated to be the most cost-effective uses of time, resources, and capacity flexibility.

The recommendation will result in offloading up or down. In offloading down, non-critical path, low priority tasks for the entity with tasks at risk are delegated to other resources. The other resources can be notified in a number of ways, including text message, smartphone email, and passive or active means. In offloading up, a healthcare resource is reinforced or replaced to avoid risk to high-priority tasks or tasks on a critical path.

In an embodiment, healthcare provisioning system 102 can be viewed as a healthcare grid that is employed to help identify and avoid such tipping points. In an embodiment, the healthcare grid uses predictive healthcare modeling on a telehealth platform to simulate potential problems and their solutions. A machine learning process adaptation aids in determining solutions. The healthcare grid moves healthcare supply along the healthcare grid to meet healthcare demand. In an embodiment, process arbitrage is used to provide clinical load balancing. Such clinical load balancing and helps manage flexible resources to maximize comparative advantage, and thus, efficiency. In an embodiment, the healthcare grid uses precognition of healthcare supply and demand issues, at various levels of granularity (global, regional, provider, or patient), to maximize effectiveness of planning. In summary, the healthcare grid offers solutions to avoid micro-overloads and macro-overloads that cause preventable deaths and preventable costs.

Figure 14:
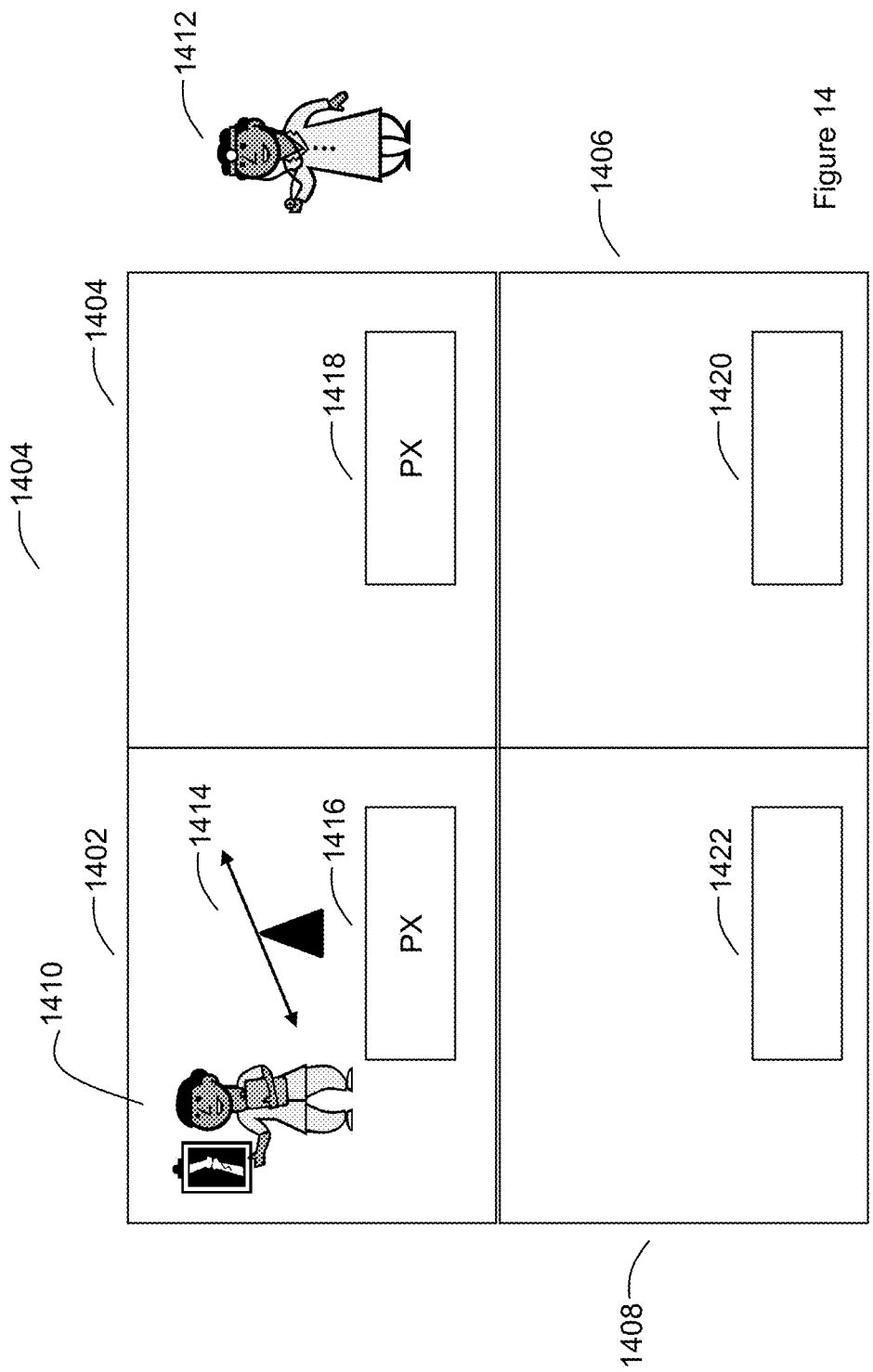
FIG. 14 illustrates an exemplary such control panel 1400 according to an embodiment.

In an embodiment, healthcare provisioning engine can provide a control panel for viewing all or a portion of a healthcare facility and whether doctors, nurses, or other caregivers, are reaching tipping points. FIG. 14 illustrates an exemplary such control panel 1400 according to an embodiment. Screen 1400 illustrates an exemplary floor of a healthcare facility. The floor includes rooms 1402, 1404, 1406, and 1408. Control panel 1400 illustrates that rooms 1402 and 1404 have beds 1416 and 1418 respectively that are occupied by patients. Rooms 1406 and 1408 have beds 1420 and 1422 that are unoccupied.

A healthcare provider 1410 is attending the patient in room 1416. Healthcare provisioning engine 102 can obtain this information via an RFID tag having a unique identifier to identify healthcare provider 1410 that worn by healthcare provider 1410. The RFID tag is sensed by a sensor in room 1402, which identifies healthcare provider 1410 as being in the room. The information can be transmitted to healthcare provisioning engine 102 in any of a number of ways. Other ways of determining which care provider may be in a room is system logon data, visual data, etc.

Also shown in exemplary control panel 1400 is a seesaw 1414. Seesaw 1414 graphically indicates whether healthcare provider 1410 is nearing or has reached a tipping point. In an embodiment, seesaw 1414 can be tipped to one side to indicate that the healthcare provider is not at a tipping point. As the healthcare provider's complexity load factor increases, the seesaw will be shown as moving toward tipping to the other side. When level, the healthcare provider has reached a tipping point. When tipped to the other side, the healthcare provider has exceeded the tipping point. Information to determine the status of seesaw 1414 is determined by healthcare provisioning engine 102 as described above.

When a healthcare provider has reached a tipping point, an audio and/or visual alert can be provided to an administrator. In addition, healthcare provisioning engine 102 will attempt to find flexible resources to assist (via offloading of some set of tasks) the healthcare provider so that the healthcare provider can be put back into a non-tipping point status. For example, if healthcare provider 1410 had reached a tipping point, and was supposed to see the patient in room 1404, healthcare provisioning engine might assign a flexible resource such as healthcare provider 1412 to see the patient in room 1404.

In addition to providing a graphical representation of a healthcare facility, screen 1410 can be used to "drill down" to find particular information. For example, an administrator can drill down to determine the diagnoses for a particular patient in a particular room, the complexity load factor on a particular physician, or any other information that is desired to be made available through control panel 1400. Further, in an embodiment, an administrator can cause a new tipping point analysis to be performed for all or some of the healthcare providers in the healthcare facility.

Thus, avoiding overloads on using a healthcare grid in an embodiment attempts to better use existing supplies or else increase supply. Increasing supply generally means using less scarce (and thus likely less costly) supply to meet demand. However, in "trading down" to increase supply in this manner requires reducing the risk of failure (which would negatively affect quality outcomes, costs, or both) of the configured supply. This is enabled by either increasing supply of flexible resources, or else extracting more "safely" out of existing flexible resources in a better, cheaper, and faster way.

Figure 12:
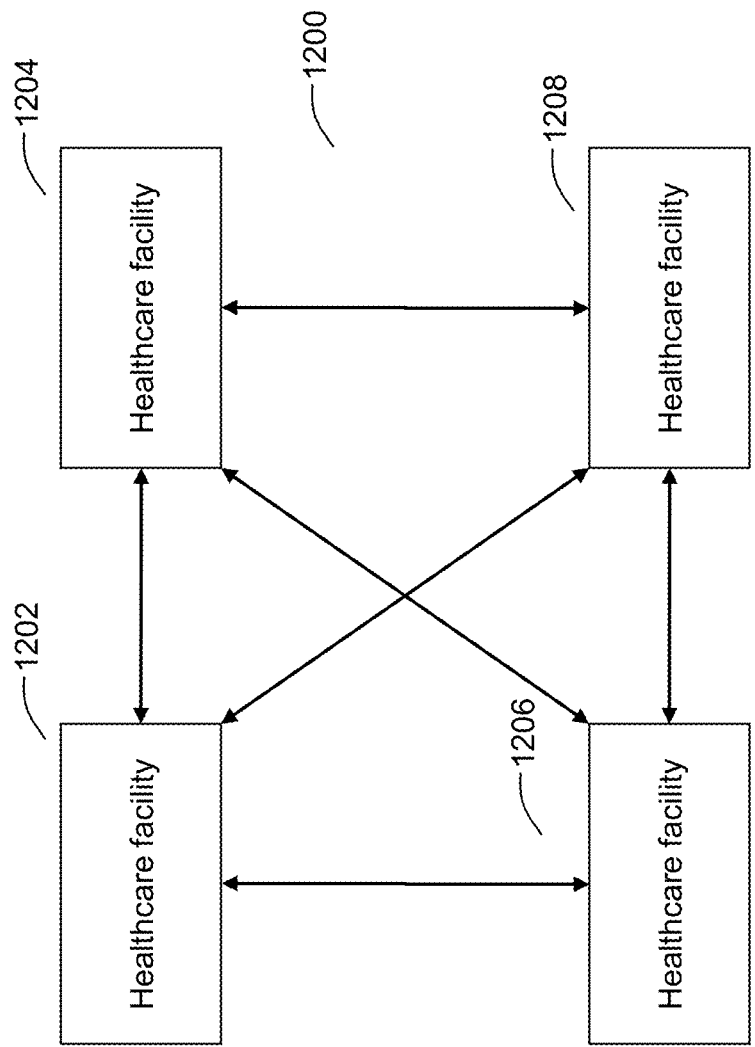
FIG. 12 illustrates an exemplary healthcare system according to an embodiment.

Embodiments of the present invention can be implemented over any scope. For example, FIG. 12 illustrates an exemplary healthcare system 1200 according to an embodiment. Healthcare system 1200 includes four healthcare facilities, 1202, 1204, 1206, and 1208. Healthcare facilities 1202, 1204, 1206, and 1208 can be any healthcare facilities, including hospitals, clinics, office, and any other healthcare facility. Each of healthcare facilities 1202, 1204, 1206, and 1208 can communicate with each other. In an embodiment, one or more of healthcare facilities 1202, 1204, 1206, and 1208 can collect and log patient data such as symptoms, diagnoses, schedules, lab reports, etc. to assist in performing the operations described above. As a result, a healthcare facility can collect data necessary to perform efficient healthcare provisioning according to an embodiment over any size, for example, city, state, region, country, world, etc.

A healthcare facility can use healthcare provisioning system 102 as described herein to assign tasks to avoid tipping points over any time frame, whether periodic or not. For example, a healthcare facility can apply healthcare provisioning system 102 once a day, twice a day, weekly, or any other time frame. There is no requirement that the time frame be periodic.

Figure 18:
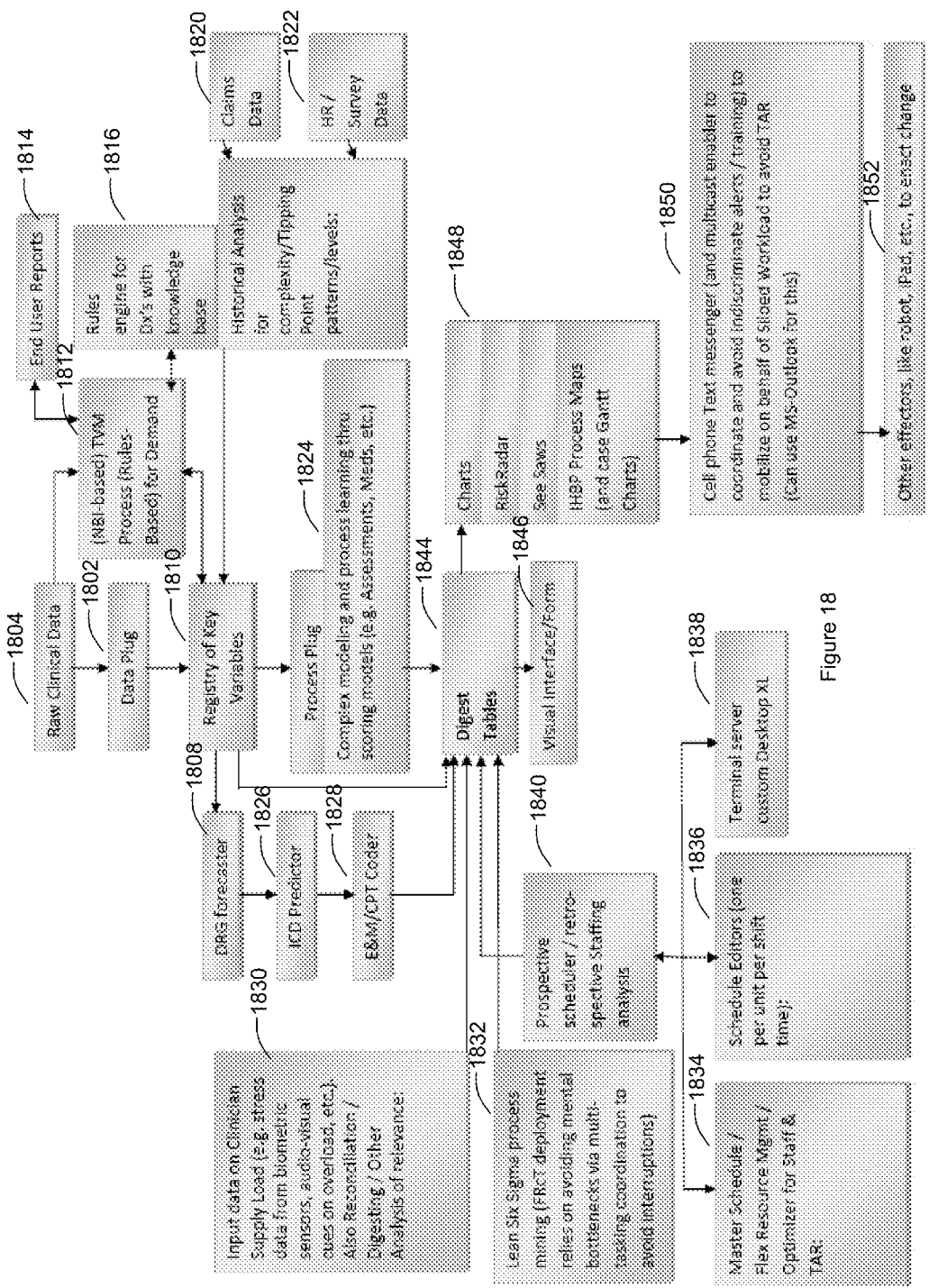
FIG. 18 is a more detailed schematic diagram of a system for providing efficient provisioning of healthcare 1800 according to an embodiment.

FIG. 18 is a more detailed schematic diagram of a system for providing efficient provisioning of healthcare 1800 according to an embodiment. Raw clinical data module 1804 inputs data from a number of sources including healthcare provider dictation, lab reports, physical examinations, etc. are input to a data plug module 1802 and translation and valuation modeling module ("TVM") 1812. TVM module 1812 provides input for an end user reports module 1814 that can prepare end user reports concerning the input data. TVM module 1812 provides input to a rules engine 1816 that is used to provide diagnoses in conjunction with a knowledge base.

Rules engine 1816 accepts inputs from a claims data module 1820 and HR survey data module 1822 to determine and make available a historic analysis of complex tipping point pattern/levels.

Data plug module 1802 provides input to a register of key variables 1810. Register of key variables 1810 includes variable names that can be used for translation and identification of diagnoses. Register of key variables 1810 provides input to diagnosis review group 1808, which, in turn provides input to ICD (international classification of diseases) predictor 1826, which provides input to E&M/CPT coder 1828. Register of key variables 1810 provides input to a process plug module 1824. Process plug module 1824, described in more detail below, provides complex modeling and process learning through scoring models (e.g., assessments, medications, etc.).

Digest tables module 1844 processes data received from a supply data module 1830, a process mining module 1832 to apply flexible resources to avoid bottlenecks through multitasking, a prospective scheduler 1840, and analyzes the data as described herein to provide output data to a visual interface 1846 (such as a computer monitor or other visual interface). Visual interface 1840 can provide charts, a risk radar, see saws, and IHBP process maps via a visual processing module 1848. Visual processing module 1848 can provide data for output to healthcare providers via text messages on a smartphone 1850 and through any other device 1852 that can provide information to healthcare providers throughout a healthcare facility to enact change. Such other devices 1852 include without limitation, iPads, robots, etc.

Prospective scheduler module 1840 obtains inputs from scheduling modules such as master scheduler 1834, schedule editors 1836, and terminal server 1838.

Figure 15:
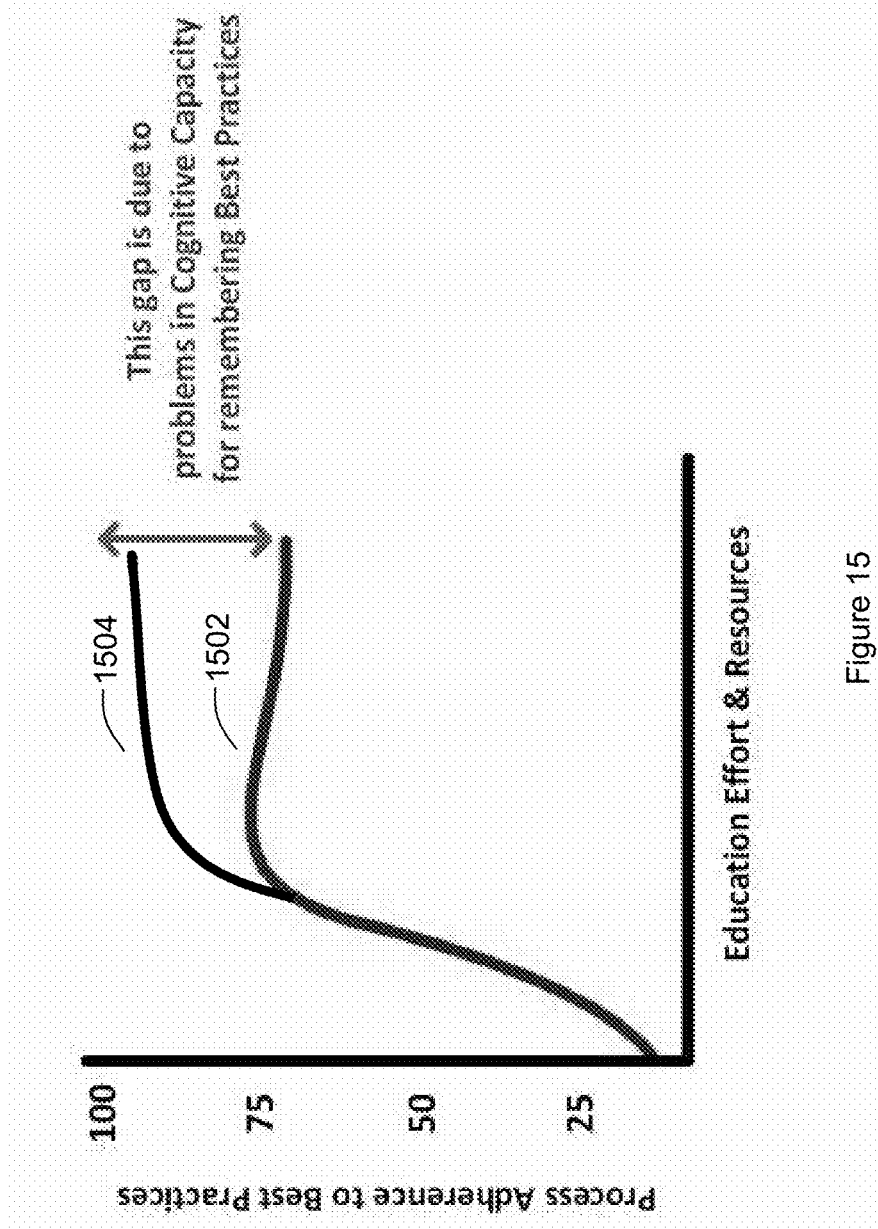
FIG. 15 is a graphical illustration of how process adherence to In House Best Practices is improved by using embodiments as described herein.

FIG. 15 is a graphical illustration of how process adherence to IHBP is improved by using embodiments as described herein. As shown in FIG. 15, a healthcare provider's adherence to IHBP is illustrated as a function of education effort and resources. Curve 1502 represents exemplary process adherence to IHBP as a function of education effort and resources without using embodiments as described herein. Curve 1502 illustrates that at a certain point, process adherence to IHBP levels off, and even diminishes. This illustrates that even with additional education efforts and expenses, process adherence to IHBP does not continue to increase.

Curve 1504 represents exemplary process adherence to IHBP as a function of education effort and resources using embodiments as described herein. Curve 1504 illustrates that applying tipping point and load balancing as described herein allows for significantly better adherence to IHBP even with the same education efforts and resources. Thus, applying tipping point analysis as described herein leads to better adherence to IHBP. Because healthcare providers adhere to IHBP with a given education effort and use of resources, the healthcare provider will be able to spend less time diverted to training. As a result, the healthcare provider will have more time to spend with patients, leading to better overall care and patient outcomes.

Figure 16:
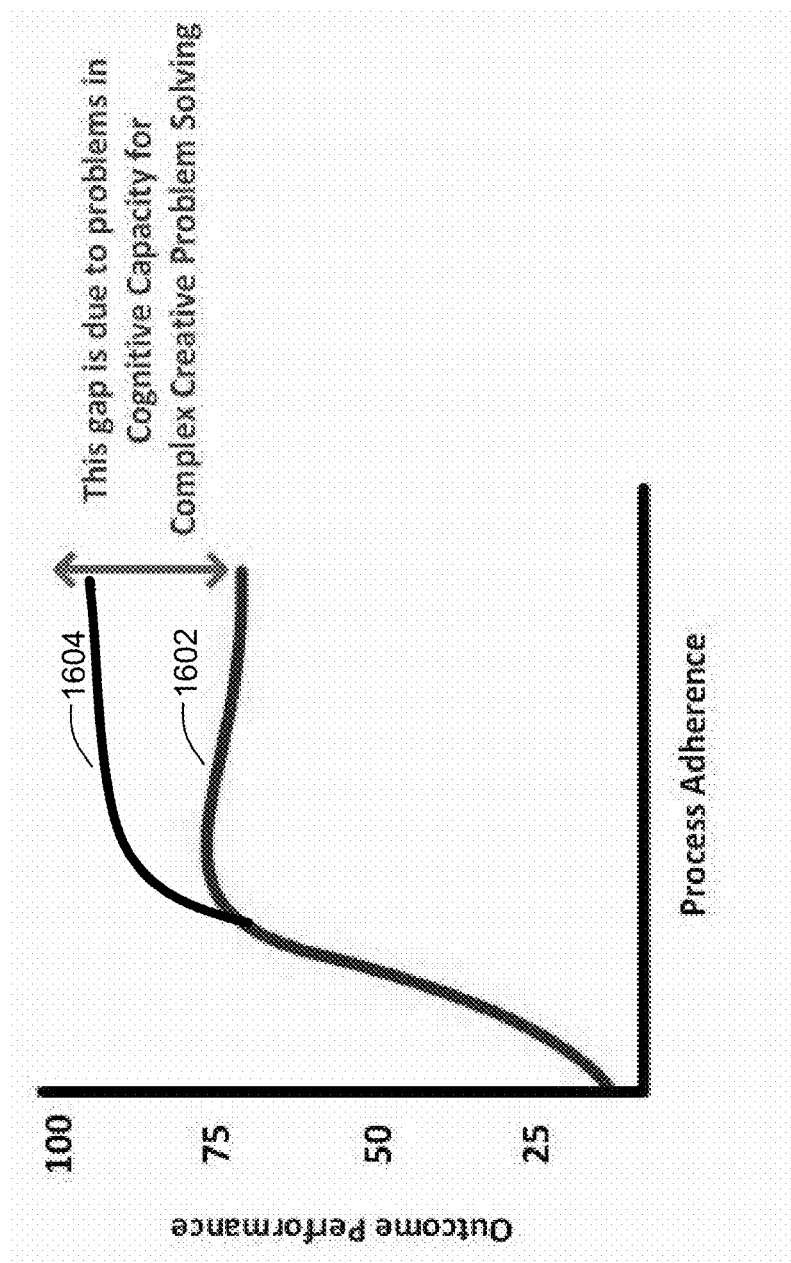
FIG. 16 is a graphical illustration of how outcome performance of a healthcare professional is improved by using embodiments as described herein.

A reason for this improvement is the increase in cognitive capacity for remembering IHBP provided by identifying and reducing the effects of tipping points as described herein. That is, by offloading tasks, distractions that interfere with remembering and applying IHBP are often reduced or eliminated. As a result, a healthcare provider is better able to adhere to IHBP. FIG. 16 is a graphical illustration of how outcome performance of a healthcare professional is improved by using embodiments as described herein. As shown in FIG. 16, patient outcome performance is illustrated as a function of process adherence to IHBP. Curve 1602 represents exemplary outcome performance as a function of process adherence to IHBP without using embodiments as described herein. Curve 1502 illustrates that at a certain point, outcome performance levels off, and even diminishes. This illustrates that even with additional adherence to IHBP, outcome performance does not continue to increase.

Curve 1604 represents exemplary outcome performance as a function of process adherence to IHBP using embodiments as described herein. Curve 1604 illustrates that applying tipping point and load balancing as described herein allows for significantly better outcome performance even with the same process adherence to IHBP. Thus, applying tipping point analysis as described herein leads to better outcome performance. A reason for this improvement is the increase in cognitive capacity provided by identifying and reducing the effects of tipping points as described herein. That is, by offloading tasks, distractions that can interfere with positive patient outcomes are often reduced or eliminated. As a result, a healthcare provider patient outcome performance is improved.

Thus, FIGS. 15 and 16 illustrate that using predictions of when IHBP will not be followed and/or outcomes will be poor through a tipping point analysis based on cognitive overload predictive modeling with a solution using a cognitive capacity load balancing system that will improve adherence to IHBP and patient outcomes.

Figure 17:
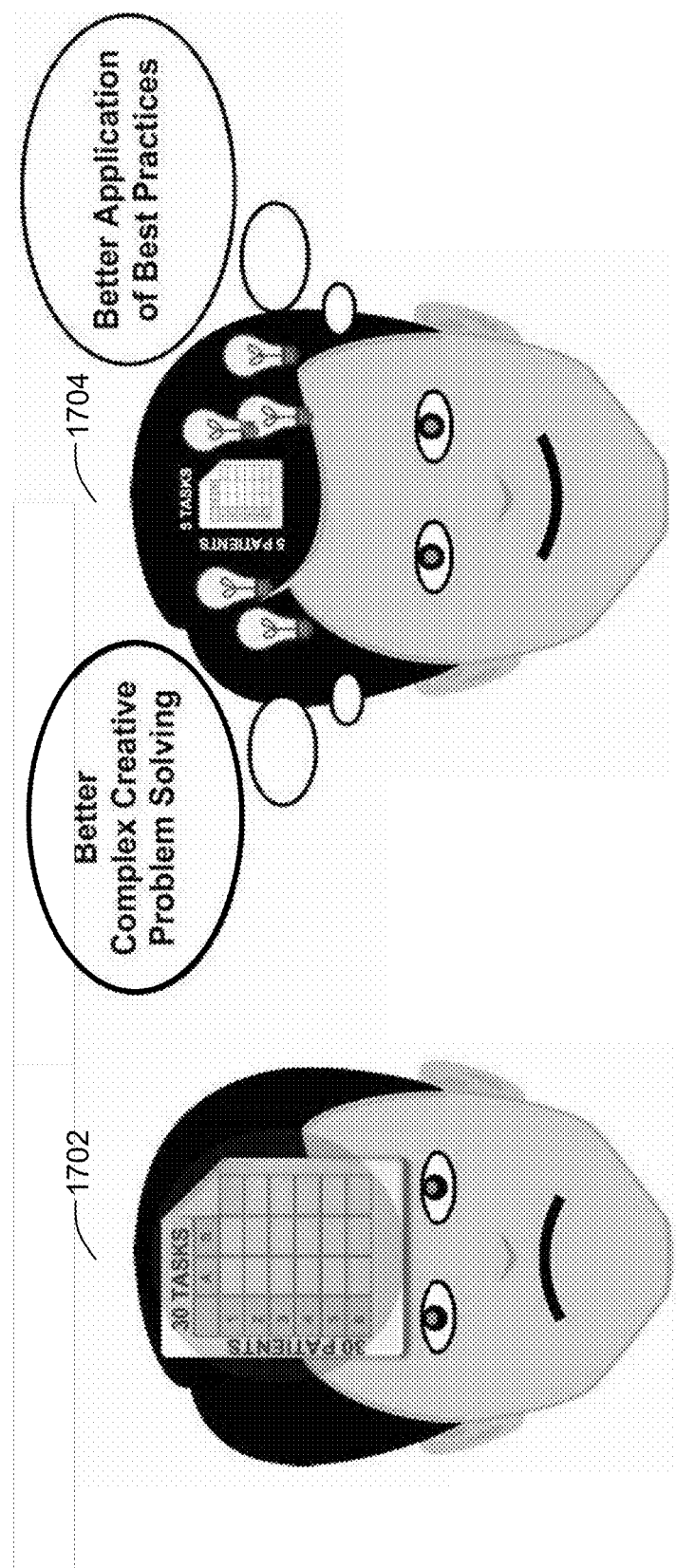
FIG. 17 illustrates graphically how cognitive capacity is improved according to embodiments described herein.

FIG. 17 illustrates graphically how cognitive capacity is improved according to embodiments described herein. As used herein, cognitive capacity is a measure of the available mental process a person can devote to a particular issue. The left portion of FIG. 17 represents exemplary healthcare provider 1702 without the benefit of embodiments as described herein. The right portion of FIG. 17 represents exemplary healthcare provider 1704, who would have had the same task load as healthcare provider 1702, but benefits from application of embodiments as described herein.

Without using embodiments described herein, healthcare provider 1702 (left side of FIG. 17) is inundated with an exemplary task load of 30 tasks for 30 patients. This overwhelming task load reduces healthcare provider 1702's ability to treat each patient effectively. For example, healthcare provider 1702 will have very limited time to apply creative problem solving to handle patients present issues that cannot be treated by adherence to IHBP, or that have some other emergency that requires a unique solution at a given time. In addition, due to the overwhelming task load, healthcare provider 1702 will likely forget to perform certain tasks, putting adherence to IHBP at risk. Further, healthcare provider 1702 will have limited time to discuss the patient after care. As a result, healthcare provider 1702 will experience increased stress and reduced effectiveness, which not only puts a strain on healthcare facility resources, but also increased the likelihood of negative patient outcomes.

By using embodiments described herein, healthcare provider 1704 (rightside of FIG. 17) benefits from a significantly reduced task load. In the example of FIG. 17, healthcare provider 1704 would have had the same task load as healthcare provider 1702. However, application of embodiments as described herein reduced the exemplary task load to 5 tasks for 5 patients. Thus, healthcare provider 1704's cognitive capacity is significantly improved compared to healthcare provider 1702. As a result of using embodiments described herein, healthcare provider 1704 will be more able to treat each patient effectively. For example, healthcare provider 1704 will have more time to apply creative problem solving to handle patients that present issues that cannot be treated by adherence to IHBP, or that have some other emergency that requires a unique solution at a given time. In addition, due to reduced task load, healthcare provider 1704 will have greater capacity to adhere to IHBP. Further, healthcare provider 1704 will have more time to discuss the patient after care, which will likely reduce readmissions. As a result, healthcare provider 1704 will experience less stress and increased effectiveness, which improves efficiency of healthcare facility resources, and decreases the likelihood of negative patient outcomes.

Using embodiments as described herein provides additional benefit to a healthcare facility as well. For example, in medical training, such as training interns, learning is enhanced by offloading tasks that do not have to be performed by a particular intern. That is, by reducing or eliminating interruptions or multitasking and/or overload associated therewith using reallocation of flexible resources provides more cognitive capacity for learning. For example, better spacing of rounds is available so that the intern has time to digest what is learned. This is because without the overload, learning can take place in the hippocampus, where learning and retention is maximized rather than the striatum. In turn, this allows for better adherence to IHBP, enhanced creative problem solving, when things do not go as planned or when a task checklist cannot be followed in a particular case, and better patient outcomes.

In addition, embodiments reduce patient readmissions. By predicting tipping and preventing those predicted tipping points through redistribution of tasks to flexible resources, tasks that are required to prevent readmissions can be identified and executed. Further, because the direct care provider has offloaded tasks that would otherwise overwhelm him or her, the direct care provider has more time to provide better communication to the patient as well as the patient's family and others who will provide care after the patient leaves the healthcare facility so that after care will be better, and decrease the probability that the patient will require readmission. This is an example of comparative advantage of using after care providers (e.g., family and others) to provide needed care rather than the resources of the healthcare facility.

In an embodiment, the problem of tipping points can be considered as Venn diagrams, with the intersection of (1) most complex patients, (2) busiest caregivers, and (3) most flexible (human) resources. As described above, 50% of improvements will be from just 5% of task distributions.

Following is an overview of Process Adaptation (toward Clinical Load Balancing) using Realtime Video/Audio processing, and Augmented Reality according to an embodiment. Since augmented reality can help people more quickly and easily understand complex situations, and thus reduce perceived complex multitasking, in an embodiment, situations are analyzed to then offer augmented reality for freeing up at least 5% more time or load factor. As a result, if monitoring stress, work type and features, etc., of flexible resources (with likely a different pay class, with expected different job type), past monitoring and a priori knowledge help develop adapters/translators for making the work needed (i.e. the actions, decisions, and format of input/output) be similar to what they appear to know well already, and to multitask faster and better.

In an embodiment, similarity-based learning (SBL) along with an a priori knowledge base of "translation" mechanisms governed by a meta-level manager that can look at outcome data and past performance execution data, to develop a cost terrain of which mechanisms to use to translate work. For example, when doing process adaptation for a caregiver supply of Nurse Staffing Coordinator (indirect care) to meet the needs of a Quality Dept. staff (also indirect care, but doing rounds with frontline caregiver like Nurse Practitioner or PA), then the progression is as follows:

Translations of supply to demand via . . . Goals of Process: Call-off (Fill-in) Handling after Scheduling of Nurses (decisions/actions) to Core Measure Handling of Quality Worklist of Patients . . . (progressively handled in process translation by "going meta") . . . .

just like a CALL-OFF FILL-IN NEED means find person with problem needing fixed on Schedule, the CORE MEASURE NEED means finding a person with problem needing fixed on Report just like CALL-OFF FILL-IN NEED step 2 is find someone to act b/c of the gap in a schedule (i.e. missing person, the CORE MEASURE NEED step 2 is find someone to act b/c of the gap in a medication requirement for a patient just like there is a correct list of call-off filler persons to fill-in, there is a correct list of meds to use just like someone has to call (or text, mail, or even visit) the person to see who can do the NEED FULFILLMENT action, we need similar action in both cases In this way, embodiments make the strange familiar, and add context, helping retention and subsequent execution and reducing perceived complexity of CTPs, and thus reducing the performance-degrading multitasking.

The following exemplary table format (for example, using Microsoft Excel) and exemplary content can be used to provide an a priori ontology that can be used in an embodiment:

| Has sheets with... | | | | | | | | | | |
|---|---|---|---|---|---|---|---|---|---|---|
| LABEL | Synonym | 2 | 3 | 4 | 5 | 6 | 7 | 8 | 9 | 10 |
| | Qualifier | 2 | 3 | 4 | 5 | Dxs | 2 | 3 | 4 | 5 |
| | Objective | 2 | 3 | 4 | 5 | | | | | |
| BNP | BNP | BRAIN_NAT | | | | | | | | |
| | PG/ML | PG_ML | | | | CHF | HF | | | |
| | Core Measure | Complication | | | | | | | | |
| Troponin | Troponin | Trop | TN | | | | | | | |
| | NG/ML | NG_ML | | | | AMI | Myocardial Inf | | | |
| | Core Measure | Complication | | | | | | | | |
| WBC | WBC | White_Blood | | | | | | | | |
| | K/CUMM | K_CUMM | Thou | | | PN | Pneumonia | | | |
| | Core Measure | Complication | | | | | | | | |
| FieldMaps for A Priori Knowledge | | | SYNONYM | | SYNONYM | SYNONYM | | | | |
| | SYNONYM | SYNONYM | Example: | 1 | 2 | 3 | 4 | 5 | 6 | |
| | 7 | 8 | | | | | | | | |
| 1 | FIN | Account | Visit | | | | 088 | 490 | 2001 | |
| | HEURISTIC--10digitsInPID | | | | | | | | | |
| 2 | Name | First Name | Last Name | Patient | | | | John | Smith | |
| | Susan | Johnson | HEURISTIC--2stringsSeparatedBySpaceOrCaratInPID | | | | | | | |
| 3 | Date | Admission | Admit | | | | | 200906150451 | | |

-continued

| | | | | | | |
|---|---|---|---|---|---|---|
| 4 | ProcessItem | Procedure | | | BMP | Metabolic Panel |
| | BNP | HEURISTIC--2stringsSeparatedBySpaceOrCaratInPID | | | | |
| 5 | MRN | Medical Record | | | 000 | |

Document Maps for A Priori Knowledge                    SYNONYM for Document Name

| | SYNONYM | SYNONYM | SYNONYM | SYNONYM | SYNONYM | |
| | SYNONYM | SYNONYM | SYNONYM | SYNONYM | START of New Record | |

Marker (place MSH section right before this)    Other Possible Marker 2       Other Possible Marker 3       4       5

| 1 | Consult | Consult Report | Consultation | CONSULTATION | | |
| | | | MSH | Result Type: | Result type: | PATIENT: |
| 2 | H_and_P | History and Physical | History & Physical | H&P | HISTORY AND PHYSICAL | |
| | | | | MSH | Result Type: | Result type: PATIENT: |
| 3 | ED_Note | ED Note | Emergency Department | EDIM | | |
| | | | MSH | Result Type: | Result type: | PATIENT: |
| 4 | ChestXray | Chest X-Ray | Chest X Ray | XR | | |
| | | MSH | Result Type: | Result type: | PATIENT: | |
| 5 | CT_Chest | CT Chest | | | | |
| | | MSH | Result Type: | Result type: | PATIENT: | |
| 6 | CT_Head | CT Head | | | | |
| | | MSH | Result Type: | Result type: | PATIENT: | |

Sections of Dictations - Maps for A Priori Knowledge                Start Marker Synonym 1

| | SYNONYM | SYNONYM | SYNONYM | SYNONYM | Take Only Line? (else takes to markers) | End Marker Syns | Synonym |
| 1 | ASSESSMENT | | Assessment | Impression | ASSESSMENT AND PLAN: | | |
| | IMPRESSION | | | Signature | Cc: | | |
| 2 | Final_Report | FINAL REPORT | | Final Report | | Y | |
| | xxyyzz xxyyzz | | | | | | |
| 3 | Allergies | ALLERGIES: | | | | Y | xxyyzz xxyyzz |
| 4 | Medications | MEDICATIONS: | | | | Y | xxyyzz |
| | xxyyzz | | | | | | |
| 5 | Preliminary_Report | PRELIMINARY REPORT | | Preliminary Report | | | |
| | Y | xxyyzz xxyyzz | | | | | |

WordsToFilter
Negations

The following exemplary table format (for example, using Microsoft Excel) and exemplary content in conjunction with comments can be used to provide an SBL user interface 35 according to an embodiment:

Column:   2    3    4    5    6    7    8    9    10
                PN

Target Report
To reduce initial workload to enable capitalizing on new information regarding Hidden Demands and Supplies of Healthcare Management
GOAL: This format and content sample below helps create the COMMAND.txt used by the Machine Learning module

| MRN | ROOM | PATIENT NAME | DIAGNOSIS | ADM Date | PHYSICIAN NAME | AGE | Echo Eval If Avail | | Reason For Visit |
| 000900000 | 88802 | Doe, John | HF | 12/2/06 4:24 | BRYCE | 55 | | | ABDOMINAL AORTIC ANEURYSM |
| 000900100 | C922A | Doe, Jane | AMI | 12/2/06 22:15 | DAVID MD | 31 | January 24_ 2008 | Indicates Shortening Fraction: | CORONARY ARTERY DISEASE_ |
| 000900400 | E917A | Moo, Stephen | HF | Sepsis | 12/1/06 21:49 | BRYCE | 75 | | SEPSIS_ NEW ONSET OF ATRI |

HF RECORDS EVAL SHEET (for Parametric Tuning based on our Data Mining)TOKENS:
NOTE: For now: (i.e. On this row, in an embodiment, there may be a partial string match to ALL the tokens in the ontology row from the Ontology file, as opposed to what's found in text file that was read, to then match to record in col. B, or simply to col. A itself from this file, whereupon pairings will need to be separated with a "*" character for wildcard, and order may be a problem so might need to reverse order on the pairings further down in list of Col. A); Note that the "p/m" unit was inserted manually into this sheet as a way of checking whether it actually gets rid of records, and if not, then ignore          BNP
          BRAIN_NAT PG_ML

| 7 | ACCEPT? (Y/N) | | Min.Criteria | | DQOr | | QualOrQualOrQualOr | |
| 7 | RECALL: | 50% | 0% | 100% | 100% | 100% | | |

NOTE: Need to see if this record is for a patient that had this Dx (based on claims data findings)

| | PRECISION: | 50% | 0% | 67% | 100% | 67% | | |
| | ACCEPT AS formula | | DQOr | QualOrQualOrQualOr | | | | |

Use these answers in this sheet: QualAnd,QualOr,DQAnd,DQOr         ACCEPT manual override (enter another name or just put space)

GOAL: Highest possible Recall based on Ontology, coupled with highest possible Precision, using...(data from all available records, to then match to Targeted Report format and content)     Rank (of Combined Score calculated below)     11     2     1     2
"NOTES: Default is to use Row 1 token as a OR item based on top rank, but if helps Recall/Precision (i.e. we see that the pairing actually is found always in the best records and never in the unwanted records), then use Column A token pairing as AND, entered manually for now into CFG files; Full Match means that this pairing of search token and qualifier to ensure its correct item sought, both found in the Ontology, has been found; Note that we may need to separate the different Dxs since will need to put so many tokens at the top of these columns, and may run out otherwise; If the Recall score is >= other tokens, and the Precision is >=, then take this ALONE, but if Recall lower by x% while Precision higher than y% threshold for other tokens, then take other tokens as well; If ""Full Match"" pairing rather than single item (i.e. no ""NOTOKEN"" found in the pairing), then put into AND row the 2 items in the pairing, else put in non-NOTOKEN item as OR row; dqAND and dqOR need to, for now, be manually entered into the CFG files, but maybe later into this file to then create the CFGs from this -- an example would be if ""dyspnea"" was being found in ""dyspnea secondary to COPD"" so the latter phrase could be a dqAND, or ""no dyspnea"" becomes a dqOR; In fact, for all the negations, an embodiment may want to look for the keywords desired when coupled with the negation keywords, to see how they're being done.
* * *Need to be able to add in PN Dx and get new CFGs OK -- (use different sheets, and loop on Dxs found to create CFG files)
"     0%     67%     100%     67%
Command, and Match Tokens     AUDIT     MATCH
Please learn from this file for Core Measures ,     HF ,     AMI , HF Sepsis -- with fields of ,MRN,ROOM,PATIENT NAME,DIAGNOSIS,ADM Date,PHYSICIAN NAME,AGE,Echo Eval If Avail,Reason For Visit
     Full Match
BNP---PG_ML
"MSH|_____|SQ|BIN|SMS|BIN|200906150504||ORU_R01|61381022514|P|2_1|||||
PID|001||000562932||SMITH_JOHN_____||19281123|F||||||||||490162644|||||||||
PV1|0001||A1_A101A|||||||||||||||||0|||||||||||||||||||||||||TOM_JONES_MD|CHEST_PAIN||
ORC|RE|||||||||||LAB|||||
OBR||49_001|49001|BNP_BRAIN_NATR_PEPTIDE|||20090615045|||||||||200906150504|_____
_|1485||||M24572|||||F|___PGLU|_____R
OBX|1|NM|BNP|134|PG_ML|70_110|H|||Z
OBX|2|FT|PGLU_GLUC||MD_Notified_by_RN||||||Z__
RECORDBREAKMARKER1
"     Full Match     Y     Y     Y
FIELDS EVAL SHEET (for Parametric Tuning based on Data Mining)          TOKENS:
NOTE: For now: (i.e. On this row, in an embodiment, there may be a partial string match to ALL the tokens in the ontology row from the Ontology file          FIN
     Name     Date
0
15     Number of Hits:     9     1     1     1
NOTE: Need to see if this record is for a patient that had this Dx (based on claims data findings)     Status:     TooMany     OK     OK     OK
Use these answers in this sheet:
GOAL: Most relevant fields to include in output reports
Command, and Extract Formula     IN     AUDIT     APPROVE? (Y/N)
Please learn from this file for Core Measures ,     HF ,     AMI , HF Sepsis -- with fields of ,MRN,ROOM,PATIENT NAME,DIAGNOSIS,ADM Date,PHYSICIAN NAME,AGE,Echo Eval If Avail,Reason For Visit
Item: FIN -- Field: 18
     s/PID\|(\w*)\|(\w*)\|(\w*)\|(\w*)\|(\w*)\|(\w*)\|(\w*)\|(\w*)\|(\w*)\|(\w*)\|(\w*)\|(\w*)\|(\w*)\|(\w*)\|(\w*)\|(\w*)\|(\w*)/PID|$1|$2|$3|$4|$5|$6|$7|$8|$9|$10|$11|$12|$13|$14|$15|$16|$17|START_FIN_$18_END_FIN/g;
     PID|001||000562932||SMITH_JOHN_____||19281123|F||||||||||490162644|||||||||     Y
     Y     Y
Item: FIN -- Field: 3
     s/OBR\|(\w*)\|(\w*)\|(\w*)\|(\w*)\|(\w*)\|(\w*)\|(\w*)\|(\w*)\|(\w*)\|(\w*)\|(\w*)\|(\w*)\|(\w*)\|(\w*)\|(\w*)\|(\w*)\|(\w*)\|(\w*)\|(\w*)\|(\w*)\|(\w*)\|(\w*)\|(\w*)\|(\w*)\|(\w*)\|(\w*)\|(\w*)\|(\w*)\|(\w*)\|(\w*)\|(\w*)\|(\w*)\|(\w*)\|(\w*)\|(\w*)\|(\w*)\|(\w*)\|(\w*)\|(\w*)\|(\w*)\|(\w*)\|(\w*)\|(\w*)\|(\w*)\|(\w*)\|(\w*)\|(\w*)/OBR|$1|$2|START_FIN_$3_END_FIN|$4|$5|$6|$7|$8|$9|$10|$11|$12|$13|$14|$15|$16|$17|$18|$19|$20|$21|$22|$23|$24|$25|$26|$27|$28|$29|$30|$31|$32|$33|$34|$35|$36|$37|$38|$39|$40|$41|$42|$43|$44|$45|$46|$47|$48/g;
     OBR||49_001|49001|BNP_BRAIN_NATR_PEPTIDE|||200906150451|||||||200906150504|_____|1485||||M24572||||F|___PGLU|_____R
Item: Name -- Field: 5
     s/PID\|(\w*)\|(\w*)\|(\w*)\|(\w*)\|(\w*)\|(\w*)\|(\w*)\|(\w*)\|(\w*)\|(\w*)\|(\w*)\|(\w*)\|(\w*)\|(\w*)\|(\w*)\|(\w*)\|(\w*)/PID|$1|$2|$3|$4|START_Name_$5_END_Name|$6|$7|$8|$9|$10|$11|$12|$13|$14|$15|$16|$17|$18/g;
     PID|001||000562932||SMITH_JOHN_____||19281123|F||||||||||490162644|||||||||     Y
     Y     Y
TEXT RECORDS EVAL SHEET (for Parametric Tuning based on Data Mining)
     List of Reports Desired
0
2
NOTE: Need to see if this record is for a patient that had this Dx (based on claims data findings)
Use these answers in this sheet: QualAnd,QualOr,DQAnd,DQOr
GOAL: Highest possible Recall / Precision, BUT also to modify Ontology so don't have -continued

```
document collisions based on shared keywords (e.g. CXR, US Abd) when documents should
actually be separate
Command, and Match Tokens            AUDIT of Line           Approved? (Y/N)              Auto
Approval? (Y/N)      Occurrence # of this Match Token        Empty Cell?
Consult---Result Type:            (Consult) Result Type: Consult                  Y         1
Consult---Result Type:            (Consult) Result Type: Consult                            2
                                  1              Y
Text Sections EVAL SHEET (for Parametric Tuning based on our Data Mining)
         TOKENS:      Section-Source:           _of_        _of_        ASSESSMENT_of_Consult
         Allergies_of_Consult Medications_of_Consult
14                    Section Ratio           #DIV/0!      #DIV/0!          100%       100%       100%
2                     Number of Hits:         Total Count    -       -         1          2          2
                      Status: Trigger to Take            NotUsed-EmptyErr?         NotUsed-EmptyErr?
         GoodEnough      GoodEnough           GoodEnough
                                 Section Header:                       ASSESSMENT         Allergies
         Medications
Use these answers in this sheet — In an embodiment, there are MAX 40 training example
records: (NOTE: May want to transpose axes to extract more sections, since example records
may only be 200 or less anyway)                   In an embodiment, this may be an optional row
         FilenameSrc: (note: May need to add the filename into the Section Header, since for
example "Impression" can appear in more than 1 file, with different markers in each, but
useful from each file for us to take)                        InitMiner-Consult.txt InitMiner-
Consult.txt       InitMiner-Consult.txt
GOAL: Most relevant fields to include in output reports                           Start Marker:
              Impression        Allergies        MEDICATIONS:
         ON ROW 10: (Do a field extract formula here to say we have from start to end, and
what it looks like in audit)???Formula:
=IF($D11<>"Y","",IF(ISERROR(FIND(E$1,$A11)),"","Y")); (Put filename of mined .txt in
here for use in creating the final CFG file to put into TVM-CSV)                 End Marker:
              RECORDBREAKMARKER1                    NOENDMRKR                  NOENDMRKR
PATIENT RECORDS FOUND -- Document Type (e.g. H_and_P, or Consult)                           #
         AUDIT of Entire Record           APPROVE? (Y/N):
                   "RECORDBREAKMARKER1
MSH
"        SrcType:                   Consult         Consult         Consult
Consult                     "RECORDBREAKMARKER1
MSH
Result Type: Consult [Record assumed to be: Consult]
ACCT Number: 99
MRN: 11
Patient Name Jane Doe
History of present illness came in from ambulance into ED with acute chest pain
MEDICATIONS: His current medications include DIVALPROEX Tegretol ZOSYN
Allergies peanut
Exam Neurological Cardiovascular
Laboratory: Elevated sodium 150 mg/l Troponin .9 ng/ml
Impression heart failure stroke "RECORDBREAKMARKER1
MSH
Result Type: Consult [Record assumed to be: Consult]
ACCT Number: 5555
MRN: 55
Patient Name JOHN SMITH
History of present illness came in from ambulance into ED with acute chest pain
MEDICATIONS: His current medications include DIVALPROEX Tegretol ZOSYN
Allergies peanut
Exam Neurological Cardiovascular
Laboratory: Elevated sodium 150 mg/l Troponin .9 ng/ml
Impression Can just his heart failure new mony a stroke
_"                              peanut          His current medications include
DIVALPROEX Tegretol ZOSYN
Formulas To Combine            Filter Column Audit         Tabulated Data...                Section:
         ASSESSMENT                ASSESSMENT               Final_Report         Allergies
                          v Show Details (Y/N):                       Source:           Consult
         Consult           Consult            Consult
                           Y                  B:           Assessment        IMPRESSIONFinal_Report
         ALLERGIES
                                              E:           RECORDBREAKMARKER1
         RECORDBREAKMARKER1                                NOENDMRKR                   N/A
         Filter
         ASSESSMENT___Consult_____Assessment_____RECORDBREAKMARKER1_____
         ASSESSMENT___Consult_____IMPRESSION_____RECORDBREAKMARKER1_____
_        Final_Report___Consult_____Final_Report_____NOENDMRKR_____
         Allergies___Consult_____ALLERGIES_____NOENDMRKR_____
-        "RECORDBREAKMARKER1
MSH
EXAMPLE OF DICTATIONS USED FOR RESIDENT LOG PROGRAM
(AS WELL AS ICD/BILLING COMPONENT):
M S H
31001"
```

The following exemplary table format (for example, using Microsoft Excel) and exemplary content in conjunction with comments can be used to provide a ClinCensProfile-vDec08-wAMLOS [what does this file show?] according to an embodiment:

---

HEADERS that denote steps...
MRN
ROOM
PATIENT NAME
DIAGNOSIS
Echo Eval If Avail
PRO Keywds + Revised RFV PRO Keywords? (filter on Y)
Reason For Visit
Dx from Clinical Data (Quality/Core Measures/ Complications Prevention Teams)
ProfileAudit
LOS
Most Significant AMLOS from RFV    (Case Mgmt)
Most Severe Princ.Dx Name    (CDMP)
Dx Mne-monic
MCCs
CCs
ProcessAudit    (for Auditing by Physician Advisors)    [This shows sequence, but can show Day# of Tot.Stay or Hr.# of first 48 hrs.; max.100 steps]
Process Item Issues vs. Order Sets
Consultant List (Case Mgmt / PAs)
Overall Complexity Overload Score (All, vs. Tipping Point of Dr. for his current Case Mix vs. past performance with this type of case load)
Flagged as TopTier, <2 day LOS)?
Dx    Count
Mortality Risk Score (Rapid Response)
Physician Busy-ness (Flex Resources/ Consultants)
Potential Infection Control Patient?
Highly Probable Sepsis
Highly Probable SkinUlcer
Med Adm Records (MAR, for Core Measures)
Stk1-MC-6 (DVT proph/ blood thinr)
Stk2-MC-7 (Anti-throm-botic)
STK-3 MC-8 (Anticoag-ulant)
HF-3   MC-2 (ACE/ Arb)
PN-2    MC-11 (Pneumovax)
PN-3a MC-1 (PN ABX)
AMI-1    MC-5 (Aspirin)
-
EBM Audit Relevant to Case    (for Physician Advisor)
Hyperlinks to press for IHBP/EBM Venn Graph/Process Map, if TermSrvr version of XLS
Critical Summary of IHBP Notes for Physician Advisors
( More Conjoint Dxs Being Added Each Week)
    In an embodiment, these are weighted twice as high This col. Needs to be calculated w/ lookup tbl that sees which patients have D/C order, or at least D/C record, or worst case on yesterday's census but not on today's
CurrCount    Physician    Inpt Census Outside List    Total    AdmitsDischarges    TooBusyThreshold (from historical patterns)OverThresholdScore (later weight by adm/dc also)
0    Dr. Smith    0    0    0    0    2    −2
2    Dr. CAROL    0    2    0    0    2    0
1    Dr. VIVIANE B.    0    1    0    0    2    −1
1    Dr. ADEKUNLE G    0    1    0    0    2    −1
        http://www.guideline.gov/ --->        EBM: (Preven.)    1
        (Maint.) 2
Complexity Overload Scoring                (Urg.)    3
        Combined EBM:
        Summ.Guidelines:
        http://www.icsi.org/guidelines_and_more/        CurrentOrderSet:
    Note: Red color means Test, not actual, Order Set
Busy Doctors        Complex Patients        Mortality:    22.70%
Doctor TotalCount    Total Overthreshold Score        DxString    CmpxPattern
    ScoreOfDxs:    RESPFAIL
    UrineCult -- CTchest -- -- -- -- -- -- -- -- -- -- -- -- -- -- -- --        <-
POSS.MISSING ORD.SET (LATER: For this DAY # of stay for this patient ONLY, so pt on day 1 shows the initial CXR, although not an IHBP's CXR that is on the 2nd day, though):
    Missing OrdSet ItemName to Filter Then Transpose onto Row2 for This Case (if this itemname found in the process audit, though, then do not show it) UrineCult
    Order Set Process    OS for...    RESPFAIL    AMI
NOTE:    CmplxPattern    *RESPFAIL*    *AMI*
Below is number of times item in row is discussed in this column's Dx order set (note: later will have Conjoint Dx Sets)...
    ProcessAudit for MRN below...    (TEST:...)    Do a CT Head, then get -continued MRI Head, followed by giving Lasix
900400 Top 10 key steps -- CXR:1 -- EKG:2 -- IDconsult:3 -- ABX:4 -- ABG:5 --
BloodCult:6    DxProfileScoring For This Case (when macro button pressed, the score for the
pt row from sheet CpxScor comes into this row)           3     0
Missing OrdSet ItemName to Filter Then Transpose onto Row2 for This Case (if this
itemname found in the process audit, though, then do not show it) High-Impact Treatment
Set (HITS) [Note: Max of 100 total allowed] Weighting Relevance To This Type of Case (so
can custom filter to show only those items above a certain threshold, or instead do a Top 10,
once there are much more than 20 HITS items)              RESPFAIL HITS: 3       AMI HITS: 7
    CTHead          0       0
    CXR             1       1
ALGORITHM: (uses Perl Subroutine in this template to do matching scoring between
CmplxPattern strings)           EBM Dx Profiles
            LATER:      Labs, ED, Consults, Regist          Meds, Procs, Chrgs,
MAR
                    Justification      Management
            Also contains...    Mortality:          22.70%      12.40%
EBM for...      EBM Available (audit via 1st 3 rows prev sheet)        CmplxPattern
    CmplxScore      RESPFAIL        AMI
RESPFAIL
        RESPFAIL***SEPSIS*CMPLXPN**HF*PNCOPD**ASTH*CAD*CP
        5.36    RESPFAIL
EBM section or passages per cell (e.g. sentence, paragraph, etc.)
        FlagForPickup (chooses max score)
This sheet's type of document always EBM              (Put EBM's Dx and Tx match score here,
then use in following sheet to see whether the score is the max score for all EBM, and if so
then can compute whether the column's cells should be evaluated for the partial string
lookups, and to point to this column when about to filter to get the relevant EBM passages
audit; NOTE: This score will be based not just on the most severe Dx of the complex pt's
list, but perhaps also taking into account which Dx's items are missing the most now or have
been historically)       200     ScoreOfEBMvsThisCase (this scoring for pt done by Perl) 50
    200
                    GenDx RESPFAIL          RESPFAIL
            FullDocument "Brief Summary
GUIDELINE TITLE
Treatment: airway, ventilation, and oxygenation. In: Guidelines for the prehospital
management of severe traumatic brain injury, second edition. "
ProcessItem(s): -CXR-----------------CTchest; >>>> Evidence Based Medicine: Variant 5:
Complicated pneumonia.
Radiologic Exam Procedure Appropriateness Rating Comments
X-ray chest 9
CT, chest 8 If pneumonia is not resolving or intervention is contemplated.
Appropriateness Criteria Scale
1 2 3 4 5 6 7 8 9
1 = Least appropriate 9 = Most appropriate
Note: Abbreviations used in the tables are listed at the end of the ""Major
Recommendations"" field."
PtMRN:      900400
MissingOrdSetItems:   UrineCult -- CTchest -- -- -- -- -- -- -- -- -- -- -- -- -- -- -- --
        UrineCult !! CTchest !! !! !! !! !! !! !! !! !! !! !! !! !! !! !! !! !!
        HITS list...
DoesRowContainMissingOrderSetItem?          Audit of HITS EBMtarget          CTHead
        CXR
0       --------------------        "Brief Summary
GUIDELINE TITLE
ACR Appropriateness Criteria ® acute respiratory illness.
"       -       -
0       --------------------        "BIBLIOGRAPHIC SOURCE(S)
Haramati LB, Davis SD, Goodman PC, Khan A, Leung AN, McLoud TC, Rosado de
Christenson ML, Rozenshtein A, White CS, Kaiser LR, Expert Panel on Thoracic Imaging.
Acute respiratory illness. [online publication]. Reston (VA): American College of Radiology
(ACR); 2005. 6 p. [18 references]
GUIDELINE STATUS
Note: This guideline has been updated. The National Guideline Clearinghouse (NGC) is
working to update this summary.
"       -       -
0       --------------------        "BRIEF SUMMARY CONTENT
    RECOMMENDATIONS
    EVIDENCE SUPPORTING THE RECOMMENDATIONS
    IDENTIFYING INFORMATION AND AVAILABILITY
    DISCLAIMER "        -       -
0       --------------------        "RECOMMENDATIONS
MAJOR RECOMMENDATIONS
Note: This guideline has been updated. The National Guideline Clearinghouse (NGC) is
working to update this summary. The recommendations that follow are based on the previous
version of the guideline.
"       -       -
0       --------------------        "ACR Appropriateness Criteria ®
Clinical Condition: Acute Respiratory Illness
"       -       -

-continued

```
0        -CXR-------------------        "Variant 1: Greater than 40 years old.
Radiologic Exam Procedure Appropriateness Rating Comments
X-ray, chest 8
Appropriateness Criteria Scale
1 2 3 4 5 6 7 8 9
1 = Least appropriate 9 = Most appropriate
"        -        CXR
```

The following exemplary table format (for example, using Microsoft Excel) and exemplary content in conjunction with comments can be used to provide an ROI analysis according to an embodiment:

| Healthcare Smartgrid ™ ROI Analysis | |
|---|---|
| Predictive Modeling, Clinical Load Balancing, and Process Adaptation for Tele-Health | |
| Item | Value |
| Number of Inpatient Cases per Month for Physician | 20 * (NOTE: Enter your selected drivers wherever cell is blue) |
| Cases Needing Improvement (due to cost or quality or both) % | 30% |
| Total Level of Cases Needing Improvement per Month | 6 |
| Average Cost Impact per Problem and Cost Also Spent to Try Correcting Problem | $1,500 * (please also see next sheet . . .) |
| Total Monthly Cost Impact of Cases Seeking to Improve | $9,000 |
| Average Number of Attending Physicians with This Level, and Cost, of Problems | 25 * (this is the key factor -- and primary determinant of ROI; Evaluated during our Assessment phase) |
| Total Monthly Cost Impact of These Cases to This Target Group of Physicians | $225,000 |
| Total Cases That Can Actually Be Improved (using Grid's insights and "freed up" time) | 28% * (our research has shown that actually 50% are realizable if 5% of time and workload is saved by Flex Resources that can be used as support buffer and leverage to overcome the identified problems) |
| Total Monthly Improvement Value from Using The Healthcare SmartGrid | $63,000 |
| Desired ROI Multiple of Healthcare SmartGrid for The Provider Organization | 500% |
| Justifiable Price per Month of The Healthcare SmartGrid | $10,500 |

| Itemization of COST Per (PROBLEM) CASE Used in ROI Analysis | | | |
|---|---|---|---|
| Item | Cost Impact/Problem | Probability/Problem | Expected Value |
| 1 Market Share/Reputation impact reflected on publicly available websites or just in physicians being wary to refer patients to hospital (10 patients at revenue of $5k/patient) | $50,000 | 5% | $2,500 |
| 2 LOS ($500/day × 4 days) | $2,000 | 50% | $1,000 |
| 3 RU for Complication ($8k average per stay) | $8,000 | 33% | $2,640 |
| 4 Case Mix impact ($1k loss per 1 AMLOS day lost) | $1,000 | 100% | $1,000 |
| 5 Other IT needed (SW implem. costs distrib. across total problems; # problems/ (% w/problems × total cases)) | $70,000 | 2% | $1,400 |
| 6 Other Staff needed (FTEs count × cost/hr. × hrs./prob.) | $500 | 100% | $500 |
| TOTAL Sum of Expected Values if ALL problems would exist | | $9,040 | |
| AVERAGE Impact if any of the problems above (i.e. conservative assumption) | | $1,507 | |

The following exemplary table format (for example, using Microsoft Excel) and exemplary content in conjunction with comments can be used to provide a fuzzy match for input data such as dxs according to an embodiment:

KNOWLEDGEBASE (built by Machine Learning trained by examples)
              Note: Need to put negative items down to the bottom, and then also put entire return sentences as return values
        Warning -- Lkup column only goes to row 110
        Caution -- put all negations of a dx after the dxs names, so the negation will overrule the diagnosis name
        Phrasing for Correction
        CHF                            PN                              CP
        ASTHMA
Sort    Item       GenName             Sort    Item     GenName            Sort     Item      GenName     Sort    Item    GenName
1       can just his heart failure                Patient has possible congestive heart failure.
        1      new mony a      Patient has possible pneumonia.                1           with acute chest pain        History involved acute chest pain.         1        asthma Patient has possible asthma.
2       no can just his heart failure        Patient has no signs of congestive heart failure.
        Zosyn    Zosyn                2        Troponin .? ng/ml        Normal Trop 2          no asthma Patient has no signs of asthma.
        !                             !                             Troponin .8 ng/ml        Hi Trop    3       as ma     Patient has possible asthma.
        !                             !                             Troponin .9 ng/ml        Hi Trop    !
        !                             !                             Troponin ?.? ng/ml       Hi Trop    !
NOTE: In an emboimdent, First 20 cols. For key dxs, while next n cols. Could be for section synonyms like impression = assessment, then we can put symptoms/adm conditions, then also meds and allergies. More dxs could be analyzed in an embodiment.
        In an embodiment, Up to 250 items being looked for from the text data below (warning, may need up to 4 lookup tables in total, since there are 4 cols. Per item). In an embodiment, additional items can be reviewed.
If the cell content is short, then can bring it to next sheet, but if long, only bring what's "understood" via lookup
Warning -- import only goes to row 500, as do formulas
ImportColumnCHF       PN        CP
NEW PATIENT
Account number 99
MRN 11 Patient
Name Jane Doe
MEDICATIONS His current medications include DIVALPROEX Tegretol ZOSYN
        Zosyn
History of present illness came in from ambulance into ED with acute chest pain
        History involved acute chest pain.
Allergies peanut
Exam Neurological Cardiovascular
concatenated cells from right put into this column A Up to 250 items being looked for from the text to left to put into proper column of E&M structure                Filter, copy and paste tranposed, save the area as output text file, which can then thru a slicer like residents log
FILTER BY Diagnoses? (Y/N):                N       Subst out name, number, MRN, shorter than 20?
        But from here need to only bring in what data miner is looking for
TotalColumnsToFilter:                      9
Enter Actual Text to Seek Here ------>                Name      Account number      History      Medication
Orig     Digest-DxRelevant     Name:     Account number:     History:      Medication:
0
NEW PATIENT
Account number 99                      99
MRN 11 Patient
Name Jane Doe                      Jane Doe
MEDICATIONS His current medications include DIVALPROEX Tegretol ZOSYN
        Zosyn                          MEDICATIONS His current medications include DIVALPROEX Tegretol ZOSYN
History of present illness came in from ambulance into ED with acute chest pain                History involved acute chest pain.      History of present illness came in from ambulance into ED with acute chest pain
Allergies peanut
Name:     Jane Doe       JOHN SMITH
Account number:              99        5555
History:         History involved acute chest pain.      History involved acute chest pain.
Medication:
Allergies:
Exam:
Diagnostics:
Impression:       Patient has possible congestive heart failure. Patient has possible pneumonia.
        Patient has possible congestive heart failure. Patient has possible pneumonia.
Plan:

------------------------------------
05/04/2010       11:59 AM        5,763,072 v1-(step3)JamesonOverloadAnalysis.xls -continued

```
            Form: (Prior Day SPV + AdmLkup − DCLkup), except 1st day 1st row, which
is just AdmLkup-DCLkup OR simply (IncremDecremCtrPrior + AdmLookup − DCLookup)
            SPV TABLE
2/16/10
2/16/2010
           Top 20 Dr. #:    1       2       3               4       5       6
Date       Doctor-->                        GABRIEL,STEVEN          KELLEY,JANE
2/16/2010           40225           1       0
2/17/2010           40226           0       0
2/18/2010           40227           0       0
            Form: (Prior Day TDC + AdmLkup − DCLkup), except 1st day 1st row, which
is just AdmLkup-DCLkup OR simply (IncremDecremCtrPrior + AdmLookup − DCLookup)
TDC TABLE
2/16/10
2/16/2010
           Top 20 Dr. #:    1       2       3               4
Date       Doctor-->                        GABRIEL,STEVEN          KELLEY,JANE
2/16/2010           40225           9.138   0.000
2/17/2010           40226           0.000   0.000
2/18/2010           40227           0.000   0.000
                                            (Note: Repeat for ARF, ComplxPN, RespFail, Sepsis, & other
MCCs or CC items; All should be found in QualCore Rpt Daily, but maybe create a sheet for
each Dx filtered to enable "Dx specialists", or instead focus on sending to specifically-named
Consultants or PAs)
Simple Multivariate Analysis for Overload Analysis
(focused on complex pts, since they have greatest risk for process variation as well as for
becoming outliers in performance)                                                   Min:
           2/16/10                                                                  Days
proximity denoting cluster (must be < #)
                                                            Max:    4/14/10
                                                            4       (NOTE: Need cond.form.formula to look
for "clustered" [1 week, 7 days, etc.] periods of elevated complexity, then overage or POA
diff. spread)
                    Patient-Days at Issue
           Complexity Quotient         Average         Overage         Spread
           4986        6.578           937             253
                                                                       The "Proper" Perspective:
"Collectively and collaboratively, what can we do to help you and thus solve this, doctor?"
                                       MULTIPLIER:             100%    10%      100%
(NOTE: Look to cluster on "Greatest Common Factor" of patient types that lead to problems)
                                       ExpPmt                  LOS     Admit    MRN       DRGcode
           DRGname         OldDRGcode (f not in previous sheet, need to look for DRG first 20
chars to find matching name in both tables and return the correct DRG, where MCC or CC
should bring in old CC, vs. w/o is w/o CC)
                                (Note: These need to be tied to the proper Dr. Name from next sheet)
                                For 3-D graphing / Findings to embed in models...
Ordered DRG list For Princ-through-2nd Dxs Conjoint Sequence             TotalComplexityDays
           Comments (currently: Is this an MCC?)                AMLOSoverage             Difference from
MAX AMLOS vs.Princ AMLOS (part of POA opp.)                     Field 11                 Field 7 Costs
           Field 5 Field 2 Field 9 Field 10             V24 DRG         OldRW            NewRW
           Payor      BNPexacLvl / LasixMgmt collated / cond. Format
           ClusterOfPossibleOverload      Attending     AdmitDt          LOS     Comment
           Negs      Pos      Append     AdmDatevalue           DCDatevalue      SPV (Simult. Pts.
Volume) in Simult.Pt-Days       TDC (Total Diagnoses Complexity)          Outcomes Init.Est.Impact
(pt-days)
*****************************************************                    7.256906027   WMCC
           −7.256906027 0       209.25 0          0     00/02/2010       700109         576
           ACUTE LEUKEMIA W MAJOR CC                    0       #N/A     3.452212168    0
           998       AB H, 00/02/2010      0            0       0        ABD
H,*************************************************0270                 0270           #N/A
           #N/A      0.00
                                Complexity Pattern Patient Profiles Where Overload Risks Are
Greatest
                                [based on input of TotalExaminedCases]
                                       Min/Max           GroupOfDxs            Combos of
                                Range for number of combinations for this number of Dxs =
           50625    15        4
                    Enter Name of Doctor Below                  30240    10       5
                    (use Blank to get composite of all Drs.):                     4096    12       2
                    STEVEN         50        758        = total examined cases
22.00%             of Dr.'s total  6.60%     of total           Weighting                 Dx Pattern
PercentCountOfCases (of This Type)Negative Sum (good) Positive Sum (bad)                  Wtd.Pos.
Combination (built from collated patterns to right)             CountDxs         Wtd.Neg.
           NetScore
2.00%     1        −0.44      2.82     ****ESOPHAGITISGASTROENT AND MISC DIGEST
DISORD AGE>17 W CC*****RENAL
FAILURE*****************************************                                 2       −0.009    0.056
           0.048
2.00%     1        −2.25      0.00     **NUTRITIONAL AND MISC METABOLIC DISORDERS
AGE >17 W CC*******RENAL
```

-continued

| | | | | | | | |
|---|---|---|---|---|---|---|---|
| FAILURE************************************* | | | | 2 | −0.045 | 0.000 | − |
| 0.045 | | | | | | | |
| 4.00% | 2 | −2.69 | 2.82 | *********RENAL | | | |
| FAILURE************************************* | | | | 1 | −0.053 | 0.055 | |
| | 0.003 | | | | | | |

SIMPLE PNEUMONIA AND PLEURISY AGE >17 W CC    CHRONIC OBSTRUCTIVE PULMONARY DISEASE NUTRITIONAL AND MISC METABOLIC DISORDERS AGE >17 W CC    CIRCULATORY DISORDERS W AMI AND MAJOR COMP DISCHARGED ALIVE
SIMPLE PNEUMONIA AND PLEURISY AGE >17 W CC    CHRONIC OBSTRUCTIVE PULMONARY DISEASE NUTRITIONAL AND MISC METABOLIC DISORDERS AGE >17 W CC    CIRCULATORY DISORDERS W AMI AND MAJOR COMP DISCHARGED ALIVE
    1    2    3    4
Selected (place above on row 1, starting at column A):    SIMPLE PNEUMONIA AND PLEURISY AGE >17 W CC PERIPHERAL VASCULAR DISORDERS W CC
    DIABETES AGE >35
        1    2    3
        1
        1
(for complexity patterns of Dxs)
Total: SIMPLE PNEUMONIA AND PLEURISY AGE >17 W CC    PERIPHERAL VASCULAR DISORDERS W CC    DIABETES AGE >35
[Create Combos button]
True/False Pattern
OUTPUT sheet:
    CHRONIC OBSTRUCTIVE PULMONARY DISEASE    NUTRITIONAL AND MISC METABOLIC DISORDERS AGE >17 W CC    CIRCULATORY DISORDERS W AMI AND MAJOR COMP DISCHARGED ALIVE    ESOPHAGITISGASTROENT AND MISC DIGEST DISORD AGE>17 W CC    HEART FAILURE AND SHOCK
        KIDNEY AND URINARY TRACT SIGNS AND SYMPTOMS AGE >17 W CC
        RESPIRATORY SYSTEM DIAGNOSIS W VENTILATOR SUPPORT
        SEPTICEMIA AGE >17    RENAL FAILURE    SKIN ULCERS    STROKE WITH INFARCT
SIMPLE PNEUMONIA AND PLEURISY AGE >17 W CC    NUTRITIONAL AND MISC METABOLIC DISORDERS AGE >17 W CC CIRCULATORY DISORDERS W AMI AND MAJOR COMP DISCHARGED ALIVE    ESOPHAGITISGASTROENT AND MISC DIGEST DISORD AGE>17 W CC    HEART FAILURE AND SHOCK
        KIDNEY AND URINARY TRACT SIGNS AND SYMPTOMS AGE >17 W CC
        RESPIRATORY SYSTEM DIAGNOSIS W VENTILATOR SUPPORT
        SEPTICEMIA AGE >17    RENAL FAILURE    SKIN ULCERS    STROKE WITH INFARCT
        NUTRITIONAL AND MISC METABOLIC DISORDERS AGE >17 W CC
    CIRCULATORY DISORDERS W AMI AND MAJOR COMP DISCHARGED ALIVEESOPHAGITISGASTROENT AND MISC DIGEST DISORD AGE>17 W CC
    HEART FAILURE AND SHOCK    KIDNEY AND URINARY TRACT SIGNS AND SYMPTOMS AGE >17 W CC RESPIRATORY SYSTEM DIAGNOSIS W VENTILATOR SUPPORT    SEPTICEMIA AGE >17    RENAL FAILURE    SKIN ULCERS    STROKE WITH INFARCT The following exemplary table format (for example, using Microsoft Excel) and exemplary content in conjunction with comments can be used to provide an ICD-predictor-final.xls [what is ICD-predictor-final] according to an embodiment:

```
INPUT
FIN      Assessment
#:   0183517317       "Assessment: This is a xx-year-old right-handed ___ American _ MD
Neurology Specialty: Cerebrovascular Neurology"
+1-Translator sheet
ICDcode      ICDname         ICDcode      ICDTop200-FILTER COLUMN
      Substrings:   1      2      3      4      5      6      Tokens:   1      2
            3      4      5      6      Search:1   2      3      4      5      6
1     CHOLERA D/T VIB CHOLERAE              1            NOTE: CHOLERA      D/T VIB
CHOLERAE      VIB CHOLERAE         CHOLERAE               CHOLERA
      D/T      VIB      CHOLERAE            CHOLERA      ---      ---
      CHOLERAE      ---      ---
1.1   CHOLERA D/T VIB EL TOR            1.1         Blue area      CHOLERA
      D/T VIB EL TOR      VIB EL TOR      EL TOR      TOR
      CHOLERA      D/T      VIB      EL      TOR            CHOLERA   ---   ---
      ---      ---      ---
1.9   CHOLERA NOS            1.9         is formula,      CHOLERA      NOS
                     CHOLERA      NOS
      CHOLERA      ---      ---      ---      ---      ---
[date chgd]      AdmittingICD OR Synonyms:      1      2      3      4      5
      AND for 1      2      3      4      5      NOT Exclusions:      1      2      3
      4      5
```

-continued

|   |   |   |   |   |   |   |   |   |   |
|---|---|---|---|---|---|---|---|---|---|
| EPISODIC MOOD DISORD NOS |   |   |   |   | mood | --- | --- | --- | --- |
| --- | --- | --- | --- | --- | --- | --- | --- | --- |   |
| ALZHEIMER S DISEASE |   |   |   | ALZHEIMER | --- | --- | --- | --- |   |
| --- | --- | --- | --- | --- | --- | --- | --- |   |   |
| AMYOTROPHIC SCLEROSIS |   |   |   |   | AMYOTROPHIC | --- | --- | --- |   |
| --- | --- | --- | --- | --- | --- | --- | --- | --- | --- |

Simple "AND"    More complex "AND"
ICDSynonymsFoundInAnyOfCombinedEDIMDxs?    (WARNING: Did just Top 200, as found in the ICDtoDRG sheet)    And for all synonyms If AND (starts in col. I) for a specific column, then this word must be found in order for synonym (the OR columns starting in D) to be taken
IF(AND(IF(ISERROR(SEARCH('6'!$M2,E$10)),0,1)>0,IF(ISERROR(SEARCH('6'!$H2,E$10)),0,1)>0),1,IF(ISERROR(SEARCH('6'!$M2,E$10)),0,1)))>0),1,"")
Concatenation of Dxs are in cells on row 10

```
            PtName:              0183517317    0183517184
    0183517598   0183517648   0183517424
            EDIM Pt (Row-1) #:  1   2   3   4   5   6   7
ICDcode    ICDname      0   0   "Assessment: This is a xx-year-old right-
handed ___ American ..."
"
296.9      EPISODIC MOOD DISORD NOS       1
331        ALZHEIMER S DISEASE            2
335.2      AMYOTROPHIC SCLEROSIS          3
784.3      APHASIA          4
290.4      VASCULAR DEMENTIA_UNCOMP            5
447.6      ARTERITIS NOS         6
446.5      GIANT CELL ARTERITIS       7
350.2      ATYPICAL FACE PAIN         8
351        BELL S PALSY          9
434.9      CRBL ART OC NOS WO INFRC       10
343.9      CEREBRAL PALSY NOS         11
437        CEREBRAL ATHEROSCLEROSIS       12
723.8      CERVICAL SYNDROME NEC          13
333.5      CHOREA NEC         14
357.89     INFLAM/TOX NEUROPTHY NEC       15
349.9      CNS DISORDER NOS           16
300.1      HYSTERIA NOS          17
414        COR ATH UNSP VSL NTV/GFT       18
436        CVA        19
300.4      DYSTHYMIC DISORDER         20
780.4      DIZZINESS AND GIDDINESS        21         1
#N/A       #N/A       22
348.3      ENCEPHALOPATHY NOS         23
345.9      EPILEP NOS W/O INTR EPIL       24
345.91     EPILEPSY NOS W INTR EPIL       25
           1
334        FRIEDREICH S ATAXIA        26
781.2      ABNORMALITY OF GAIT        27
357        AC INFECT POLYNEURITIS         28
900.9      INJ HEAD/NECK VESSEL NOS       29
784        HEADACHE 30       2            1   1   2
368.4      VISUAL FIELD DEFECT NOS        31
PtName:                3517317
PtRow:             1       2
           0        "Assessment: This is a xx-year-old right-handed ___ American . Neurology "
1          DIZZINESS AND GIDDINESS
2          HEADACHE
3          MGRN UNSP W NTRC MGR STD
4
DRGNameLookup
DRGNameOutput
FIN        DRG List
              AMI:Min
0183517
0183517
01835171
01835175
01835176              HF:Min:     Stroke:Min
01835174
```

The following exemplary table format (for example, using Microsoft Excel) and exemplary content in conjunction with comments can be used to provide an exemplary machine learning structure according to an embodiment:

---

NOTES: Includes fuzzy match of similar patient names, like John Doe and Doe John if the Age, Gender, and Payer are the same for example
  Also if have exact time of day, want to include whether day, evening, or night for nurse shifts and physician rounding schedules
    In U.S., studies have shown every complication infection averages $15k    Although impacting costs, these procedures have much lower "predictive" value since they tend to happen later in the stay, so thus their general weighting coefficients are lower on day 1
    Includes fuzzy match of similar items like Dyspnea and SOB
    Predictive Model Development via Profiling, Clustering (apples-to-apples), then Weighting
    to Estimate Daily Costs and Perform Daily "Course Correction"...
    Prioritize to get 50%-5% (half of problem size found in top 5%) to the top, then the FRL can work the rest of the list downward; Fuzzy match cases to then cluster, then weight against base cost estimate, while IHBP optimization tries to drive everyone to best doctor's practice pattern (via self-eval) to keep costs lower in those most difficult to justify and keep patient (and payer) satisfaction
        General Category Weights:
                    CurrentBaseCharge
        Visit Info                    Key Differentiators
                    Key Risk Factors
            Complexity (via ICDs)
        Finance        $15,000        Physician Practice Tendencies (Px or Chg)
                        Tipping Point Info (calculated only by HCSG)        Other data (incorporated over time from existing systems)
            Flex Resource Additions

| PtName | Internal# | SpecificWt | AdmitDate | D/C Date | Weekend? | SpecificWt |
|---|---|---|---|---|---|---|
| Physician (Attending) | SpecificWt | | Specialty | | SpecificWt | |
| Payer | SpecificWt | Age | AgeBracket | SpecificWt | GenderSpecificWt | |
| Race/Ethnic | SpecificWt | PrincipalDx (implying Admitting Dx) | | | 2ndDx | |
| SpecificWt | 3rdDx | SpecificWt | nthDx | SpecificWt | UseForBase? | |
| %OfBaseChargeAverage | | TotCharges | Proced 1 (or Chrg 1) | | SpecificWt | |
| Proced 2 (or Key Chrg 2) | | SpecificWt | Proced 3 (or Key Chrg 3) | | | SpecificWt |
| Proced 4 (or Key Chrg 4) | | SpecificWt | PtComplexityScore | | | |
| PhysicianOverloadScore | | FacilityOverloadScore | | SCOPE/DEPTH: | | |
| ADT-RFV | SpecificWt | InitBNP | SpecificWt | InitTrop | SpecificWt | |
| InitWBC | SpecificWt | InitCreat | SpecificWt | Echo EF% | SpecificWt | |
| CXR-Infiltrate | SpecificWt | Smoker? | SpecificWt | PastHistList | SpecificWt | |
| ImpressionListSpecificWt | | PlanList | SpecificWt | Crucial Phrases | SpecificWt | |
| Doe,John | 1 | 1/1/09 | 1/1/09 | Y | Dr. Z | Cardiology |
| Self-Pay | | | | M | Arab | |
| CHF | | | | Y | 100% | $15,000 |
| Lasix | Echo | | | | | |
| Pt A | 2 | 1/1/09 | 1/1/09 | | Dr. Z | Internal Med |
| Insurance | | | | M | Asian | CHF |
| ARF | | | | 233% | $35,000 | Neseritide |
| | | Dialysis | | | | |
| Pt B | 3 | 1/1/09 | 1/1/09 | | Dr. Z | Cardiology |
| Insurance | | | | M | Asian | CHF  PN |
| | | | | 200% | $30,000 | Lasix |
| Chest Xray | | Levofloxacin | | Piperacillin | | |
| John,Doe | 4 | 1/1/09 | 1/1/09 | | Dr. Z | Internal Med |
| Insurance | | | | M | Asian | |
| CHF  PN | | RespFail | | | 300% | $45,000 |
| ABG | | Ventil | | | | ...life | threatening deterioration...
Process Adaptation thru Process Arbitrage: (for profitability; mkt share from pat.pend.uniqueness of load-balancing;
    growth of this sector next 5 years given need by 2015 Elliot said)
Closely match the I/O, then inferred process critical steps of available resources
    (e.g. is an NP doing dictations & orders for this Dr.; consultants on this type of case),
    to then do SDLC on the highest ROI objectives using comparative advantage
    Put example into model (for example, using Microsoft Excel)

In an embodiment, healthcare provisioning engine 102 determines how often certain reasons for visit or chief complaints actually become a particular DRG, and thereby enables initial weighting for predictive models and also at earliest hours of case.

The following exemplary table format (for example, using Microsoft Excel) and exemplary content in conjunction with comments can be used to provide a charge discrepancies fuzzy match according to an embodiment:

Note: Need to put negative items down to the bottom, and then also put entire return sentences as return values
Table For Fuzzy Matching
　　Warning -- Lkup column only goes to row 110
　　Caution -- put all negations of a dx after the dxs names, so the negation will overrule the diagnosis name
　　Match Items
Later:　Most Exact tokens　　　　　Put Match　　　　　　　More Exact tokens
　　　　Less　Exact tokens　　　　　　　　　Least　Exact tokens
　　Radiology　　　　　　　　　　　Meds　　　　　　　　　　　　　Labs
　　Other
Sort　Item　GenName　　　　Sort　Item　GenName　　　　　　Sort　Item　GenName　　　　Sort　Item　GenName
1　　MRI*Brain　　MRI Brain　　　　1　　!　　　　　　　　　　1　　!
1　　!
2　　Brain*MRI　　MRI Brain　　　　　　!　　　　　　　　　　　　!
2　　!
　　LEV*INJ　　　Levaquin IV　　　　　!　　　　　　　　　　　　!
3　　!
　　CT*CHEST　　CT Chest　　　　　　!　　　　　　　　　　　　!
　　!
　　CHEST*X　　　Chest X-Ray　　　　!　　　　　　　　　　　　!
　　!
　　N/A　　N/A　　　　　!　　　　　　　　!　　　　　　　　　　!
　　!　　　　　　　　　　!　　　　　　　　!　　　　　　　　　　!
　　!　　　　　　　　　　!　　　　　　　　!　　　　　　　　　　!
ClinicalMgmt...
13206　　NORMLZD FORMAT: (Normalized Combine Sheet for NDT, ED, and ADT (and later, Charges) to be shown on one sheet)　　MRN Timestamp　　　FIN　　Attending　　Audit　Day#MRN　　Day#FIN　　Day#MRN　　Day#FIN　　SpecificItem (custom formula for facility)　　GenTypeOfItem　　PositiveOrNeutralFinding　　NegativeFinding　　Medicines (Extract from EDIMs)　　Medicines (Normalized and Collated on separate sheet)　　Day#MRNdifferentThanFIN?
　　TimeDiffFromDirectlyAbove CumulativeTime　　ViewingType
　　CountOfThisGenTypeForFINCostForGenTypeOfItem　　　　HospAcqCondPossible
　　InfectionPossible　　FoleyOrLinePossible　　BloodCompatibility
　　SeqFoleyInfectionForFIN　　SeqSkinUlcer　　SeqFalls　　SeqSepsis
　　SeqUTI(UWBC)　　SeqUTI(Uculture)　　SeqUTI(Urinalysis)　-　DELAY
from Last ED Visit to Admit >2 days3　　01/01/08　　GenTypeOfItem (for fuzzy match) Sequence # for Day　　FoundMatch in Classif?　　(for same service date time-frame -- i.e. give-or-take 3 days or whatever in cell AK1)　　CountFoundClassifForThisDay
　　MatchItemSpecificDate　　MatchItemSpecificName　　By Min.Match --
WARNING: May need a sequence num from float sump here　　By Hr.Match　　By Day Match By Wk. Match By Mo. Match By 2 mos. Match
ClassifOrCharges...
MRN　Acct#　LNameFNamePMI　　PatStat CDMNo　　　CDMDescr　　ChrgeAmt
　　RevCode　　CPT4　HCSPCS　　JCode　Qty　ServDt ServTime　　PostDt
　　Journal　　ConvSvcDate　01/01/08　　GenTypeOfItem (for fuzzy match)
　　Sequence # for Day　　FoundMatch in Mgmt? (for same service date time-frame)
　　CountFoundMgmtForThisDay　　MatchItemSpecificDate
　　MatchItemSpecificName　　By Min.Match -- WARNING: May need a sequence num from float sump here　　By Hr.Match　　By Day Match By Wk. Match By Mo. Match By 2 mos. Match
　　Unsupported Charges
　　Rank　GenName　　Amount
　　3　　MRI Brain　　0
　　　　MRI Brain　　(use formula that if above same as left genname, then don't do the sumproduct)
　　3　　Levaquin IV　　0
　　2　　CT Chest　　　200
　　3　　Chest X-Ray　　0
　　1　　N/A　　2000
　　3　　0
　　3　　0
　　3　　0
　　3　　0
　　　　Time Horizon View　　　　　　　　　　　　Today View of Biggest
Discrepancies -- Clinical Mgmt Missing Charges
　　　　　　　　　　　　　　　　　　　　　　　　Key Mgmt. to Charges
　　　　　　　　　　　　　　　　　　　　　　　　1　　2　　3　　4

| | Day # | Matched Charges To Mgmt. | Unbilled Mgmt. | Unsupported | | | | |
|---|---|---|---|---|---|---|---|---|
| 5 Charges | | | | | | | | |
| | 340 | 0 | 0 | 1 | | | | |
| | 341 | 0 | 0 | 2 | | | | |
| | 342 | 0 | 0 | 3 | | | | |
| | 343 | 50 | 200 | 4 | | | | |
| | 344 | 259 | 0 | 5 | | | | |
| | 365 | 0 | 0 | | | | | |
| | 366 | 0 | 0 | Today View of Biggest Discrepancies -- | | | | |
| Unsupported Charges Missing Mgmt | | | | | | | | |
| | 367 | 0 | 0 | Key Mgmt. to Charges | | | | |
| | 368 | 0 | 0 | | | | | |
| | 369 | 0 | 0 | | 1 | 2 | 3 | 4 |
| 5 | | | | | | | | |
| | 370 | 0 | 0 | | N/A | CT Chest | | |
| MRI Brain | | #N/A | #N/A | | | | | |
| | 371 | 0 | 0 | 1 | N/A | 2000 | 0 | 0 | 0 |
| 0 | | | | | | | | |
| | 372 | 0 | 0 | 2 | CT Chest | | 0 | 200 | 0 |
| 0 | | 0 | | | | | | |
| | 373 | 0 | 0 | 3 | MRI Brain | | 0 | 0 | 0 |
| 0 | | 0 | | | | | | |

The following exemplary table format (for example, using Microsoft Excel) and exemplary content in conjunction with comments can be used to provide an NBI-ALLII-cases-ForDRG291 [What is NBI-ALLII-casesForDRG291?] according to an embodiment:
InputCoding-Conversion1
Convert2-FiltrCalc
ComplexitySpread-DRG (look at Dxs in ordered pattern with "*" preceding and following in order to pick up anything with full set or even subset of pattern).

The following exemplary table format (for example, using Microsoft Excel) and exemplary content in conjunction with comments can be used to provide a CMC-HF-PrecisionDRG-Worksheet_Final according to an embodiment:

```
Uses tokens (e.g. words and phrases), in columns, with weights, to then develop scores based
on sumproducts.
Tuning is important to minimize score of false negatives and false positives vs. "hits".
        General Scoring Worksheet
        DIFFERENCE:         Avg.Score
                NOTE: Looks at Tmp sheet from C-AB cols., and then SearchTerms sheet
from E 11-E20                           Desired         71
                Put Dx seeking in C8; Handles up to 49 cases (row 12 - 60)
                        Not Desired     40
        DiffMinScore: 0         Differentiation %:      100%    93%     #DIV/0!         #DIV/0!
100%    100%
                        Score for Factor:       0       40      20      -10     10      40
        DesiredDx=      HF      Active Col. for Dx:     HF      HF      HF      HF      HF      HF
ActiveRowForDx          FIN     Score   Hit \ SearchTerms:      ADT date        RFV/Impress1
        Impress 1 /RFV normal ejection fraction         low ef  IV Lasix
(green is assumed core)                 -       -       (manual entry below)    -       -       -       -
-       -
0.154178935     115281          45      Y       Y
0.163206713     115289          75      Y       Y       Y
```

The following exemplary table format (for example, using Microsoft Excel) and exemplary content in conjunction with comments can be used to provide a NBI-WorkloadToPerformanceChart-TechAnalysisPracticer [what is NBI-Workload-ToPerformanceChart-TechAnalysisPracticer] according to an embodiment:

Charting tool to look at a week of cases for a doctor, then to see also the severity of the cases, as well as the admission volume, and discharges. Just like what was done in article in Journal of the Physician Executive The following exemplary table format (for example, using Microsoft Excel) and exemplary content in conjunction with comments can be used to provide a v4-ParamTuning-OutputFromPhraseExtractor-Brian47DoOver [what is v4-ParamTuning-OutputFromPhraseExtractor-Brian47DoOver] according to an embodiment:

| | | | | | | | | | | | |
|---|---|---|---|---|---|---|---|---|---|---|---|
| Phrase | 428 | 486 | 410 | Dx4 | Dx5 | Dx6 | 212 | | | | |
| | CountOfThisPhraseAcrossAllCases | | | | | Mean%ofPhrase | | StdDevOfPhraseFreq | | | |
| | Median | | Min | Max | Sum | Cnt>0 | CntCols | | #Words In Phrase | | |
| | DifferentiationValueFormula | | | Coeffs:0.1 | | 0.1 | 0.1 | 0.1 | 2.1 | 0.1 | 0.1 |
| | 30 | | is threshold | ActualOutcome | | | | ProjectedOutcome | | Error | TotErr:73 |
| AND | 100% | 100% | 100% | | | | 29 | | 100% | 0% | 100% |
| | 100% | 100% | 300% | 3 | 3 | 1 | 2.72 | N | 0 | 0.1 | 0.1 |
| | 0.033333333 | | 2.1 | 0.1 | 0.29 | | | 0 | 0 | 0 | |
| congestive heart failure | | | | 38% | 15% | 14% | | | | 6 | |
| | 22% | 13% | 15% | 14% | 38% | 67% | 3 | 3 | 3 | 13.98 | Y |
| | 0.05849493 | | 0.1 | 0.02239011 | | 0.055828221 | 13.65 | 0.033333333 | | 0.06 | |
| | 1 | | 0 | 1 | | | | | | | |
| ASSESSMENT | | 1 | 0% | 50% | | | | | 1 | 25% | |
| | 35% | 25% | 0% | 50% | 50% | 1 | 2 | 2 | 8.95 | N | |
| | 0.141421356 | | 0.2 | 0.05 | 0.1 | 8.4 | 0.05 | 0.01 | | 0 | 0 |
| | 0 | | | | | | | | | | |

Total Rows Required for Param Range
concentration, so then show which Dxs are impacted  Hi SD/Ave means
concentration Hi Sum/Count>0 means concentration  Hi CountCols/Count>0 means
concentration Hi 1/Median means high concentration  Hi Max/Sum means
should be more valuable  Shorter phrases greater than 1
  Number of iterations before pause  Higher Frequency Phrases should be more valuable Threshold

| | | | | | | | | |
|---|---|---|---|---|---|---|---|---|
| = | | | StartingPoint | 0.1 | 0.1 | 0.1 | 0.1 | 0.1 | 0.1 | 0.1 |
| | 0.1 | 10 | | | | | | | |
| | | | Increment | 1 | 1 | 1 | 1 | 1 | 1 | 1 |
| | 1 | | | | | | | | |
| | | | MaxOfRange | 3.1 | 3.1 | 3.1 | 3.1 | 3.1 | 3.1 | 3.1 |
| | 3.1 | | | | | | | | |
| | | | 0.1 | 0.1 | 0.1 | 0.1 | 0.1 | 0.1 | 0.1 |

Have every variable go up by 1, then see which made biggest difference, then have that variable be what we make the next change in, then repeat advance by 1 on each of the variables

| | | | | | | | |
|---|---|---|---|---|---|---|---|
| | 1.1 | 0.1 | 0.1 | 0.1 | 0.1 | 0.1 | 0.1 | |
| | | 0.1 | 1.1 | 0.1 | 0.1 | 0.1 | 0.1 | 0.1 |
| | | 0.1 | 0.1 | 1.1 | 0.1 | 0.1 | 0.1 | 0.1 |

BestSoFarInputShtRecalc
  VIEW THIS STATUS SCREEN AT EVERY PAUSE IN ITERATIONS
Dep.Var.  Indep.Vars. Value
  GRAPH: (line chart of all 8 indep. vars on 1 chart to show on y-axis of total errors so can see which var is making biggest difference, but may have to normalize their values in order to make sure param values can be viewed together in case all of them do not have the same starting point, increment, and max)
TotErrVal  Hi SD/Ave means concentration, so then show which Dxs are impacted  Hi CountCols/Count>0 means concentration  Hi Sum/Count>0 means concentration  Hi Max/Sum means concentration  Hi 1/Median means high concentration  Shorter phrases greater than 1 should be more valuable  Higher Frequency Phrases should be more valuable Threshold
  Number of iterations before pause
(formula)

| variable 1 | v2 | v3 | v4v | v5 | v6 | v7 | v8 |
|---|---|---|---|---|---|---|---|
| 0.1 | 0.1 | 0.1 | 0.1 | 0.1 | 0.1 | 0.1 | 0.1 |
| 1.1 | 0.1 | 0.1 | 0.1 | 0.1 | 0.1 | 0.1 | 0.1 |
| 0.1 | 0.1 | 0.1 | 0.1 | 0.1 | 0.1 | 0.1 | |
| 0.1 | 0.1 | 0.1 | 0.1 | 0.1 | 0.1 | 0.1 | |
| 0.1 | 0.1 | 0.1 | 0.1 | 0.1 | 0.1 | 0.1 | |

-----------------------------------

| | | | | | | | | |
|---|---|---|---|---|---|---|---|---|
| 07/25/2007 | 09:06 PM | | 49,179,648 v6-CMC-AdmissionStudy.xls | | | | | |
| AdmICD | | Filter sideways to get nonblanks? | | | Is there a way to "pack" empty cells? | | | |
| | Count of ICD | AdmICD | Name | HEART FAILURE AND SHOCK | | | | |
| | CHRONIC OBSTRUCTIVE PULMONARY DISEASE | | | | | SIMPLE PNEUMONIA | | |
| AND PLEURISY AGE >17 W CC | | | | | | | | |
| 786.59 | 1 | 1344 | 786.5 | CHEST PAIN NOS | 9 | 4 | 7 | |
| 786.09 | 1 | 1210 | 428 | CHF NOS | 105 | 4 | 0 | |
| 682.9 | 1 | 1023 | 486 | PNEUMONIA_ ORGANISM NOS | | 4 | 15 | 52 |
| 789 | 1 | 702 | 780.2 | SYNCOPE AND COLLAPSE | | 0 | 0 | 0 |
| 786.5 | 1 | 646 | 789 | ABDMNAL PAIN UNSPCF SITE | | 0 | 0 | 2 |
| Final DRG | | TotalCases | MostFreqAdmDxCaseCount | | | NameOfMostFreqAdmDx | | % |
| of Cases | | PRECISION: | CountOfICDs | Average | | StdDev | | |
| Admitting ICD Code | | 0 | 998.59 OTHER POSTOP INFECTION | | | #DIV/0! | | |
| | 199 | 560.74 204.00 | | | | | | |
| HEART FAILURE AND SHOCK | | | | 1250 | 105 | CHF NOS | 8% | -3.97% 18 |
| | 11.33 | 8.49 | | | | | | |
| CHRONIC OBSTRUCTIVE PULMONARY DISEASE | | | | | 948 | 64 | OBS CHR | |
| BRONC W(AC) EXAC | | | 7% | -3.21%21 | | 8.76 | | |
| | | | | | 5.99 | | | |
| PrincICD | | Filter sideways to get nonblanks? | | | Is there a way to "pack" empty cells? | | | |
| | Count of ICD | PrincICD | Name | HEART FAILURE AND SHOCK | | | | |
| | CHRONIC OBSTRUCTIVE PULMONARY DISEASE | | | | | SIMPLE PNEUMONIA | | |

-continued

```
AND PLEURISY AGE >17 W CC   ESOPHAGITISGASTROENT AND MISC DIGEST
DISORD AGE>17 W CC          CHEST PAIN
411.1      1     1058   428     CHF NOS        166    0      0       0    0
428        1     953    486     PNEUMONIA_ ORGANISM NOS            0    0       123    0
           0
998.59     1     550    491.21 OBS CHR BRONC W(AC) EXAC            0    90      0      0
           0
done       By Admitting to Final DRG
done       By Principal to Final DRG
           By CCs to Final DRG
           By Season to Final DRG (Q1, 2, etc.)
           By Attending and Admitting to Final DRG
           Questions:
           How well does LOS Overage correlate to Costs?
           What is the DRG & LOS Overage per Adm Dx?
           What is the consistency of DRG & LOS Overage per Adm Dx?
           Under what circumstances does it change?
           Attending Analysis:
                    (First need to complete per Hosp. the workload performance worksheet to get
GMLOS Overage per physician)
                    Top 5 Physicians by worst Overage to see the % of time certain Adm Dx leads
to Final DRG
                    Top 5 Physicians by best Overage to see the % of time certain Adm Dx leads
to Final DRG
                    Current Admission Rate, D/C Rate, and SeverityRiskAve for that physician on
n days before, during or after (i.e. be able to insert range of days from −2 thru +2)
-----------------------------------
12/05/2008          09:19 AM         6,057 VBAforHourlyTimeline.txt
    ' Get complete array of rows from the column where the cursor is (should be at orders),
then move to right one to do the results
      'Selection.Offset(2, 0).Resize(300 + 1, 1).Select
...
    ' For each hour found, get all items found, then transpose paste special on AllItems sheet
on appropriate row
      For Counter = 0 To maxHour
```

In an embodiment, a "plug" is how machine learning "learns to learn" for Process Improvement (Machine Learning Automated Process Interface, or ML-API). In an embodiment, similarity based learning is used rather than a neural network because there is not enough memory or runtime to allow the huge data and processing requirements. Using SBL offers ability to quickly incorporate the 20 Dxs that initially targeted, then those Dxs and other risks that continually come to forefront in whack a mole In an embodiment, one or more of the following techniques can be used, without limitation as to other variants: (1) Neural Network Variant is based on parametric tuning and self-modifying/self-generating code; (2) gradient descent like we had for labor arbitrage (to get 5% for 50% returns), and then (3) and then Genetic Algorithm and Simulated Annealing to attempt to get to absolute minima, or at least better local minima.

A plug according to an embodiment can employ the following reasoning, without limitation as to other reasoning paradigms. Every learning and thinking system (i.e. "brain") is essentially a set of conditionals. However, the key is how quickly (and minimizing skilled man-hours) the system can arrive at a good enough solution, whether through search space pruning, parallel processing, and human leveraging. For example, interfacing with a healthcare facility's data, even if it is HL7, can be time consuming. For instance, interface times can be affected because:

HL7 fields may have ID numbers, for patients, doctors, items, etc., that have or are missing leading/trailing zeroes;

HL7 format records may be missing certain sections (e.g. no PV1 in certain records);

HL7 records may have certain data put in alternate places, even in same facility if different systems generating;

the HL7 record (e.g. FIN can be found at times PID field 18, but at other times different FIN at field 3);

HL7 records procedure names can vary from facility to facility, even in same healthcare organization (e.g. WBC in some records, while White Blood Count in others); and HL7 fields can even have unexpected abbreviations or truncations in play (e.g. "White Blood Cou"), requiring stemming/"fuzzy matching."

Thus, HL7 is simply like saying the plug has 2 flat prongs vs. 3 round prongs (oversimplifies the problem) or not seeing the prongs at all. It is a sort of adapter or converter. But is it 120V or 220V? Metaphors aside, the plug is basically a translator, which can then also be applied later to adapting supply to the grid, not just (generally) demand about patients—our concept of "work translation." Other uses for the plug include, without limitation: (1) ability to add a new Dx and bring in the modeling necessary, while also being able to drop a Dx too; (2) handling dictation data sections (e.g. Impression extracts); and (3) ability to add in different data formats, like .txt EDIM/Echo or .csv charge/claims data. This Machine Learning (ML) API is, in terms of analogous items to the electrical smart grid from which it is paralleled, the "plug" portion to be able to plug into the grid.

Embodiments provides healthcare supply and demand "situation analysis" for Community Benefit/Best Practice Adoption (via search space pruning and parallel processing). More specifically, embodiments match healthcare supply flexible resources to healthcare demands, and intersect this supply and demand with the best detailed process. Then comparison processes (e.g. 2 physicians for 2 or more apples-to-apples cases and situations) can be digested into IHBP Process Maps to consider for comparative effectiveness research via self-evaluation.

An embodiment begins with input HL7 files, leads all the way through the intermediate CSVs, and final Task Force Supply-to-PatientDoctor Demand Smartgrid report that allocates tasks to healthcare providers to ensure that IHBP tasks are performed. Thus, embodiments improve Community Benefit/Best Practice Adoption for "wider" (i.e. include indirect care) and "longer" (i.e. pre- and post-acute care) Best Practices, which include the ideal utilization of flex resources by addressing healthcare cost-effectiveness before consideration of rationing is required.

In addition, preparing for pandemics, via a "capacity surge protection" using the grid (whether on Internet, or just a local intranet—or even "floppy net"/USB, and robot's "onboard" brains), to process available data even if broadband Internet coverage is at risk, spotty, or even non-existent in the area. This includes analyzing audio/visual data automatically if all that's available is low speed modem transmission. Thus, use of a robot offers a self-contained, distributed, and scalable EMR to turn any building with beds like a Nursing Home, shelter, or even hotels into sub-acute care centers during pandemics, and then offers a mobile "patient.complexity" analyzer.

In an embodiment, the plug inputs: (1) (Simple) synonym examples—for HL7 types of records; (2) (Simple) structure examples—for HL7 types of records; (3) (complex) dictation examples—to be able to extract sections of each type of dictation—for example, in an embodiment, documents can have a list of acceptable sections, and sections have 2 lists: acceptable start markers, and then end markers; and (4) (facility-specific findings are there to incorporate eventually into KB). Other data can be input via a plug according to embodiments if desired.

Once HL7 complete records are extracted for labs, meds, and simple order/result items as well as simple CPOE, then entire record goes into modeling column in TVM for single factor modeling (e.g., BNP OR Lasix OR ECHO result).

Because dictations are more complex, in an embodiment they are further segmented (while also described for audit sourcing, like H&P_Impression) and put into their own columns to mix and match for the overall modeling, and to weight those sections differently depending on situation.

These 2 sets of data then can be merged on final sheet that looks at patients found, lists the unique FINS (or instead MRNs and Admission Dates) on a sheet, to then merge via lookups of BNP 1, 2, n, then Dict 1-Sect 1, Dict 1-Sect 2, Dict-2, Sect 1, etc.

In an embodiment, the plug is an Automated Data Integrator And HL7 Converter ("ADIAHC"). According to an embodiment, the data mining/process mining makes data/processes manageable and strives to avoid information/work overload. The plug helps to make "educated guesses" of where data is, how well it matches, and provide a head start to making it harnessable.

In an embodiment, the plug translates to CFG file changes initially/maintained after approval by a human monitor, to then create HL7 data records daily. For example in an embodiment, the plug can use automated:
 ontology "possible location" locator for any type of unstructured data (but w/"anchorable" points);
 probability of pattern match assigner (can calculate a degree of fit or match); and
 linker to extract upon confirmation (into an HL7 format that can then use the CreateHdr PGM to collate).

Thus, in an embodiment, the plug enables data to map to a rules engine, and translates for valuations to determine spreads, using in part prior similar live data and "fuzzy matching" in current file set. The data so harnessed can then be quickly translated/linked to most data by, for example, normalizing to common meanings in different formats in files, such as:
 2 different files in same client (e.g. Acct# vs. FIN, or record w/ FIN & MRN & date vs. another with just MRN and date, but need FIN);
 2 different clients (e.g. KMC PYXIS vs. MMC PHARMNET); or
 2 different data types (e.g. KMC Practice Summary vs. EBM)

In an embodiment, the plug can accomplish this by:
(1) Looking for possible markers (e.g. BNP, Brain Nat). For example, for the "concept" of BNP lab value:
 "BNP=100 ng/ml" would be first record at Hosp.1,
 then "BNP=600 ng/ml" would be second record at Hosp.1,
 then "Brain Nat: 200 ng/ml" would be first record at Hosp.2,
 then "Brain Nat: 600 ng/ml" would be second record at Hosp.2,
(2) Extracting the "area" around the identified marker (so line or sentence, or multiple lines, so thus may include value) so we know the context to whatever degree possible. For example,
 Hosp.1:
  Brain Natriuretic Peptide Test1
  BNP=100 ng/ml
  EndTest
  Brain Natriuretic Peptide Test1
  BNP=600 ng/ml
  EndTest
 Hosp.2:
  Brain Natriuretic Peptide TestA
  Brain Nat: 200 ng/ml
  End of Test
  Brain Natriuretic Peptide TestA
  Brain Nat: 600 ng/ml
  End of Test
(3) Then getting the consistent substring that MAY be it (BNP BNP, Brain Natriureti), as well as getting the value range or enumerated set of values, for what substring and variable that may be the best item to search for and extract. For example
 If doing range, which would be ideal if all values are numeric:
  Hosp.1:
   BNP=<number range: 100 to 600> ng/ml
  Hosp.2:
   Brain Nat: <number range: 200 to 600> ng/ml
 OR ELSE
 If doing enumerated set, which would be ideal if values are not all numeric:
  Hosp.1:
   BNP=<enumerated set: 100, 600> ng/ml
  Hosp.2:
   Brain Nat: <enumerated set: 200, 600> ng/ml
(4) Then finally assign some sort of "probability" value to the fuzzy match. For example:
 "BNP=<number range: 100 to 600> ng/ml" matches "Brain Nat: <number range: 200 to 600> ng/ml" 100%.

In an embodiment, PERL is used to interface with Excel to take HL7 messages and input them to Excel. The messages can be filtered. The inputted messages are used to tabulate records or their fields quickly, and to provide better visual graphs. This allows users to more easily and quickly manipulate that information to use for modeling and further data mining for earlier intervention. This translation and valuation modeling ("TVM") process translates HL7 or other health records formats into Excel to enable rapid valuing of data elements via scoring and weighting to complete various healthcare models as described herein to predict and estimate certain types of characteristics or outcomes. Once outcomes are available, the weights can be timed to result in more accurate prediction or establish a feedback loop of outcome data to change the weighting and scoring for raw data elements.

The foregoing disclosure of the preferred embodiments of the present invention has been presented for the purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may by varied and still remain within the spirit and scope of the present invention.

What is claimed is:

1. A healthcare provisioning system, comprising:
   a computer;
   a healthcare demand model that predicts a healthcare demand based on a series of tasks that need to be performed in response to a patient diagnosis;
   a healthcare supply model that predicts a healthcare supply resource required to perform a task predicted by the healthcare demand model;
   a healthcare provisioning engine executing on the computer configured to analyze the predicted healthcare demand and the predicted healthcare supply resource to predict when the healthcare supply resource will reach a tipping point, and to determine allocation of healthcare supply resources to meet healthcare demand to avoid reaching the tipping point of the healthcare supply resource; and
   a camera to perform real-time surveillance of a healthcare provider that is used by healthcare provisioning engine to determine is a tipping point is being reached or exceeded,
   wherein the healthcare supply model includes a cognitive capacity of an available healthcare supply, and wherein the healthcare provisioning engine determines one or more resources in the available healthcare supply that have sufficient cognitive capacity to respond to the predicted tasks so as to not reach a tipping point or to cause another healthcare supply resource to reach a tipping point.

2. The healthcare provisioning system of claim 1, wherein the healthcare demand model includes a cognitive consumption of an available healthcare supply required to perform the tasks.

3. The healthcare provisioning system of claim 2, wherein the healthcare provisioning engine determines the cognitive consumption required by the available healthcare supply by analyzing a complexity load for each patient in the healthcare facility, the complexity load determined in accordance with a diagnosis for each patient.

4. The healthcare provisioning system of claim 1, wherein the healthcare provisioning engine determines when an intervention is required to offload one or more tasks from a healthcare supply resource that would otherwise reach a tipping point.

5. The healthcare provisioning system of claim 1, wherein the healthcare provisioning engine updates the healthcare demand model.

6. The healthcare provisioning system of claim 1, wherein the healthcare provisioning system identifies tasks at risk and assigns at least one flexible resource to perform that task at risk.

7. The healthcare provisioning system of claim 6, wherein the healthcare provisioning system assigns a priority to each task at risk, and assigns a flexible resource to ensure that the highest priority task at risk is performed.

8. A method for providing healthcare, comprising
   generating a healthcare demand model on a computer that predicts a healthcare demand based on a series of tasks that need to be performed in response to a patient diagnosis;
   generating a healthcare supply model on the computer that predicts a healthcare supply required to perform a task predicted by the healthcare demand model;
   analyzing the predicted healthcare demand and supply to predict when the healthcare supply resource will reach a tipping point on the computer;
   allocating healthcare supply resources to meet healthcare demand to avoid reaching the tipping point of the healthcare supply resource; and
   determining a cognitive capacity of an available healthcare supply
   determining one or more resources in the available healthcare supply that have sufficient cognitive capacity to respond to the predicted tasks so as to not reach a tipping point or to cause another healthcare supply resource to reach a tipping point; and
   using a camera to perform real-time surveillance of a healthcare provider that is used by healthcare provisioning engine to determine is a tipping point is being reached or exceeded.

9. The method of claim 8, further comprising determining a cognitive consumption of an available healthcare supply required to perform the tasks.

10. The method of claim 8, further comprising determining the cognitive consumption required by the available healthcare supply by analyzing a complexity load for each patient in the healthcare facility, the complexity load determined in accordance with a diagnosis for each patient.

11. The method of claim 8, further comprising determining when an intervention is required to offload one or more tasks from a healthcare supply resource that would otherwise reach a tipping point.

12. The method of claim 8, further comprising updating the healthcare demand model.

13. The method of claim 8, further comprising identifying tasks at risk and assigns at least one flexible resource to perform that task at risk.

14. The method of claim 13, further comprising assigning a priority to each task at risk, and assigns a flexible resource to ensure that the highest priority task at risk is performed.

15. A healthcare provisioning system, comprising:
- a computer;
- a healthcare demand model that predicts a healthcare demand based on a series of tasks that need to be performed in response to a patient diagnosis;
- a healthcare supply model that predicts a healthcare supply resource required to perform the tasks predicted by the health demand model;
- a biometric sensor configured to detect a biometric parameter of a healthcare provider that is used to predict whether the healthcare provider is nearing or has reached a tipping point;
- a healthcare provisioning engine executing on the computer to analyze the predicted healthcare demand and the predicted healthcare supply resource to predict when the healthcare supply resource will reach a tipping point, and to determine allocation of healthcare supply resources to meet healthcare demand to avoid reaching the tipping point of the healthcare provider or any other healthcare supply resource; and
- a camera to perform real-time surveillance of a healthcare provider that is used by healthcare provisioning engine to determine is a tipping point is being reached or exceeded,
- wherein the healthcare supply model includes a cognitive capacity of an available healthcare supply, and wherein the healthcare provisioning engine determines one or more resources in the available healthcare supply that have sufficient cognitive capacity to respond to the predicted tasks so as to not reach a tipping point or to cause another healthcare supply resource to reach a tipping point.

16. The healthcare provisioning system of claim 15, wherein the biometric sensor monitors one of a stress and a fatigue of the healthcare provider.

17. The healthcare provisioning system so claim 15, wherein the camera detects facial expressions of the healthcare provider to determine whether the healthcare provider has reached a tipping point.

* * * * *